US012383422B2

(12) United States Patent
Manstein et al.

(10) Patent No.: US 12,383,422 B2
(45) Date of Patent: Aug. 12, 2025

(54) SYSTEMS AND METHODS FOR THERMAL TREATMENT OF TISSUE

(71) Applicant: The General Hospital Corporation, Boston, MA (US)

(72) Inventors: Dieter Manstein, Coral Gables, FL (US); Seyed Reza Monazami Miralipour, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1700 days.

(21) Appl. No.: 16/478,839

(22) PCT Filed: Jan. 19, 2018

(86) PCT No.: PCT/US2018/014578
§ 371 (c)(1),
(2) Date: Jul. 17, 2019

(87) PCT Pub. No.: WO2018/136830
PCT Pub. Date: Jul. 26, 2018

(65) Prior Publication Data
US 2020/0054482 A1 Feb. 20, 2020

Related U.S. Application Data

(60) Provisional application No. 62/541,650, filed on Aug. 4, 2017, provisional application No. 62/532,343, filed
(Continued)

(51) Int. Cl.
*A61F 7/00* (2006.01)
*A61F 7/02* (2006.01)
*A61F 7/12* (2006.01)

(52) U.S. Cl.
CPC ........ *A61F 7/00* (2013.01); *A61F 2007/0058* (2013.01); *A61F 2007/0068* (2013.01);
(Continued)

(58) Field of Classification Search
CPC ................ A61F 7/00; A61F 2007/0058; A61F 2007/0068; A61F 2007/0096;
(Continued)

(56) References Cited

U.S. PATENT DOCUMENTS 5,190,539 A 3/1993 Fletcher
5,417,686 A 5/1995 Peterson
(Continued)

FOREIGN PATENT DOCUMENTS

CN 1535126 A 5/2010
WO 2004064914 A2 8/2004
(Continued)

OTHER PUBLICATIONS

International Searching Authority, International Search Report and Written Opinion for application PCT/US2018/014578, mailed on May 31, 2018.
(Continued)

*Primary Examiner* — Joseph A Stoklosa
*Assistant Examiner* — Adam J Avigan
(74) *Attorney, Agent, or Firm* — QUARLES & BRADY LLP

(57) ABSTRACT

Systems and methods for a medical device configured to provide cooling to a tissue region are provided. The medical device may be configured to noninvasively or invasively cool the tissue region to a predetermined operating temperature via a two-phase heat transfer process.

20 Claims, 33 Drawing Sheets

Related U.S. Application Data on Jul. 13, 2017, provisional application No. 62/523,492, filed on Jun. 22, 2017, provisional application No. 62/511,837, filed on May 26, 2017, provisional application No. 62/500,047, filed on May 2, 2017, provisional application No. 62/482,027, filed on Apr. 5, 2017, provisional application No. 62/447,997, filed on Jan. 19, 2017.

(52) U.S. Cl.
CPC ............... *A61F 2007/0096* (2013.01); *A61F 2007/0258* (2013.01); *A61F 2007/126* (2013.01)

(58) Field of Classification Search
CPC ........ A61F 2007/0258; A61F 2007/126; A61F 7/007; A61F 2007/0059; A61F 2007/0215; A61F 2007/0226; A61F 2007/026; A61F 2007/0268; A61F 7/02; A61F 7/0053; A61F 7/12; A61F 2007/0086; A61F 2007/029; A61B 2018/00011; A61B 2018/00029; A61B 18/203; A61B 2018/00452; A61B 2018/00577; F28D 15/046

See application file for complete search history.

(56) References Cited

U.S. PATENT DOCUMENTS

| | | | |
|---|---|---|---|
| 6,059,820 | A | 5/2000 | Baronov |
| 6,126,684 | A | 10/2000 | Gobin |
| 6,189,327 | B1 | 2/2001 | Strauss |
| 6,257,011 | B1 | 7/2001 | Siman-Tov |
| 6,364,899 | B1 | 4/2002 | Dobak, III |
| 6,533,029 | B1 | 3/2003 | Phillips |
| 7,104,984 | B2 | 9/2006 | Ryba |
| 7,344,499 | B1 | 3/2008 | Prausnitz |
| 7,473,244 | B2 | 1/2009 | Frazier |
| 7,721,349 | B1 | 5/2010 | Strauss |
| 8,579,892 | B2 | 11/2013 | Hoey |
| 9,149,896 | B1* | 10/2015 | Batty ............ B21D 53/08 |
| 9,351,792 | B2 | 5/2016 | Manstein |
| 9,408,656 | B2 | 8/2016 | Littrup |
| 10,217,692 | B2 | 2/2019 | Haj-Hariri |
| 2004/0084174 | A1 | 5/2004 | Achenbrach |
| 2005/0065581 | A1 | 3/2005 | Fletcher |
| 2005/0251120 | A1 | 11/2005 | Anderson |
| 2006/0155266 | A1 | 7/2006 | Manstein |
| 2007/0043342 | A1 | 2/2007 | Kleinberger |
| 2007/0084587 | A1* | 4/2007 | Huang ............ F28D 15/046 165/104.26 |
| 2007/0149957 | A1 | 6/2007 | Ross |
| 2008/0009923 | A1 | 1/2008 | Paithankar |
| 2008/0015555 | A1 | 1/2008 | Manstein |
| 2009/0118722 | A1 | 5/2009 | Ebbers et al. |
| 2010/0186931 | A1* | 7/2010 | Obara ............ F28D 15/046 165/104.26 |
| 2010/0286755 | A1 | 11/2010 | Gallaher |
| 2011/0060322 | A1 | 3/2011 | Manstein |
| 2012/0158100 | A1 | 6/2012 | Schomacker |
| 2013/0233000 | A1 | 9/2013 | Hodgson |
| 2014/0303696 | A1 | 10/2014 | Anderson |
| 2014/0343542 | A1 | 11/2014 | Karnik |
| 2014/0350537 | A1 | 11/2014 | Baust |
| 2015/0080769 | A1 | 3/2015 | Lotsch |
| 2015/0198380 | A1 | 7/2015 | Haj-Hariri |
| 2015/0216719 | A1 | 8/2015 | DeBenedictis |
| 2016/0270850 | A1 | 9/2016 | Manstein |
| 2016/0324578 | A1 | 11/2016 | Manstein |
| 2017/0007309 | A1 | 1/2017 | DeBenedictis et al. |

FOREIGN PATENT DOCUMENTS

| | | | |
|---|---|---|---|
| WO | 2005107834 | A1 | 11/2005 |
| WO | 2015117005 | A1 | 8/2015 |

OTHER PUBLICATIONS

European Patent Office. Extended European Search Report for application 18742121.9. Mailed on Jul. 13, 2020.

* cited by examiner

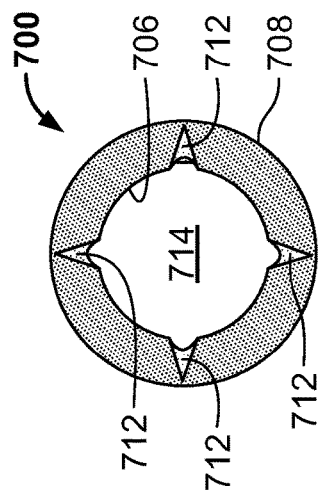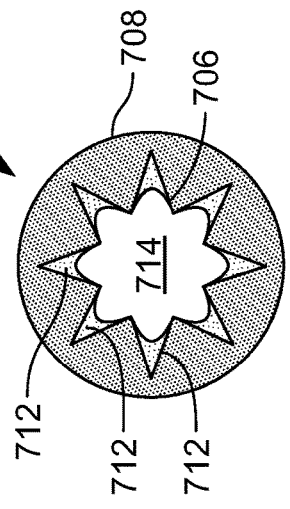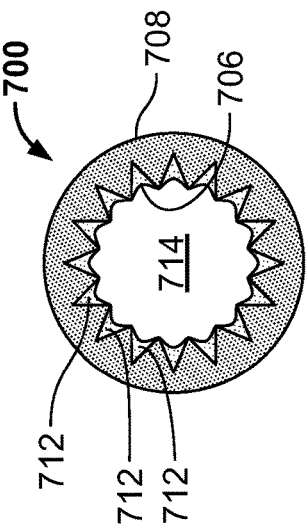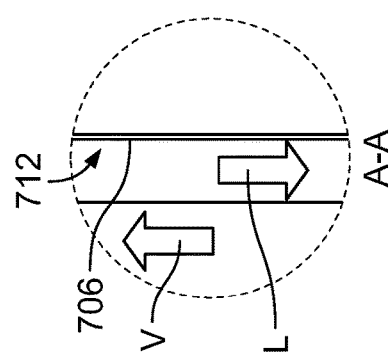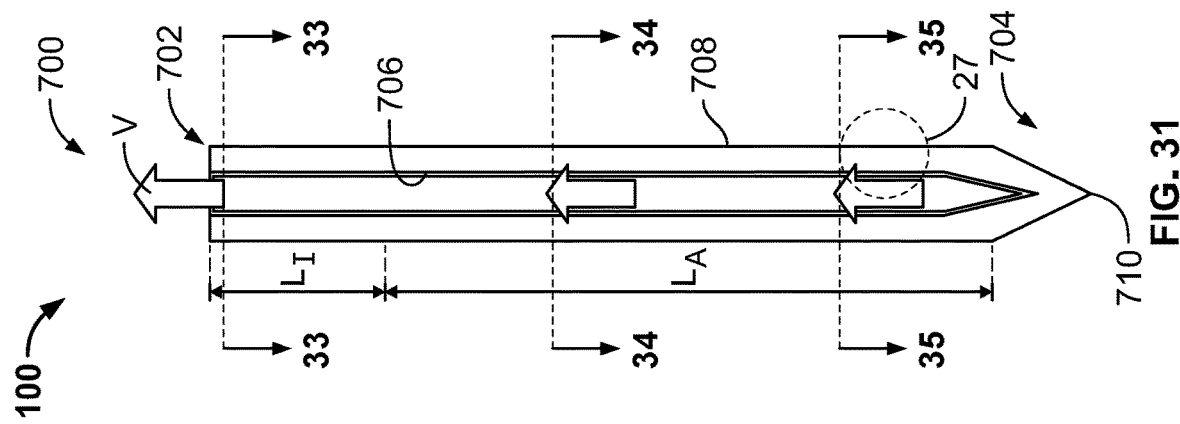

Time = 0.059 s Temperature (degC)

Time = 0.073 s Isosurface Temperature (degC)

SYSTEMS AND METHODS FOR THERMAL TREATMENT OF TISSUE

CROSS-REFERENCE TO RELATED APPLICATIONS

The present application is a U.S. National Phase of PCT Application No. PCT/US2017/049850 filed on Sep. 1, 2017, which is based on, claims priority to, and incorporates herein by reference in their entirety, U.S. Provisional Patent Application No. 62/447,997, filed on Jan. 19, 2017, Unites States Provisional Patent Application No. 62/482,027, filed on Apr. 5, 2017, U.S. Provisional Patent Application No. 62/500,047, filed on May 2, 2017, U.S. Patent Application No. 62/511,837, filed on May 26, 2017, U.S. Provisional Patent Application No. 62/523,492, filed on Jun. 22, 2017, U.S. Provisional Patent Application No. 62/532,343, filed on Jul. 13, 2017, and U.S. Provisional Patent Application No. 62/541,650, filed on Aug. 4, 2017.

STATEMENT REGARDING FEDERALLY SPONSORED RESEARCH

Not Applicable.

BACKGROUND

In some medical applications, cooling may be selectively applied to a tissue region to perform a desired medical procedure (e.g., cryolipolysis). Alternatively, cooling may be implemented to protect non-target tissue during a heat treatment procedure performed on a target tissue region (e.g., laser ablation). Conventional cooling systems implemented in these medical applications suffer from insufficient cooling capacity and require various moving components and external power supplies.

BRIEF SUMMARY

The present disclosure provides systems and methods for a medical device configured to provide cooling and/or heating to a tissue region. The medical device leverages two-phase heat transfer to provide an extremely high cooling capacity when compared to conventional state-of-the-art cooling mechanisms (e.g., single-phase cooling, thermoelectric cooling, Joule-Thompson cooling, spray cooling, etc.). The medical device may be configured to noninvasively or invasively cool the tissue region to a predetermined temperature. In some non-limiting examples, the two-phase heat transfer leveraged by the medical device to provide cooling may be combined with a heating element to enable the medical device to selective switch between providing heating and cooling to a tissue region.

In one aspect, the present disclosure provides a medical device configured to provide cooling to a tissue region. The medical device includes a base and an evaporative structure arranged on the base and configured to receive a working fluid. The evaporative structure is designed to promote evaporation of the working fluid to cool the base to a predetermined operating temperature.

In one aspect, the present disclosure provides a noninvasive medical device configured to provide cooling to a tissue region. The noninvasive medical device includes a base having a treatment surface arranged thereon, and a porous substrate in engagement with at least a portion of the base and configured to receive a working fluid. The porous substrate is designed to promote evaporation of the working fluid to cool the treatment surface to a predetermined operating temperature.

In one aspect, the present disclosure provides an invasive medical device configured to provide cooling to a tissue region. The invasive medical device includes an outer wall, and an inner wall having at least one channel thereon and that extends axially therealong. The at least one channel is designed to promote evaporation of a working fluid arranged therein to cool the outer surface to a predetermined operating temperature.

In one aspect, the present disclosure provides a noninvasive medical device configured to provide cooling to a tissue region subjected to a fractional treatment pattern. The noninvasive medical device includes a base defining a plurality of openings arranged therein to accommodate the fractional treatment pattern, and a plurality of channels arranged on the base and configured to receive a working fluid. The plurality of channels are designed to promote evaporation of the working fluid to cool the base to a predetermined operating temperature.

In one aspect, the present disclosure provides a noninvasive medical device configured to provide cooling to a tissue region. The noninvasive medical device includes a top plate, a bottom plate including a contact surface, and an evaporative structure arranged between the top plate and the bottom plate configured to receive a working fluid. The evaporative structure is configured to promote evaporation of the working fluid to cool the contact surface. The noninvasive medical device includes an opening extending through the top plate, the bottom plate, and the evaporative structure.

In one aspect, the present disclosure provides a noninvasive medical device configured to provide cooling to a tissue region. The noninvasive medical device includes a transparent top plate including an inlet port and an outlet port, and a transparent bottom plate including a bottom surface configured to engage the tissue region and an evaporative structure in fluid communication with the inlet port and the outlet port. The inlet port is configured to receive a working fluid and the evaporative structure is configured to promote evaporation of the working fluid to cool the desired tissue region to a predetermine temperature.

In one aspect, the present disclosure provides a noninvasive medical device configured to provide cooling to a tissue region. The noninvasive medical device includes a base having a condensing plate with a treatment surface arranged thereon and an inlet port and an outlet port, and a evaporative plate having an evaporative structure arranged therein. The condensing plate includes a flow path extending between the inlet port and the outlet port and is configured to receive a cooling fluid, and wherein the evaporative structure is configured receive a working fluid and to promote evaporation of the working fluid to cool the treatment surface to a predetermined operating temperature.

In one aspect, the present disclosure provides a method for control a medical device configured to thermally treat a tissue region. The method includes engaging a medical device with a tissue region, measuring a temperature at one or more locations along a surface of the tissue region, determining a temperature profile at one or more depths within the tissue region based on the measured temperature at the one or more locations along the surface of the tissue region, and adjusting an operational parameter of the medical device based on the determined temperature profiled at the one or more depths within the tissue region.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 31 is a schematic illustration of an invasive medical device according to one aspect of the present disclosure.

FIG. 32 is an enlarged view of section A-A of the invasive medical device of FIG. 31.

FIG. 33 is a cross-section view of the invasive medical device of FIG. 31 taken along line 33-33.

FIG. 34 is a cross-section view of the invasive medical device of FIG. 31 taken along line 34-34.

FIG. 35 is a cross-section view of the invasive medical device of FIG. 31 taken along line 35-35.

DETAILED DESCRIPTION

The use of the terms "upstream" and "downstream" herein indicates a direction relative to the flow of fluid. The term "downstream" corresponds to the direction of fluid flow, while the term "upstream" refers to the direction opposite or against the direction of fluid flow.

Figure 1:
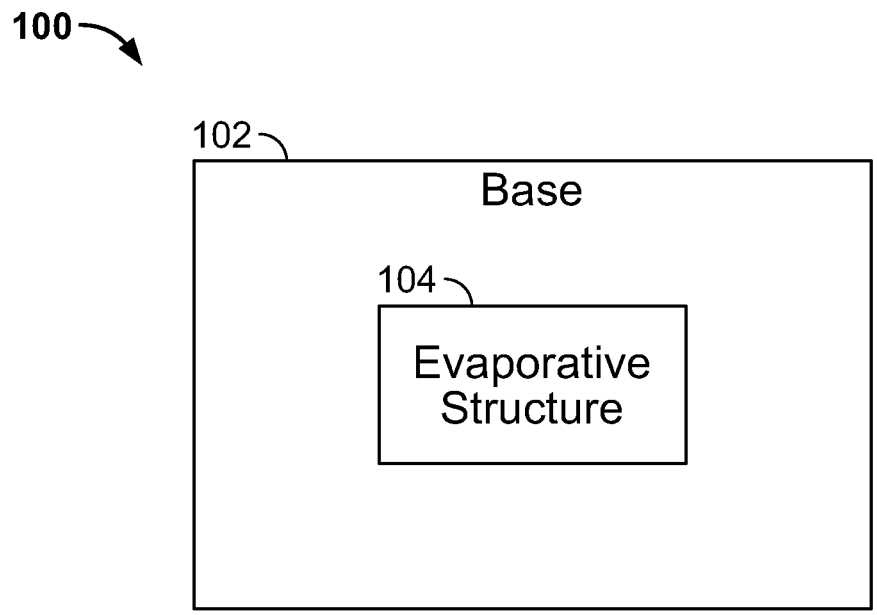
FIG. 1 is a schematic illustration of a medical device according to one aspect of the present disclosure.

FIG. 1 illustrates one non-limiting example of a medical device 100 according to one aspect of the present disclosure. The medical device 100 may be configured to provide cooling to a tissue region, or an array of tissue regions, either noninvasively (e.g., at a surface of the tissue region) or invasively (e.g., at a predetermined depth into the tissue region). The medical device 100 includes a base 102 and an evaporative structure 104. The base 102 is configured to contact a tissue region to facilitate the removal of heat from the tissue region, thereby cooling the tissue region to a predetermined temperature. In some non-limiting examples, the medical device 100 may be configured to cool the tissue region to a desired temperature profile as a function of time.

In some non-limiting examples, the base 102 may be a noninvasive implement designed to continuously contact a surface of a tissue region to cool the tissue region at the surface and/or to a predetermined depth into the tissue region. In some non-limiting examples, the base 102 may be a noninvasive implement designed to discretely contact a surface of a tissue region in a desired fractional pattern to provide fractional cooling over the tissue region and/or to a predetermined depth into the tissue region. In some non-limiting examples, the base 102 may be a noninvasive implement designed to provide thermal management (i.e., cooling) adjacent to or around a fractional heating pattern to minimize damage to non-target tissue between the fractional heating areas. In some non-limiting examples, the base 102 may be an invasive implement configured to penetrate into a tissue region, or an array of tissue regions, to provide cooling to the tissue region(s) at a predetermined depth, or a range of depths.

In some non-limiting examples, the evaporative structure 104 may be in contact with or integrated into the base 102. The evaporative structure 104 is configured to receive a working fluid to facilitate cooling of a tissue region via a two-phase heat transfer process. The evaporative structure 104 is designed to include one or more of cavities and/or one or more flow paths formed therein, each configured to be filled with the working fluid. Once filled with the working fluid, liquid menisci are formed within each of the cavities or paths due to the combined effect of capillary and short range forces. The liquid menisci act as evaporation sites that provide significant heat removal potential from the evaporative structure 104 and the base 102 due to the large enthalpy of vaporization of liquids. Thus, the medical device 100 is operable to provide cooling to a tissue region via a two-phase heat transfer process, which provides a heat removal capacity as high as several orders of magnitude greater than conventional medical cooling technologies (e.g., single-phase cooling, thermoelectric cooling, Joule-Thompson cooling, etc.).

In the illustrated non-limiting example, the evaporative structure 104 may not be required to receive a continuous flow of fluid. Rather, the evaporative structure 104 may be filled or charged with a predetermined quantity of the working fluid. Alternatively or additionally, the evaporative structure 104 may be initially brought into fluid communication with a source of the working fluid, and the capillary forces provided by the design of the evaporative structure 104 cause the working fluid to flow into the evaporative structure 104 without the requirement of an externally induced pressure differential (e.g., a pump). In some non-limiting examples, the evaporative structure 104 may be coated with a material that possesses a high surface tension (e.g., a single layer of graphite, or graphene). Once filled, the evaporative structure 104 may be removed from fluid communication with the source of working fluid. The evaporative structure 104 may be designed to initiate and maintain evaporation of the working fluid, once the base 102 is brought into contact with a tissue region. That is, heat transferred from the tissue region through the base 102 and to the evaporative structure 104 is sufficient to initiate and maintain the evaporation of the working fluid and, thereby, the cooling of the tissue region. Thus, the medical device 100 is operable to provide cooling to a tissue region without the requirement of an external power supply, or heat source, to facilitate the evaporation of the working fluid therein. In some non-limiting examples, this enables the medical device 100 to operate as a passive device (i.e., does not require an external source of energy to operate) and to possess increased mobility over conventional medical cooling system, which require wires, power supplies, etc., to operate. Alternatively or additionally, the evaporative structure 104 may be designed such that the capillary forces maintain the working fluid within the evaporative structure 104 regardless of the orientation of the medical device 100. That is, the capillary forces within the evaporative structure 104, once filled, may be greater than the force of gravity enabling the medical device 100 to be used in any orientation without the threat of leakage of the working fluid or partially dry areas in the evaporative structure 104.

Due to the thermodynamic operation of the of the medical device 100, an amount of working fluid needed to cool a tissue region to a desired temperature for a desired amount of time is known. That is, the rate of evaporation of the working fluid from the evaporative structure 104 may be known based on the heat input from the tissue region. In this way, the medical device 100 may be tailored to provide a desired amount of cooling for a desired amount of time. Alternatively or additionally, the known amount of time for a given mass of working fluid to evaporate may be utilized to determine when the working fluid needs to be re-filled and/or when a different working fluid may be communicated to the evaporative structure 104 to control the temperature of the tissue region.

The medical device 100 may be operable with a variety of different working fluids. For example, water, a liquid hydrocarbon or alcohol, halogenated hydrocarbons, ammonia, carbon dioxide, to name a few. In some non-limiting examples, the working fluid may be chosen based on a specific medical application, desired heat exchange rate, and/or range of operating temperatures. Since evaporative processes are substantially isothermal, the desired temperature range and heat transfer characteristics may be governed by the thermophysical properties of the working fluid. That is, the boiling point of the working fluid is known for a given pressure and temperature and, thus, an equilibrium temperature achieved by the medical device 100 may be determined based at least in part by the chemical composition of the working fluid. Table 1 below provides various non-limiting examples of the properties and operational characteristics of the medical device 100.

TABLE 1

Properties and Operating Characteristics of the Medical Device 100

| | |
|---|---|
| Operating Range | −220° C. to 200° C. |
| Operating Pressure | 0.01 bar to 10 bar |

TABLE 1-continued

Properties and Operating Characteristics of the Medical Device 100

| | |
|---|---|
| Working Fluids | Hydrocarbons, Hydrofluorocarbons, Hydrofluoroolefins, Alcohols, Water, Aqueous Solution, Nobel Gases, Binary Mixtures, Nanoparticle laden Fluids, Cryogenic Fluids: $N_2$, $O_2$, etc. |
| Substrate Material | Metals, Polymers, Composite Materials, Non-metallic elements E.G., Copper, Aluminum, Graphite, etc. |
| Evaporative Structure | Microgrooved, Fractional Pattern Microchannels, Nano-spheres E.G., Aluminum, Copper, Carbon, Steel, etc. |
| Evaporative Pore Size | 100 nm-2000 μm |
| Coatings | Wetting or non-wetting coating, Gold, Teflon, Anodized Nano-Layers, Nano-structured coatings |
| Fluid Flow Control | Thermo-capillary, Piezo-electric, Expansion Valve, Capillary Tube, Electroosmotic Driven Flow, Electromotive Force |
| Temperature Control | Thermocouple, RTD, Embedded Contact Micro-wires |

When implementing the medical cooling device 100 to cool a desired tissue region, the thermal characteristics of the desired tissue region combined with its structural-mechanics response to change in temperature may play a role in energy-based medical applications. For example, in the case of cryolipolysis, water and fat containing tissues may undergo a phase change as their temperature drops below the melting point for water and/or fat. This phase change (i.e., crystallization) is accompanied with two events in the thermal characteristics of the tissue as well as the energy balance during the cooling process. First, the thermal conductivity for the solid phase is higher than the liquid phase, therefore, the conduction heat transfer may be improved significantly as the frozen front moves into the non-frozen section of the desired tissue region. For example, water possesses a thermal conductivity of approximately four times higher in the solid phase (i.e., ice) when compared to liquid water. This increase in thermal conductivity may induce a cascade of accelerating affects as long as the heat removal capacity is not exceeded and while the distance from the cold surface is not imposing a large resistance on the heat flow. Second, the latent heat of the phase change released at the interface between the frozen and non-frozen sections of tissue may add a significant load to the total heat that should be removed from the desired tissue region. If the cooling capacity is limited, the cooling process is slowed down to match the maximum heat flow that could be dissipated.

These dynamic characteristics of the tissue, explained above, may only be noticed in circumstances where the heat flow from the desired tissue region to the cold surface is not limited by the capacity of the mechanism employed to provide the cooling effect. The two-phase cooling leveraged by the medical device 100 provides superior cooling performance and significantly increased cooling capacity when compared to conventional cooling mechanism (e.g., single-phase cooling, thermoelectric cooling, Joule-Thompson cooling, spray cooling, etc.). The extremely high cooling capacity of the medical device 100 turns the dynamic thermal behavior of the desired tissue region into an advantage to accelerate the progression of the frozen front, enhance the effectiveness of the thermal damage to the desired tissue region by increasing the energy removed from the unit volume of tissue per unit time, reduce the duration of a desired medical procedure, shrink the footprint of the overall medical device 100 and significantly reduce the total weight thereof, reduce the risk of undesired damage to neighboring/non-target tissue, improve the reliability of the medical device 100 due to passive operation, increase the effective range (distance from the cold surface) that can be cooled, and improve the temporal and spatial accuracy in controlling and maintaining the temperature levels.

In some non-limiting examples, the medical device 100 may be configured to provide a step-wise, cyclic, or predetermined temperature profile as a function of time cooling approach by inducing cooling waves into the desired tissue region. For example, if a tissue region is required to be cooled to −10° C., the medical device 100 may be configured to start at an operating temperature of −5° C. and stay there for a first predetermined amount of time. After the first predetermined amount of time, the medical device 100 may be configured to transition to an operating temperature of −15° C. for a second predetermined amount of time. The operating temperature transition between −5° C. and −15° C. may be facilitated, for example, by changing the operating pressure of system and/or changing the working fluid and/or the flow rate of the working fluid, to name a few. Once the second predetermined amount of time has passed, the medical device 100 may be configured to transition back to an operating temperature of −5° C. for a third predetermined amount of time. In some non-limiting examples, the medical device 100 may cyclically continue to transition between −5° C., −15° C., and −5° C. operating temperatures until a total time for a given procedure is reached. The step-wise, or cyclic, transitions in operating temperature may enable the medical device 100 to more efficiently cool the tissue region to the desired −10° C. and reach the desired −10° C. temperature in less time, when compared to providing cooling at a constant −10° C.

In accordance with a non-limiting configuration, the use or method of use of the medical device 100 does not include a step of treatment of a human or animal body by surgery or therapy. It is noted that the skills of a person using a device as described herein, may not have the skills of a physician, and that the intended treatment may not be motivated due to illness of the treated person, rather for aesthetic reasons.

In some non-limiting examples, a suction device may be implemented to adhere the tissue region to the base 102. The suction device may be in the form of a vacuum pump, or another device capable of generating a pressure lower than atmospheric pressure, to suction the tissue region onto the base 102.

Figure 2:
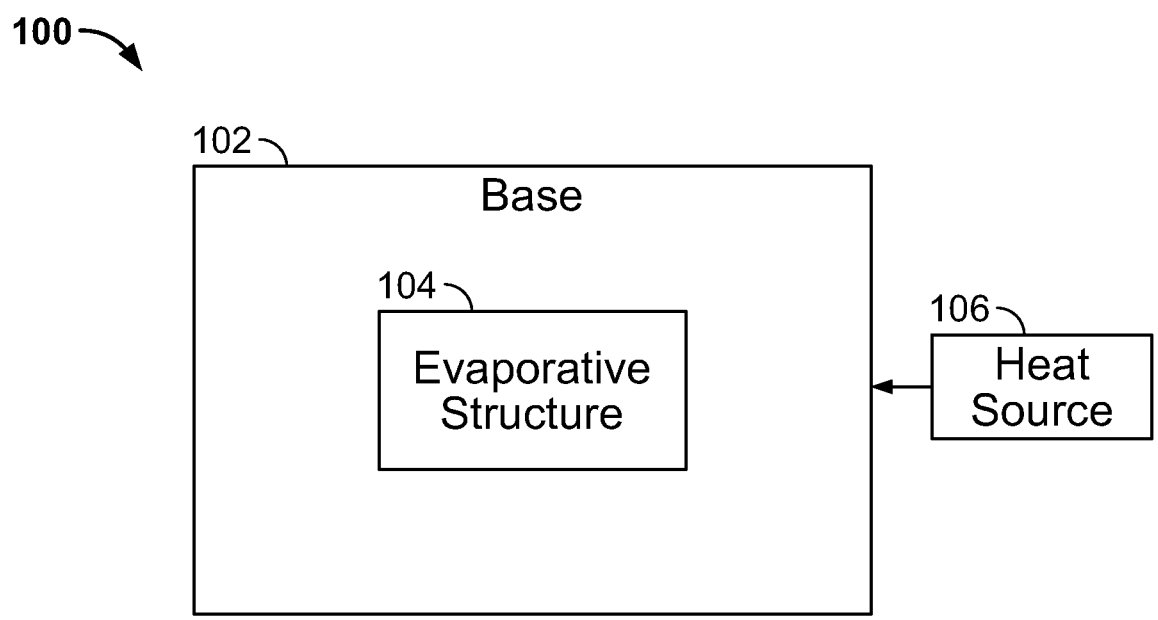
FIG. 2 is a schematic illustration of a medical device in communication with a heat source according to one aspect of the present disclosure.

FIG. 2 illustrates another non-limiting example of the medical device 100 according to one aspect of the present disclosure. As illustrated in FIG. 2, the medical device 100 may include a heat source 106. In some non-limiting examples, the heat source 106 may be a resistive heater, a thin, transparent heater arranged between the base 102 and the tissue region, a thermoelectric heater, a microwave heater, an electromagnetic heater (e.g., infrared), an ultrasound heater, a radio frequency heater etc. In some non-limiting examples, the heat source 106 may leverage waste heat from another component (e.g., a laser) located externally from the base 102.

The heat source 106 may be configured to selectively apply heat to the base 102 and/or a tissue region. In some non-limiting examples, the heat source 106 may be integrated into the base 102 to facilitate the selective heating of the base 102. In some non-limiting examples, the heat source 106 may be located remotely from the base 102 and in thermal communication with the base 102 and/or a tissue region. In operation, the medical device 100 may be used to cool a tissue region for a given medical application, and the heat source 106 may subsequently heat the tissue region and/or an adjacent tissue region back to approximately room temperature. In some non-limiting application, the medical device 100 may freeze at least a portion of the tissue region (e.g., the surface of the tissue region) and the heat source 106 may be used to prevent sticking between the base 102 and the surface of the tissue region. For example, a thin, transparent heat source 106 may be arranged between the base 102 and the surface of the tissue region to facilitate quick removal of the medical device 100 from the surface of the tissue region after the desired cooling has been applied thereto.

Figure 3:
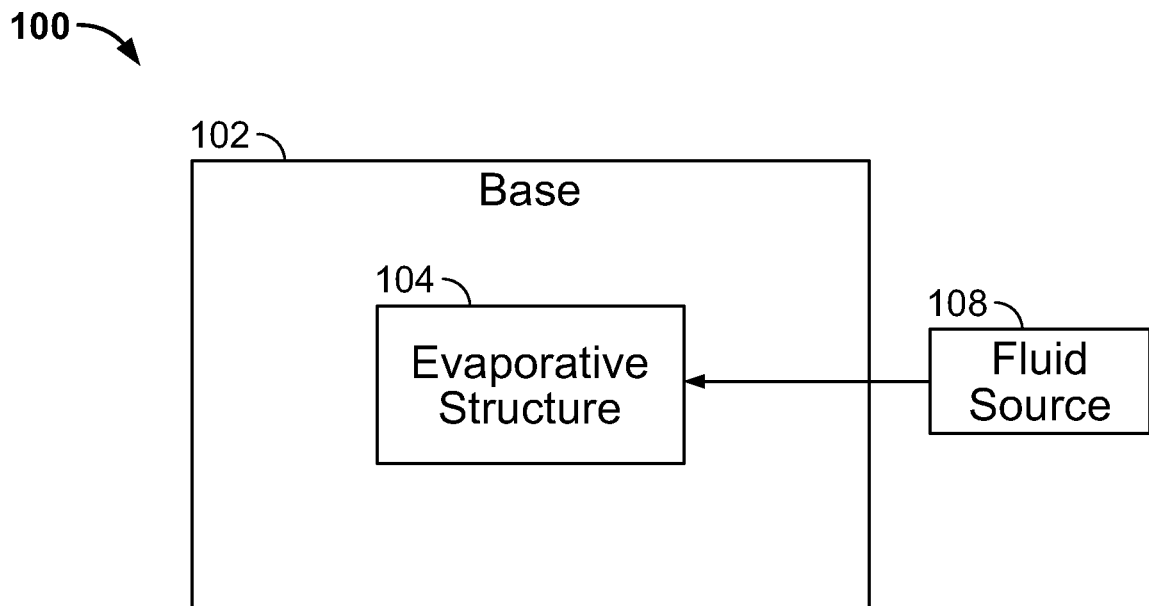
FIG. 3 is a schematic illustration of a medical device in communication with a fluid source according to one aspect of the present disclosure.

FIG. 3 illustrates another non-limiting example of the medical device 100 according to one aspect of the present disclosure. As illustrated in FIG. 3, the evaporative structure 104 may be in fluid communication with a fluid source 108. The fluid source 108 may include a supply of working fluid that may be furnished to the evaporative structure 104. In some non-limiting examples, the fluid source 108 may be a non-pressurized source (i.e., at approximately atmospheric pressure) of working fluid. In these non-limiting example, fluid contact of between the fluid source 108 and the evaporative structure 104 may be sufficient induce capillary forces that supply the evaporative structure 104 with the working fluid. In some non-limiting examples, the fluid source 108 may be configured to induce a pressure drop between the fluid source 108 and the evaporative structure 104 to furnish the working fluid into the evaporative structure 104. In these non-limiting examples, the fluid source 108 may be configured to selectively furnish the working fluid into the evaporative structure 104 (e.g., when it is determined that the evaporative structure 104 requires more working fluid).

Figure 4:
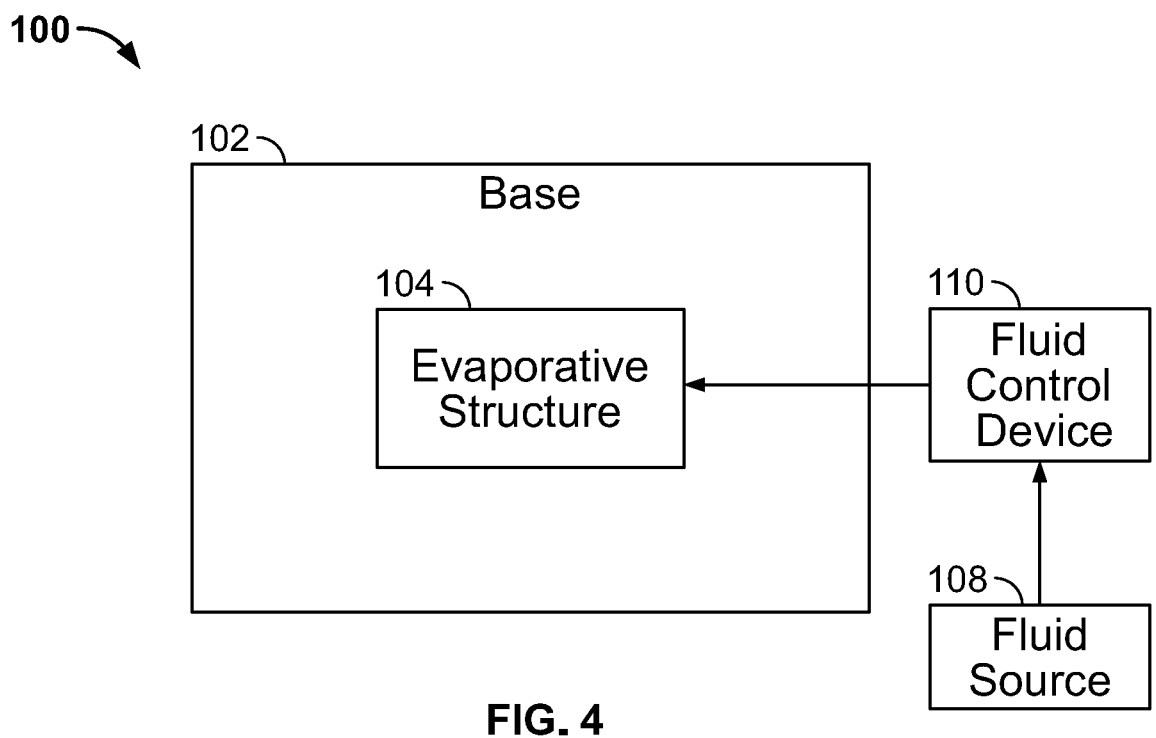
FIG. 4 is a schematic illustration of a medical device in communication with a fluid source and a fluid control device according to one aspect of the present disclosure.

FIG. 4 illustrates another non-limiting example of the medical device 100 according to one aspect of the present disclosure. As illustrated in FIG. 4, the medical device 100 may include a fluid control device 110 in communication with the fluid source 108 and/or the evaporative structure 104. In some non-limiting examples, the fluid control device 110 may be configured to control a direction of the fluid flow between the fluid source 108 and the evaporative structure 104, or the flow rate of the working fluid. For example, the fluid control device 110 may be in the form of a check valve configured to only allow fluid to flow from the fluid source 108 to the evaporative structure 104.

In some non-limiting examples, the fluid control device 110 may be configured to control a pressure of the working fluid provided from the fluid source 108 to the evaporative structure 104. For example, the fluid control device 110 may be in the form of a disposable charged cartridge that is configured to selectively increase the pressure of the working fluid flowing to the evaporative structure 104. In this way, the fluid control device 110 may be utilized to control a cooling temperature output by the medical device 100 by varying the pressure of the working fluid within the evaporative structure 104. Alternatively or additionally, the fluid control device 110 may include a pressure regulator configured to increase or decrease the pressure of the working fluid, as desired.

In some non-limiting examples, the fluid control device 110 may be configured to selectively provide fluid communication between the fluid source 108 and the evaporative structure 104. For example, the fluid control device 110 may be in the form of an on/off valve configured to selectively provide fluid communication between the fluid source 108 and the evaporative structure 104 to activate and deactivate the cooling of a tissue region. It should be appreciated that the various forms of the fluid control device 100 described herein may be combined, and the medical device 100 is not limited to the use of only one of the described functionalities.

Figure 5:
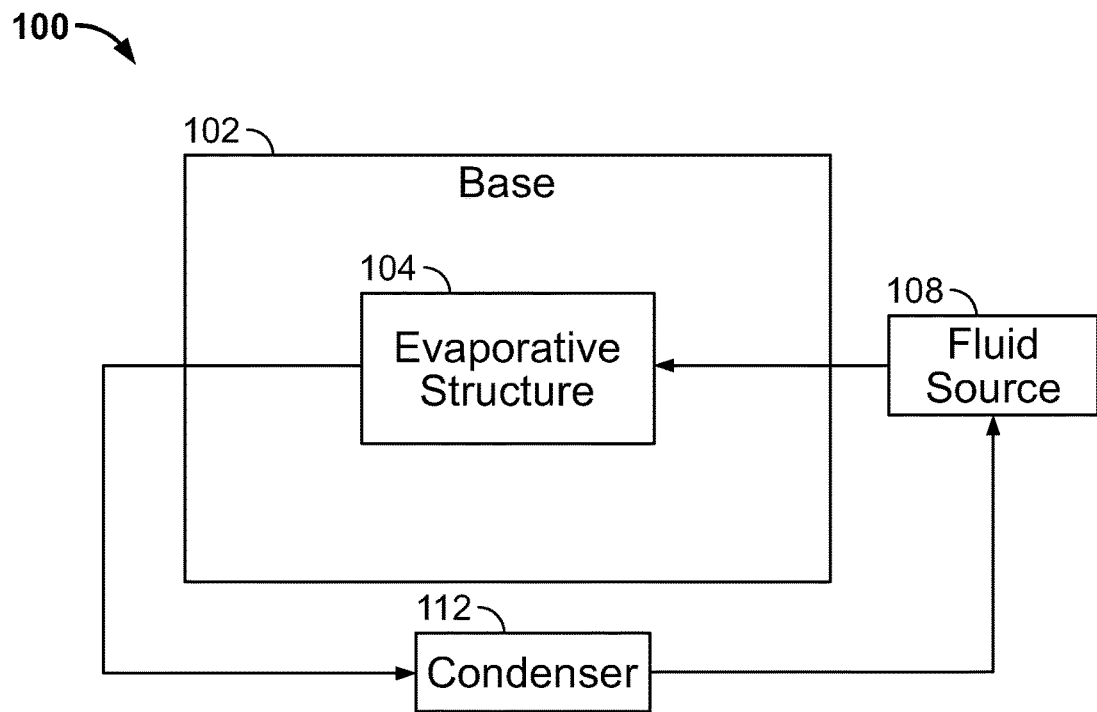
FIG. 5 is a schematic illustration of a medical device in communication with a fluid source and a condenser according to one aspect of the present disclosure.

FIG. 5 illustrates another non-limiting example of the medical device 100 according to one aspect of the present disclosure. As illustrated in FIG. 5, the medical device 100 may include a condenser 112 in fluid communication with the evaporative structure 104. The condenser 112 may be configured to facilitate the condensation of evaporated working fluid that flows from the evaporative structure 104. In some non-limiting examples, the condenser 112 may be configured to provide a sufficient amount of heat removal or dissipation to the working fluid to effectuate the condensation thereof. The condenser 112 may be in fluid communication with the fluid source 108 to recapture the working fluid and provide it to the fluid source 108. In other non-limiting examples, the condenser 112 may be configured to communicate the condensed working fluid to a reservoir, as will be described.

Figure 6:
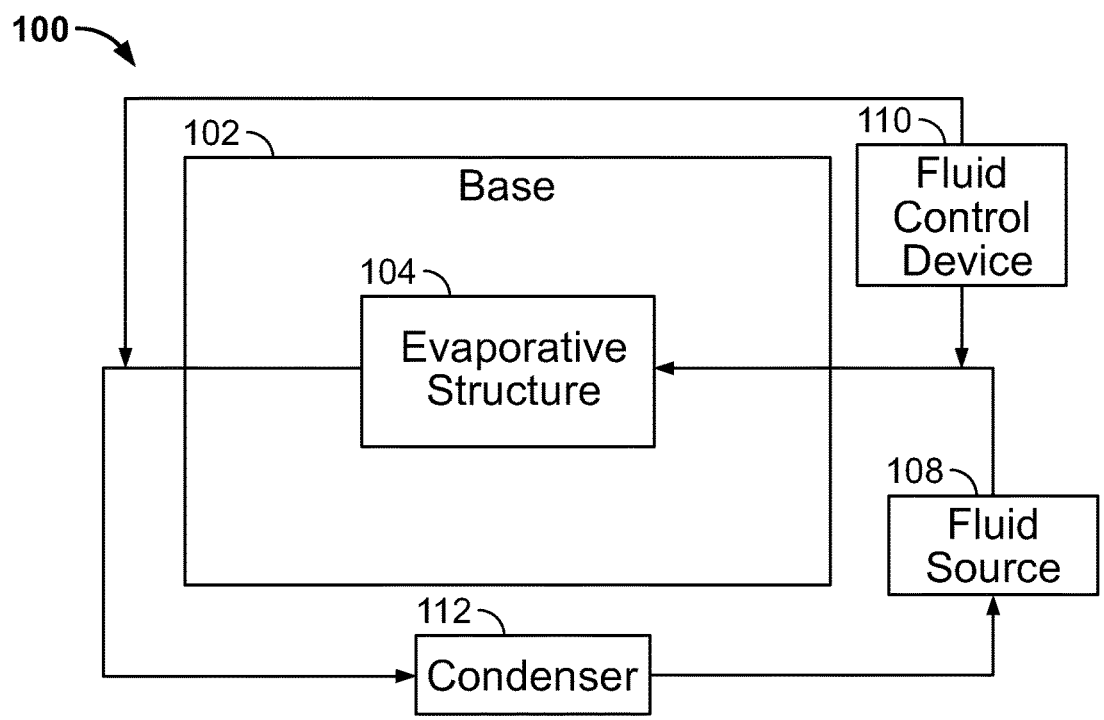
FIG. 6 is a schematic illustration of a medical device in communication with a fluid source, a fluid control device, and a condenser according to one aspect of the present disclosure.

FIG. 6 illustrates another non-limiting example of the medical device 100 according to one non-limiting example of the present disclosure. As illustrated in FIG. 6, the fluid control device 110 may be remotely in fluid communication (i.e., not arranged in-line with the fluid source 108) with the working fluid downstream of the fluid source 108 and downstream of the evaporative structure 104. This configuration may enable the fluid control device 110 to selectively control a pressure of the working fluid flowing into the evaporative section 104 (e.g., to control a cooling temperature provided by the medical device 100) and/or control a pressure of the evaporated working fluid leaving the evaporative structure 104 (e.g., to control the condensing of the evaporated working fluid).

Figure 7:
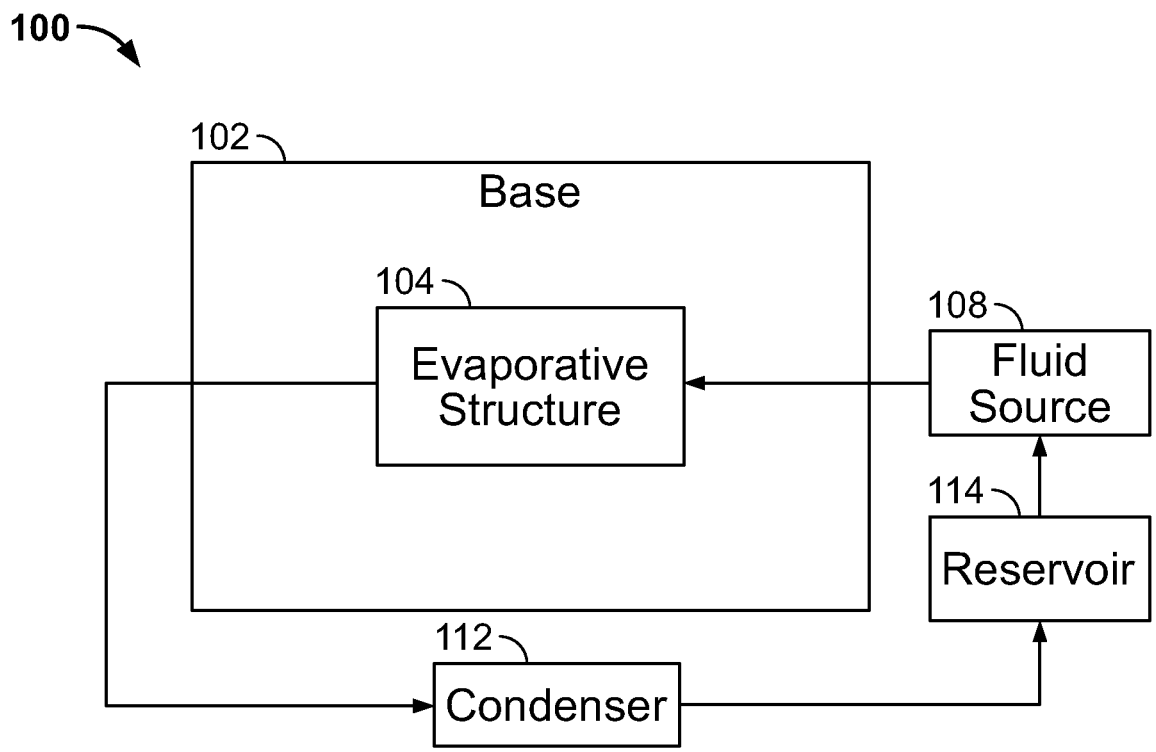
FIG. 7 is a schematic illustration of a medical device in communication with a fluid source, a reservoir, and a condenser according to one aspect of the present disclosure.

FIG. 7 illustrates another non-limiting example of the medical device 100 according to one aspect of the present disclosure. As illustrated in FIG. 7, the evaporative structure 104 may be in fluid communication with the fluid source 108, the condenser 112, and a reservoir 114. In some non-limiting examples, the reservoir 114 may be a tank or vessel at approximately atmospheric pressure that contains working fluid. In some non-limiting examples, the reservoir 114 may be tank or vessel either above or below atmospheric pressure that contains working fluid. The fluid source 108 may be configured to furnish the working fluid from the reservoir 114 to the evaporative structure 104 at a predetermined pressure and flow rate. In some non-limiting examples, the working fluid may flow continually from the fluid source 108 to the evaporative structure 104 through the condenser 112 and back to the reservoir 114. In some non-limiting examples, the working fluid may be selectively provided to the evaporative structure 104, as needed.

The thermal and thermodynamic characteristics of the medical device 100 enable the medical device 100 to be self-adapting, or self-regulating based on the heat input applied thereto. That is, the amount of working fluid evaporated within the evaporative structure 104 and subsequently condensed by the condenser 112 may be proportional to the heat input to the medical device 100 from the tissue. In this way, the medical device 100 may self-regulate the amount of evaporation and subsequent condensing of the working fluid to provide sufficient liquid working fluid to the reservoir 114 and fluid source 108.

Figure 8:
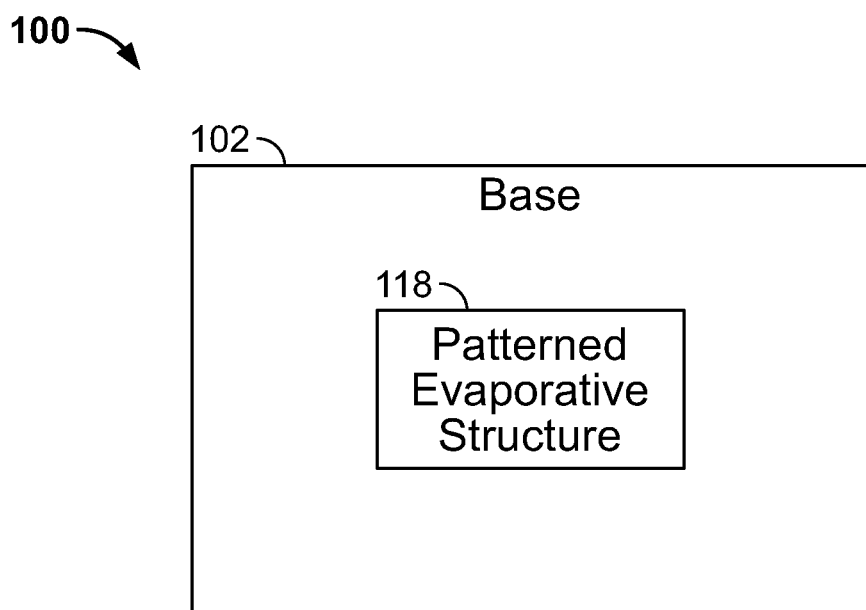
FIG. 8 is a schematic illustration of a medical device having a patterned evaporative structure according to one aspect of the present disclosure.

FIG. 8 illustrates another non-limiting example of the medical device 100 according to one aspect of the present disclosure. As illustrated in FIG. 8, the evaporative structure 104 may be the form of a patterned evaporative structure 118. The patterned evaporative structure 118 may be configured to provide a cooling pattern with varied heat flux to a tissue region. In some non-limiting examples, the mechanical structure of the patterned evaporative structure 118 may be tailored to spatially vary the heat dissipation flux provided by the medical device 100. For example, a porosity of the patterned evaporative structure 118 may be designed to spatially vary the heat removal flux or capacity across the medical device 100. Alternatively or additionally, a material of the base 102, a coating of the base 102 or the patterned evaporative structure 118, and/or an external coating applied between the base 102 and the tissue region may be designed to spatially vary the heat dissipation flux or profile of the medical device 100 to define a cooling pattern. In one non-limiting example, an antifreeze coating, or material, may be applied between the base 102 and the tissue region to protect certain areas within the tissue region from the cooling effect of the medical device 100 (e.g., to provide protection against freezing).

In some non-limiting examples, the medical device 100 may be configured to operate with a spatially varying operating temperature along the base 102. For example, the base 102 may define a symmetrical operating temperature profile that increases in temperature from a centerline of the base 102 to first and second edges of the base 102. In some non-limiting examples, the base 102 may define a symmetrical operating temperature profile that decreases in temperature from a centerline of the base 102 to first and second edges of the base 102. In some non-limiting examples, the base 102 may define a varied operating temperature profile that conforms to any functional form, as desired.

Figure 9:
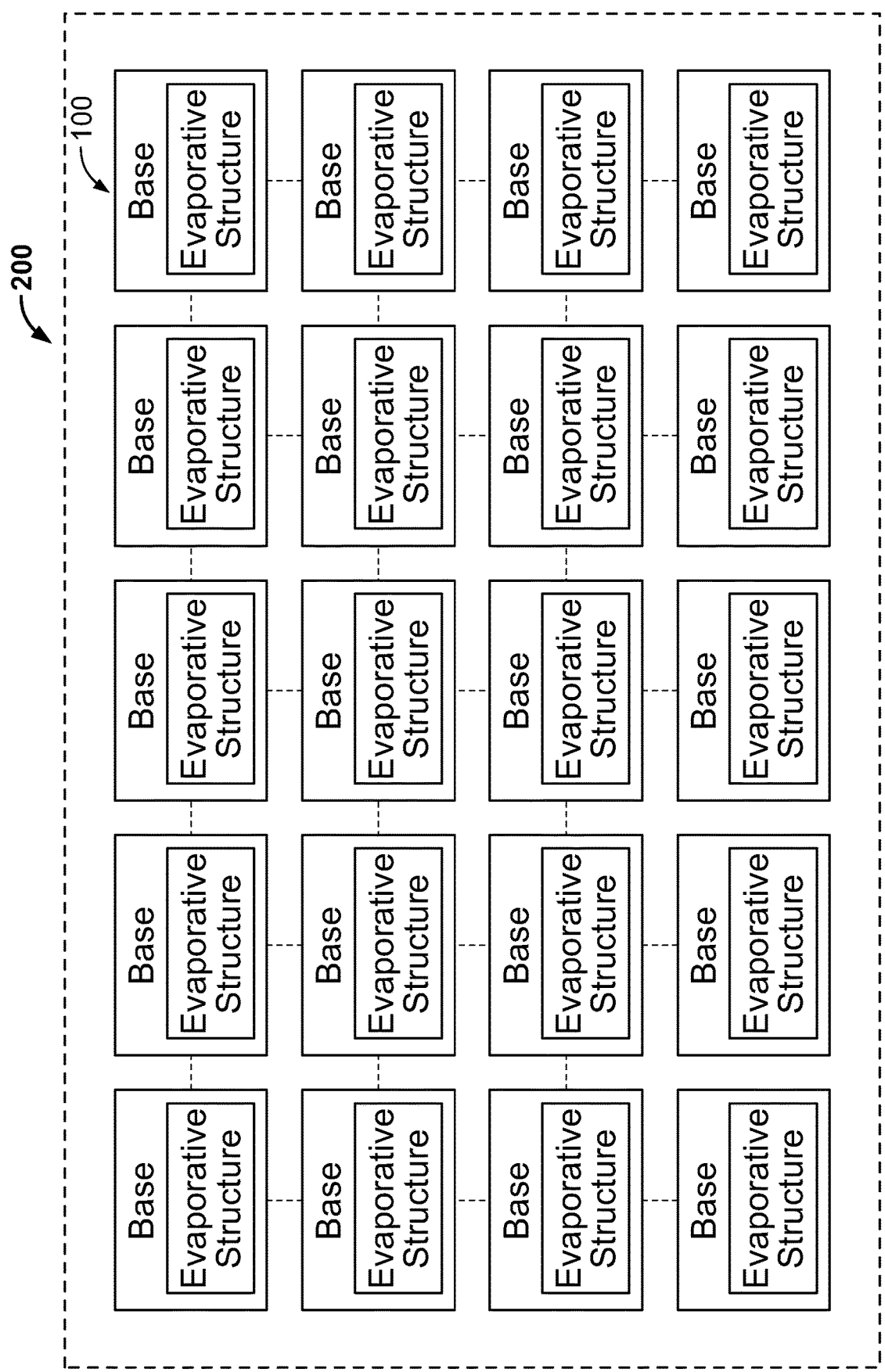
FIG. 9 is a schematic illustration of a tiled medical device according to one aspect of the present disclosure.

FIG. 9 illustrates a non-limiting example of a tiled medical device 200 according to one aspect of the present disclosure. As illustrated in FIG. 9, the tiled medical device 200 may include a plurality of the medical devices 100 arranged in an array, or tiled, pattern. It should be appreciated that the medical devices 100 may be arranged in any pattern as desired. In some non-limiting examples, the medical devices 100 may be linked via a mesh-like structure. In other non-limiting examples, the medical devices 100 may be individually mounted to an external structure. In any case, the medical devices 100 may be moveable to enable the tiled medical device 200 to conform to any anatomical region and/or to match any anatomical features, as desired. In some non-limiting examples, the medical devices 100 may be individually controlled within the tiled medical device 200 to enable the tiled medical device 200 to provide a predetermined cooling pattern. For example, the medical devices 100 may be provided with various working fluids to define different operating temperatures. Alternatively or additionally, the evaporative structures 104 within the medical devices 100 may be designed to provide different heat transfer properties. Alternatively or additionally, the bases 102 of the medical devices 100 may be coated and/or insulated to control the output temperature thereof. In some non-limiting examples, selective groups of the medical devices 100 within the tiled medical device 200 may be controlled to enable the tiled medical device 200 to provide a predetermined cooling pattern. For example, selective groups of the medical devices 100 within the tiled medical device 200 may be connected to different working fluid circuits, which enable the selective groups of the medical devices 100 to operate at different cooling temperatures.

It should be appreciated that the various non-limiting examples of the medical device 100 described herein are not necessarily separate in nature, and the medical device 100 may be adapted to include any combination of the various non-limiting components and configurations described herein.

Figure 10:
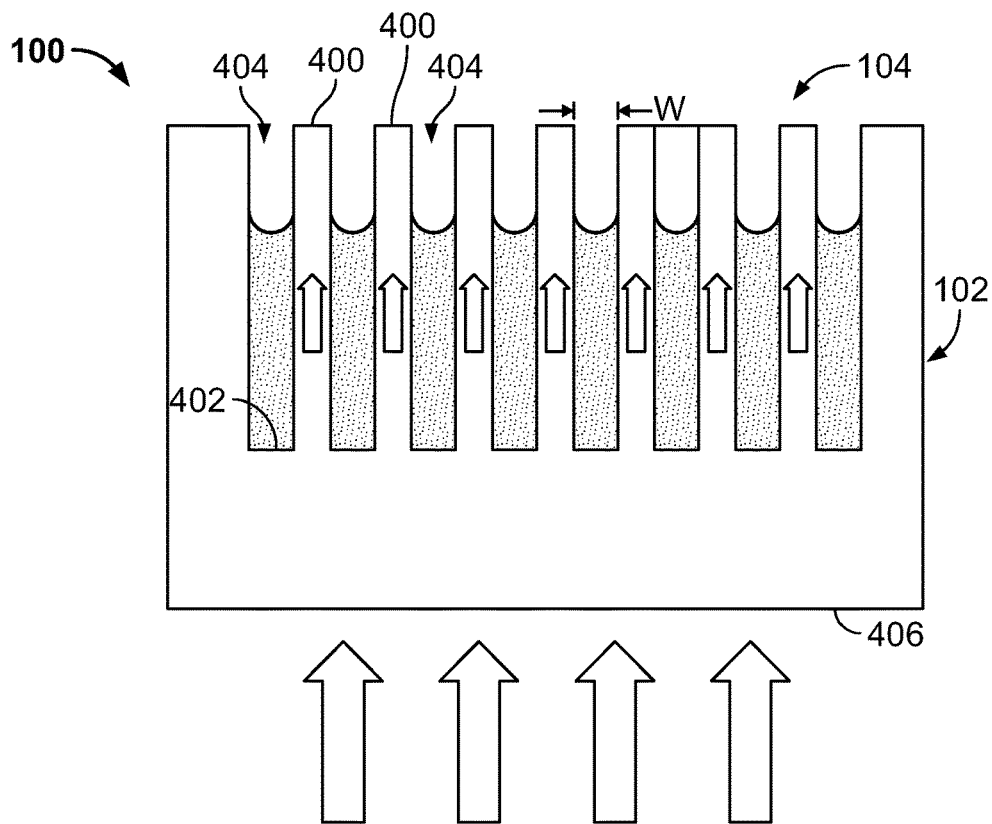
FIG. 10 is a schematic illustration of a medical device including a plurality of channels according to one aspect of the present disclosure.

FIG. 10 illustrates one non-limiting example of the evaporative structure 104 according to one aspect of the present disclosure. In the non-limiting example of FIG. 10, the evaporative structure 104 is integrated into the base 102. The base 102 includes a plurality of fins 400 that extend from a first surface 402 of the base 102 to form a plurality of channels 404 therebetween. The channels 404 are configured to receive the working fluid and are dimensioned to ensure that liquid menisci are formed therein. During operation, for example, a second surface 406 of the base 102 may be brought into engagement with a tissue region. Heat energy from the tissue region may travel through the base 102 and the fins 400 to the liquid menisci formed in the channels 404 where the working fluid is evaporated. The integral effect of evaporation from all the menisci in the evaporative structure 104 provides the substantial heat removal capacity of the medical device 100. The properties of the evaporative structure 104 may affect the rate of evaporation and thereby the overall heat removal capacity of the medical device 100. For example, the number of channels 404, the channel width W, the material of the base 102, a coating applied to the base 102, and a material applied to the exterior of the base 102 (i.e., between the base 102 and the tissue region) may all affect the overall cooling performance of the medical device 100.

Figure 11:
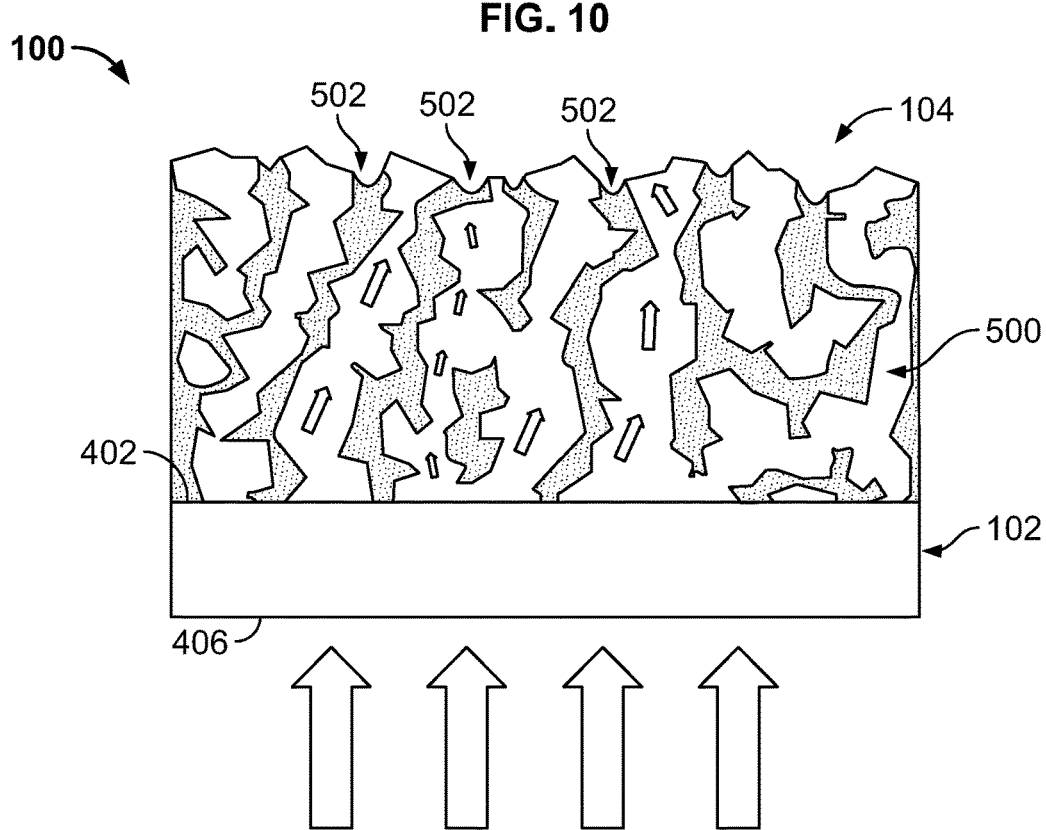
FIG. 11 is a schematic illustration of a medical device include a porous substrate according to one aspect of the present disclosure.

FIG. 11 illustrates another non-limiting example of the evaporative structure 104 according to the present disclosure. As shown in FIG. 11, the evaporative structure 104 may be formed by a porous substrate 500. In some non-limiting examples, the porous substrate 500 may be attached to, or removably positioned, on the first surface 402 of the base 102. In some non-limiting examples, the porous substrate 500 may be attached to the first surface 402 of the base 102. In any case, the porous substrate 500 includes a plurality of pores 502 that each act as sites to form menisci, once filled with the working fluid. During operation, for example, the second surface 406 of the base 102 may be brought into engagement with a tissue region. Heat energy from the tissue region may travel through the base 102 and the porous substrate 500 to the liquid menisci where the working fluid is evaporated. The properties of the porous substrate 500 may affect the rate of evaporation and thereby the overall heat removal capacity of the medical device 100. For example, the number of pores 502, the size of the pores 502, the material of the porous substrate 500, the material of the base 102, a material applied to the exterior of the base 102 (i.e., between the base 102 and the tissue region), and a coating applied to the base 102 may all affect the overall cooling performance of the medical device 100.

Figure 12:
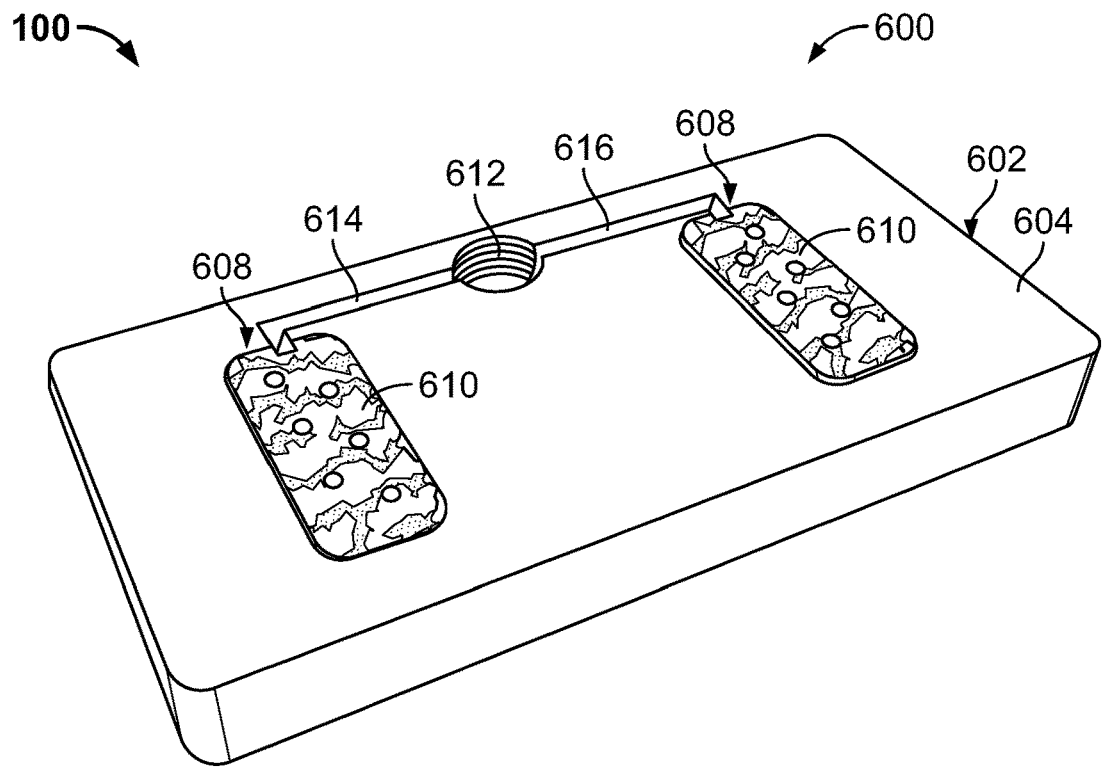
FIG. 12 is a top, front, right isometric view of a noninvasive medical device with an open circuit according to one aspect of the present disclosure.
Figure 13:
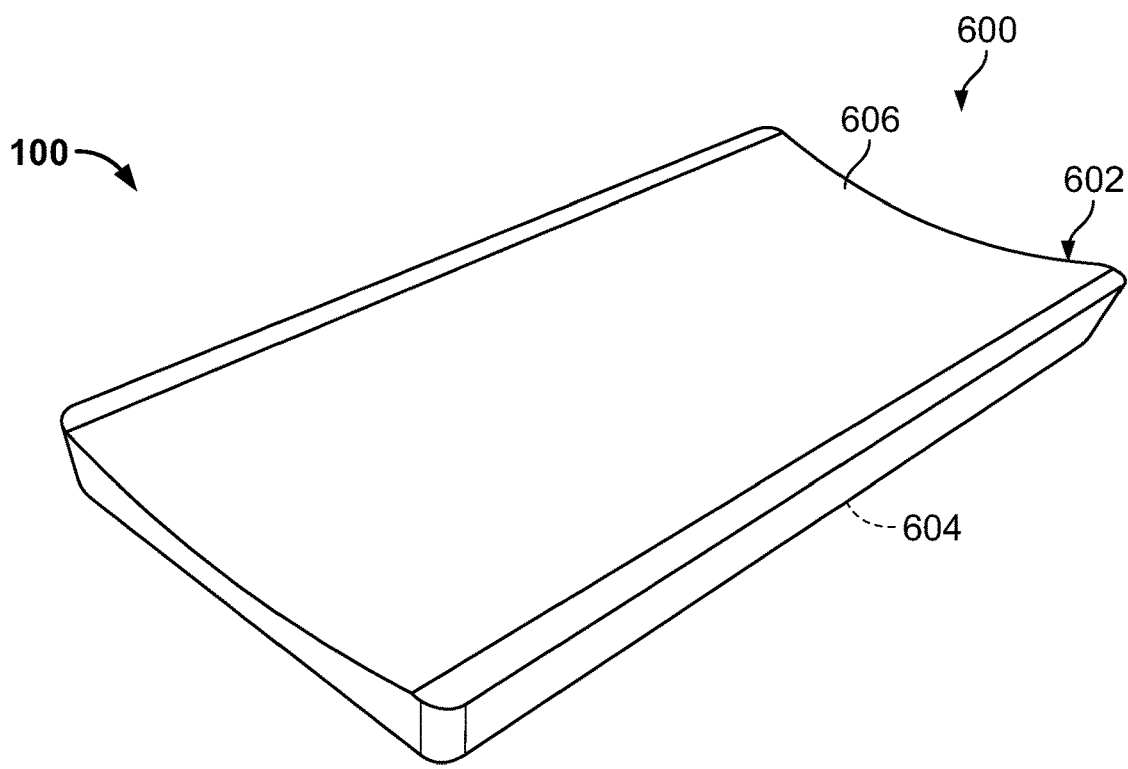
FIG. 13 is a bottom, back, left isometric view of the noninvasive medical device of FIG. 12.

As described above, the medical device 100 may be in the form of a noninvasive medical device. FIGS. 12 and 13 illustrate one non-limiting example of a noninvasive medical device 600 configured to cool a tissue region via a two-phase heat transfer process in accordance with the systems and methods described herein. The noninvasive medical device 600 includes a base 602 having a first surface 604, a treatment surface 606 arranged opposite to the first surface 604, and a cooling cavity 608 formed in the base 602. In some non-limiting examples, the base 602 may be fabricated from a metal material (e.g., aluminum, copper, brass, etc.). In some non-limiting examples, the base 602 may be fabricated from a graphite or woven material (e.g., carbon fiber).

In the illustrated non-limiting example, the base 602 includes two cooling cavities 608. In other non-limiting examples, the base 602 may include more or less than two cooling cavities 608. The cooling cavities 608 are formed by recesses that extend into the first surface 604 toward the treatment surface 606. In the illustrated non-limiting example, the cooling cavities 608 define a generally rectangular shape. In other non-limiting examples, the cooling cavities 608 may define another shape (e.g., round, polygonal, etc.), as desired.

The cooling cavities 608 are configured to receive a porous substrate 610 therein. In some non-limiting examples, the porous substrate 610 may be fabricated from a metal (e.g., aluminum or copper), carbon fiber mesh material, or metal foam material. The porous substrates 610 includes a plurality of pores that each act as sites to form menisci, once filled with the working fluid. As described herein, the menisci may act as sites for the working fluid to evaporate from, in response to heat input from the desired tissue region in contact with the treatment surface 606.

The geometric properties of the porous substrates 610 (e.g., a size of the pores) may be designed such that, once filled with working fluid, capillary forces maintain the working fluid therein regardless of the orientation of the noninvasive medical device 600. That is, the capillary forces within the porous substrates 610, once filled, may be greater than the force of gravity enabling the noninvasive medical device 600 to be used in any orientation without the threat of leakage of the working fluid.

The porous substrates 610 may be in engagement with at least a portion of the base 602. In the illustrated non-limiting example, one or more posts 611 protrude upward from the bottom surface of the cooling cavities 608 to enhance contact between the base 602 and the porous substrates 610. The posts 611 may be arranged throughout the cooling cavities 608 to aid the conductive heat transfer between the porous substrates 610 and the base 602. In the illustrated non-limiting example, each of the cooling cavities 608 include six posts 611 staggered therealong. In other non-limiting examples, each of the cooling cavities 608 may include more or less than six posts 611 arranged in any pattern, as desired.

In the illustrated non-limiting example, the porous substrates 610 may be exposed to the surroundings (i.e., the noninvasive medical device 600 defines an open circuit with respect to the working fluid). This may allow the working fluid arranged within the porous substrates 610 to evaporate to the surroundings. In these non-limiting examples, the working fluid may be chosen to be chemically inert and/or safe for inhalation by the patient and/or the user. In some non-limiting examples, the porous substrates 610 may be pre-loaded with the working fluid. In some non-limiting examples, the porous substrates 610 may be quasi-open where porous substrates 610 are covered by a structure, which is exposed to the surroundings. The evaporated working fluid may travel along the structure and subsequently condense therein to enable at least a portion of the working fluid to be collected and recirculated, as desired. In some non-limiting examples, the porous substrates 610 may be sealed from the surroundings to provide a closed circuit for the working fluid. That is, the working fluid may be provided to the noninvasive medical device 600 from a sealed reservoir, and the evaporated working fluid may be captured from the sealed cooling cavities 608 and subsequently condensed either actively (e.g., via a condenser) or passively (e.g., via heat transfer with the surroundings). The condensed working fluid may be fluidly communicated back to the sealed reservoir. Thus, in the closed circuit, the working fluid may not be exposed to the surroundings thereby enabling the use of chemically active working fluids that may be potentially harmful in an open circuit.

The cooling cavities 608 and thereby the porous substrates 610 are connected to a port 612 via first and second channels 614 and 616. The port 612 and the first and second channels 614 and 616 are recessed into the first surface 604. During operation, the port 612 may be configured to be connected to a supply of working fluid. The working fluid may flow from the port 612 along the channels 614 and 616 to the cooling cavities 608 and into the porous substrates 610.

In some non-limiting examples, a disposable charged cartridge (not shown) may be provided to control a pressure of the working fluid within the noninvasive medical device 600. For example, the charged cartridge may be in fluid communication with the working fluid upstream of the cooling cavities 608, and configured to selectively increase a pressure of the working fluid flowing into the cooling cavities 608. Alternatively or additionally, the charged cartridge may be in fluid communication with the noninvasive medical device 600 downstream of the cooling cavities 608, for example, to effectuate condensation of the working fluid.

During operation of the closed circuit configuration of the noninvasive medical device 600, for example, a working fluid may be supplied to the noninvasive medical device 600 to fill the porous cavities 608. In some non-limiting examples, the capillary forces provided by the design of the porous substrates 610 may cause the working fluid to flow therein without the requirement of an externally induced pressure differential. Thus, working fluid may be supplied to the port 612 and the working fluid may be naturally (i.e., without external forces) drawn into the porous substrates 610.

Once the porous substrates 610 are filled with the working fluid, the noninvasive medical device 600 may be positioned such that the treatment surface 606 engages a desired tissue region of a patient. The engagement of the treatment surface 606 with the desired tissue region initiates heat transfer between the noninvasive medical device 600 and the desired tissue region. Specifically, heat from the desired tissue region transfers through the treatment surface 606 and to a bottom surface of the cooling cavities 608. From the bottom surface of the cooling cavities 608, the heat transfers through the porous substrates 610 to the liquid menisci where evaporation of the working fluid due to the heat input from the tissue region. The integral effect of evaporation from all the menisci in the porous substrates 610 provides the noninvasive medical device 600 with substantial heat removal capacity (i.e., heat flux capacity) when compared to conventional medical cooling technologies.

Figure 14A:
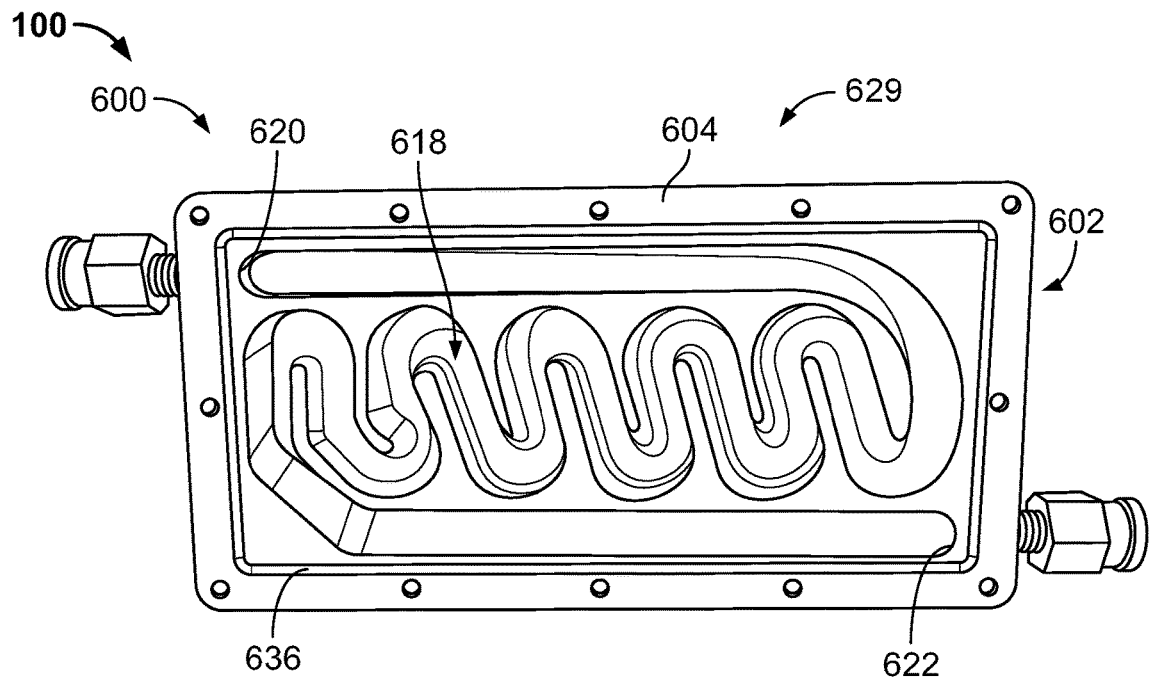
FIG. 14A is a top view of a condenser side of a noninvasive medical device with a closed circuit according to one aspect of the present disclosure.
Figure 14B:
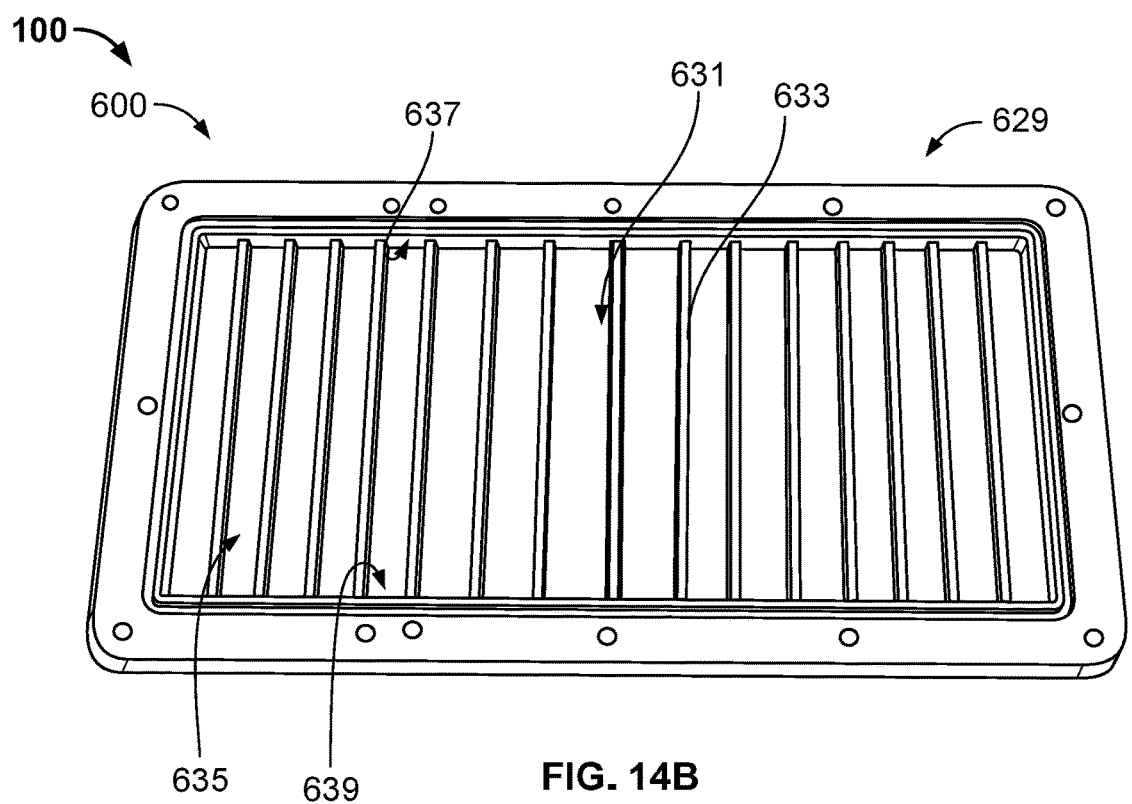
FIG. 14B is a bottom view of the condenser side of the noninvasive medical device of FIG. 14A.
Figure 15:
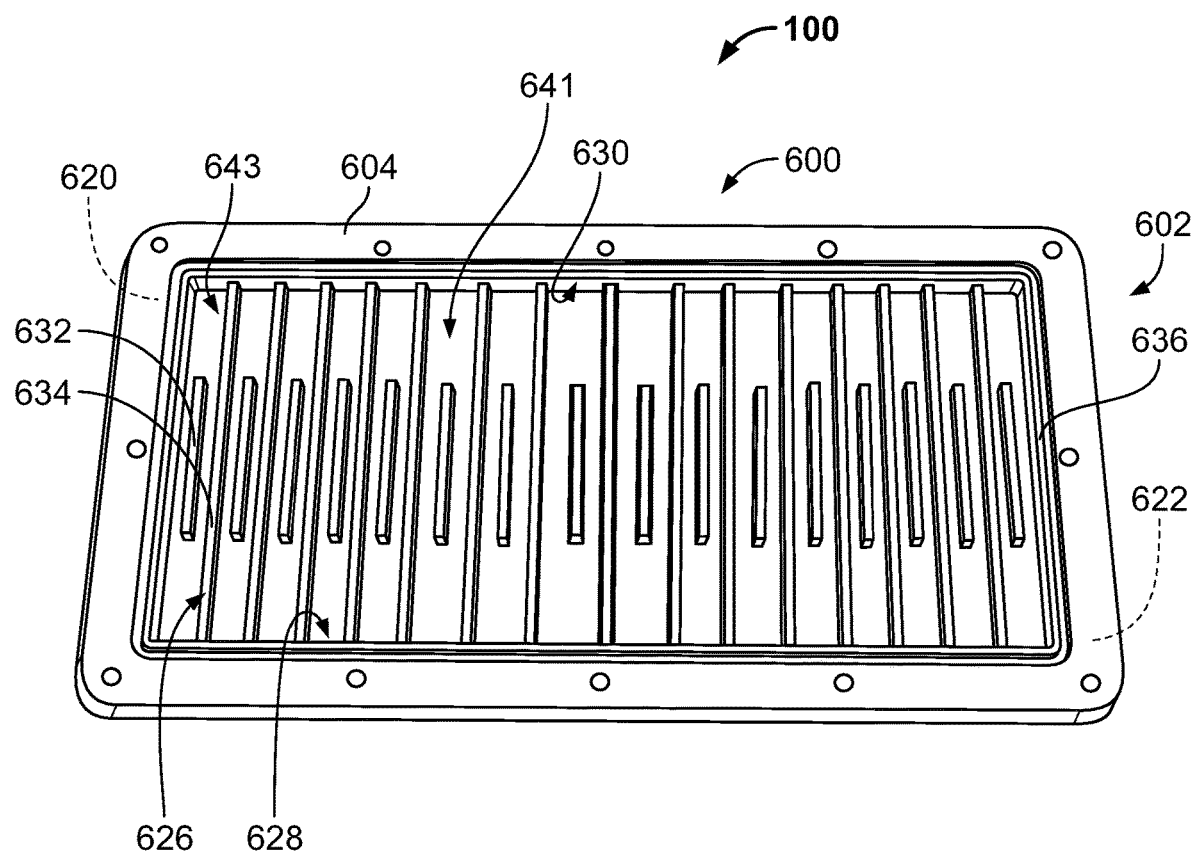
FIG. 15 is a top, front view of an evaporative side of the noninvasive medical device of FIG. 14A.

As described above, in some non-limiting examples, the noninvasive medical device 600 may define a closed circuit with respect to the working fluid. FIGS. 14A-15 illustrate a illustrate non-limiting example of the noninvasive medical device 600 that implements a closed circuit with respect to the working fluid. As illustrated in FIGS. 14A and 14B, the noninvasive medical device 600 may include a condensing plate 629 and defines a flow path 618 on one side thereof and a condensing structure 631 on another side thereof. The flow plat 618 extends from an inlet port 620 to an outlet port 622. The flow path 618 may be recessed into one side of the condenser plate 629 and define a shape that covers a desired amount of the surface area of the base 602. In the illustrated non-limiting example of FIG. 14A, the flow path 618 extends from the inlet port 620 in a generally straight path toward an opposing end of the condensing plate 629 and, adjacent to the opposing end of the condensing plate 629, the flow path 618 curves in a direction toward a center of the condensing plate 629. The flow path 618 then extends in a direction back toward the end of the condensing plate 629 on which the inlet port 620 is arranged in a generally swirl-like pattern. That is, the flow path 618 curves back and forth as it extends toward the inlet end of the base 602. Once the swirl section of the flow path 618 reaches the inlet end of the condensing plate 629, the flow path 618 curves in a curves in a direction away from the inlet port 620 and extends in a generally straight path to the outlet port 622.

It is to be appreciated that the illustrated flow path 618 is but one non-limiting example and that the flow path 618 may be shaped to cover a desired amount of the condensing plate, as desired. For example, the flow path 618 may be shaped to uniformly cover a substantial amount of the total surface area of the condensing plate 629. In other non-limiting examples, the flow path 618 may be shaped to cover a selected section of the surface area of the condensing plate 629 where cooling is desired.

As illustrated in FIG. 14B, the other side of the condensing plate 629 include the condensing structure 631. In the illustrated non-limiting example, the condensing structure 631 includes a plurality of ridges 633 arranged along a recessed surface 635. The plurality of ridges 633 protrude outwardly from the recessed surface 635 and extend in a lateral direction between first and second ends 637 and 639 of the condensing plate 629. In some non-limiting example, the plurality of ridges 633 may act as fins to promote addition heat transfer from the fluid flowing through the flow path 618, which acts to aid in condensing of evaporated working fluid, as will be described.

FIG. 15 illustrates a evaporative plate 641 of the noninvasive medical device 600 with a closed circuit. As illustrated in FIG. 15, the evaporative plate 641 includes an evaporative structure 624 arranged on a side thereof opposite to the treatment surface 606. In the illustrated non-limiting example, the evaporative structure 624 may include a plurality of ridges 626 that protrude outwardly from a recessed surface 643 in a direction away from the treatment surface 606. The plurality of ridges 626 may extend in a lateral direction between first and second ends 628 and 630 of the recessed surface 624, and may be arranged along the recessed surface 624 between the inlet port 620 and the outlet port 622. In some non-limiting examples, the plurality of ridges 626 may extend varying lateral distances between the first and second ends 628 and 630. For example, the plurality of ridges 626 may alternate between a first ridge 632 and a second ridge 634 between the inlet port 620 and the outlet port 622. The first ridge 632 may extend from a center of the recessed surface 624 to a location between the center and each of the first and second ends 628 and 630 (i.e., the first ridge 632 does not extend completely between the first and second ends 628 and 630). The second ridge 634 may extend completely between the first and second ends 628 and 630. In some non-limiting examples, a distance between adjacent ridges 632 and 634 may ensure that capillary forces maintain the working fluid therebetween. Therefore, the different lateral extensions between the first ridge 632 and the second ridge 634 may maintain the working fluid along a centerline of the evaporative plate 641. In other non-limiting examples, the design of the evaporative structure 641 may be altered to accommodate any desired cooling pattern, for example, by manipulating the arrangement and orientation of the ridges 632, 634. In some non-limiting examples, the evaporative structure 641 may be in the form of a porous structure, as described herein. In some non-limiting examples, the evaporative structure 641 may be in the form of one or more microchannels that extend along the recessed surface 624.

Both of the condenser plate 629 and the evaporative plate 641 may include a recessed notch 636 that extends therein and surrounds the flow path 618, the condensing structure 631, and the evaporative structure 624. The recessed notches 636 may be configured to receive a seal (e.g., an o-ring or gasket) therein to facilitate forming a seal between a cover plate attached to the each of the sides of the condenser plate 629 and the non-treatment side of the evaporative plate 641.

Figure 16:
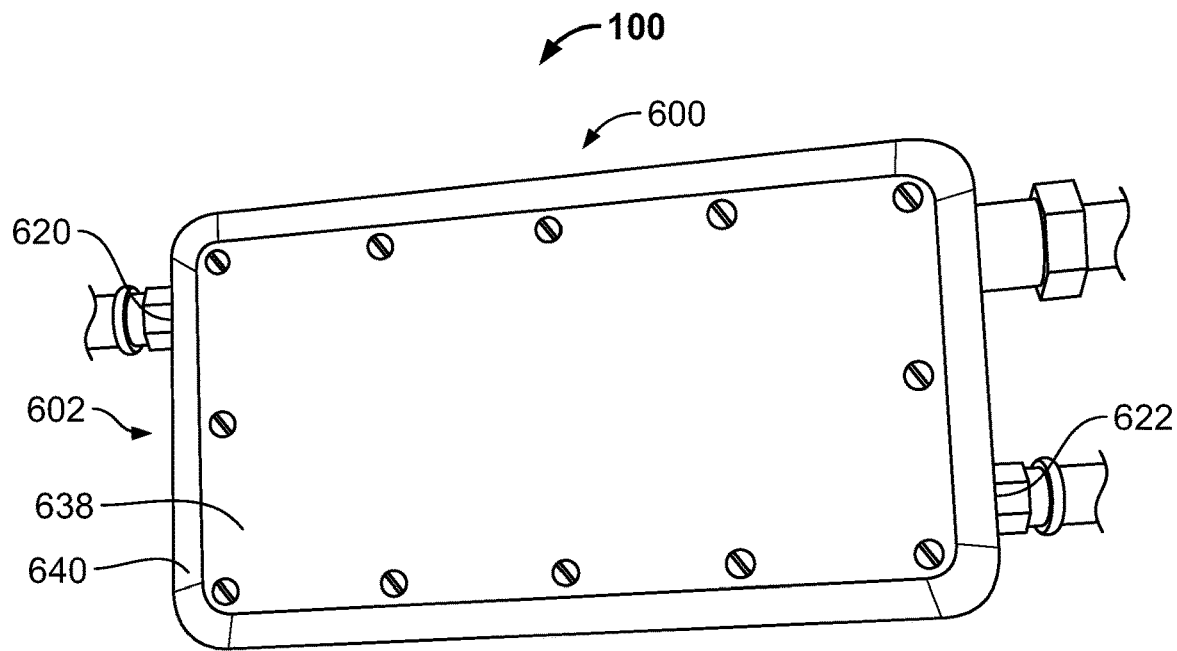
FIG. 16 is a top view of the noninvasive medical device of FIG. 14A, when assembled.
Figure 17:
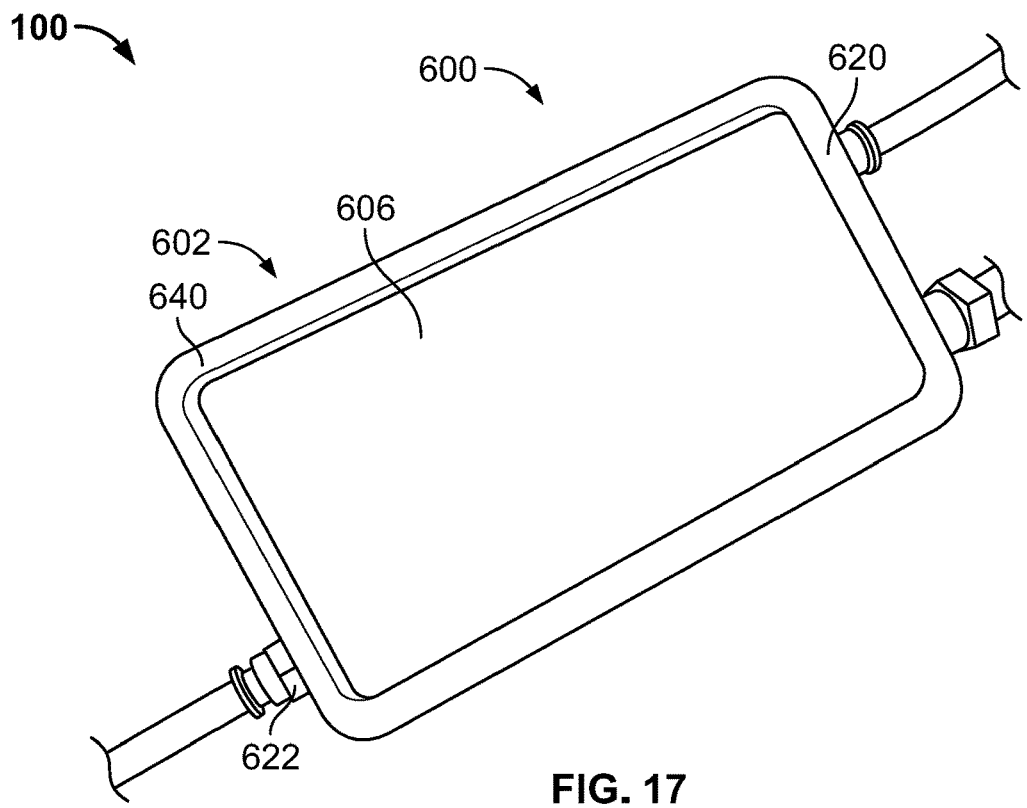
FIG. 17 is a bottom view of the noninvasive medical device of FIG. 14A, when assembled.

As illustrated in FIGS. 16 and 17, the noninvasive medical device 600 may, when assembled, include an insulated layer 640 arranged around a periphery thereof. In some non-limiting examples, the insulated layer 640 may aid in inhibiting heat from dissipating from the noninvasive medical device 600 to the atmosphere, and may provide protection for a user manipulating the noninvasive medical device 600. Additionally, the noninvasive medical device 600 may include a charging port that enables the working fluid to be charged into the device (i.e., flow into the area between the evaporative structure 641 and the condensing structure 631. When assembled, the condenser plate 629 may be attached to the condenser plate 641 such that the evaporative structure 624 faces the condensing structure 631. Thus, when assembled, one side of the device includes the treatment surface 606, which is thermally coupled to the evaporative structure 624, and a cover plate may be arranged on the other side, which covers the flow path 618.

During operation of the closed circuit configuration of the noninvasive medical device 600, for example, working fluid may be charged into a cavity formed between the evaporative structure 624 and the condensing structure 631. Once charged, this cavity may be sealed off, thereby closing the working fluid off from the surroundings. When the treatment surface 606 is placed in contact with a desired tissue region, heat transfer initiates between the desired tissue region and the evaporative structure 624. Specifically, heat from the desired tissue region transfers through the treatment surface 606 and to the working fluid flowing within the evaporative structure 624. The heat input from the desired tissue region facilitates the evaporation of the working fluid which can come into contact with the condensing structure 631. Evaporation of the working fluid flowing within the evaporative structure 624 enables the noninvasive medical device 600 to leverage the advantages of two-phase heat transfer processes described herein. Thus, the noninvasive medical device 600 provides substantial heat removal capacity (i.e., heat flux capacity) when compared to conventional medical cooling technologies.

During operation of the device, cooling fluid may be flown through the flow path 618, which is isolated from the working fluid. Thus, as the evaporated working fluid builds up around the condensing structure 631, the cooling provided by the fluid flowing through the flow path 618 may provide the necessary heat removal to facilitate condensing of the evaporated working fluid and result in the condensed working fluid "raining down" onto the evaporative structure 624.

Figure 18:
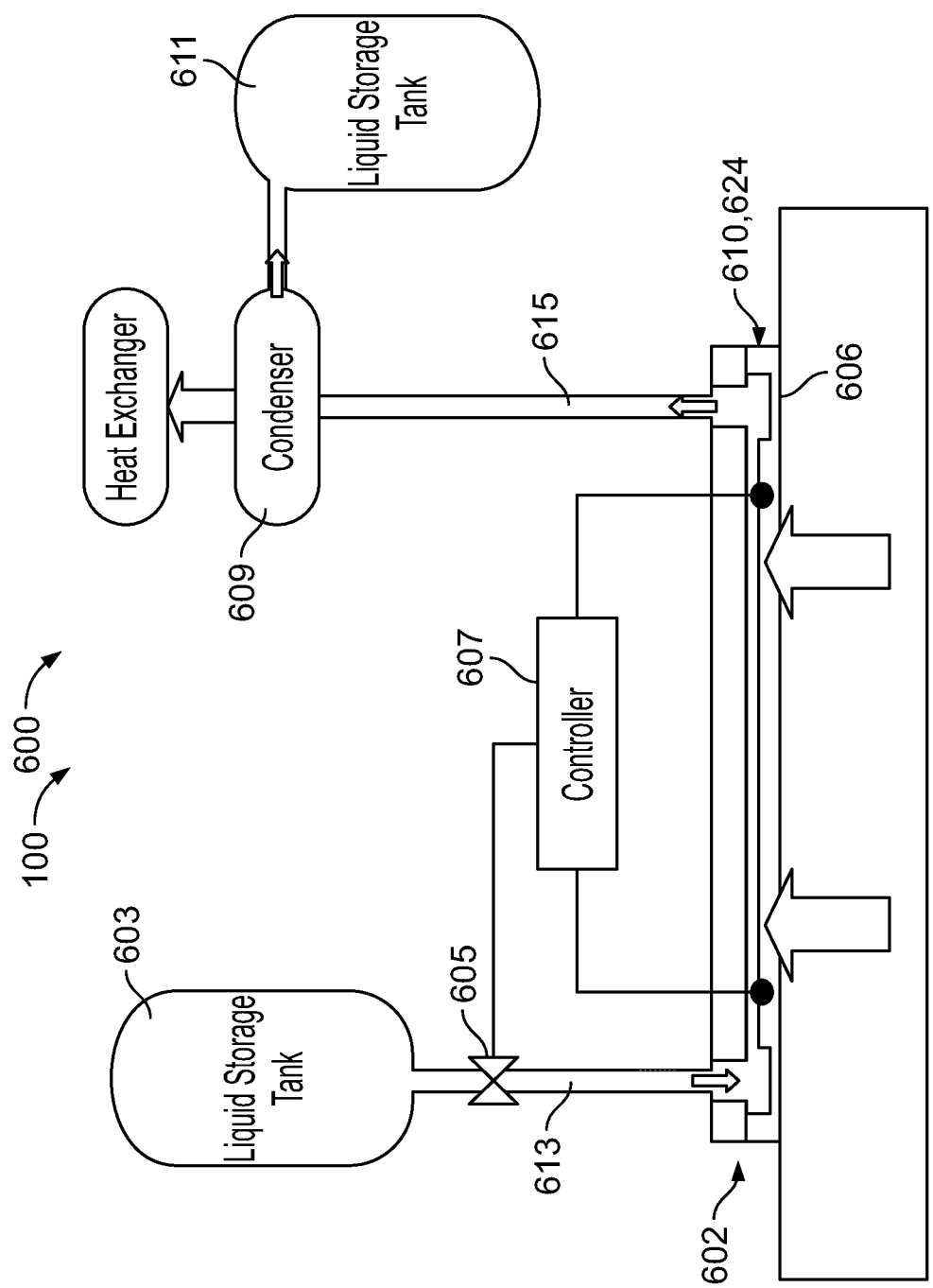
FIG. 18 is a schematic illustration of a non-invasive medical device with an evaporator applied to a tissue region that draws fluid from a liquid storage tank.
Figure 19:
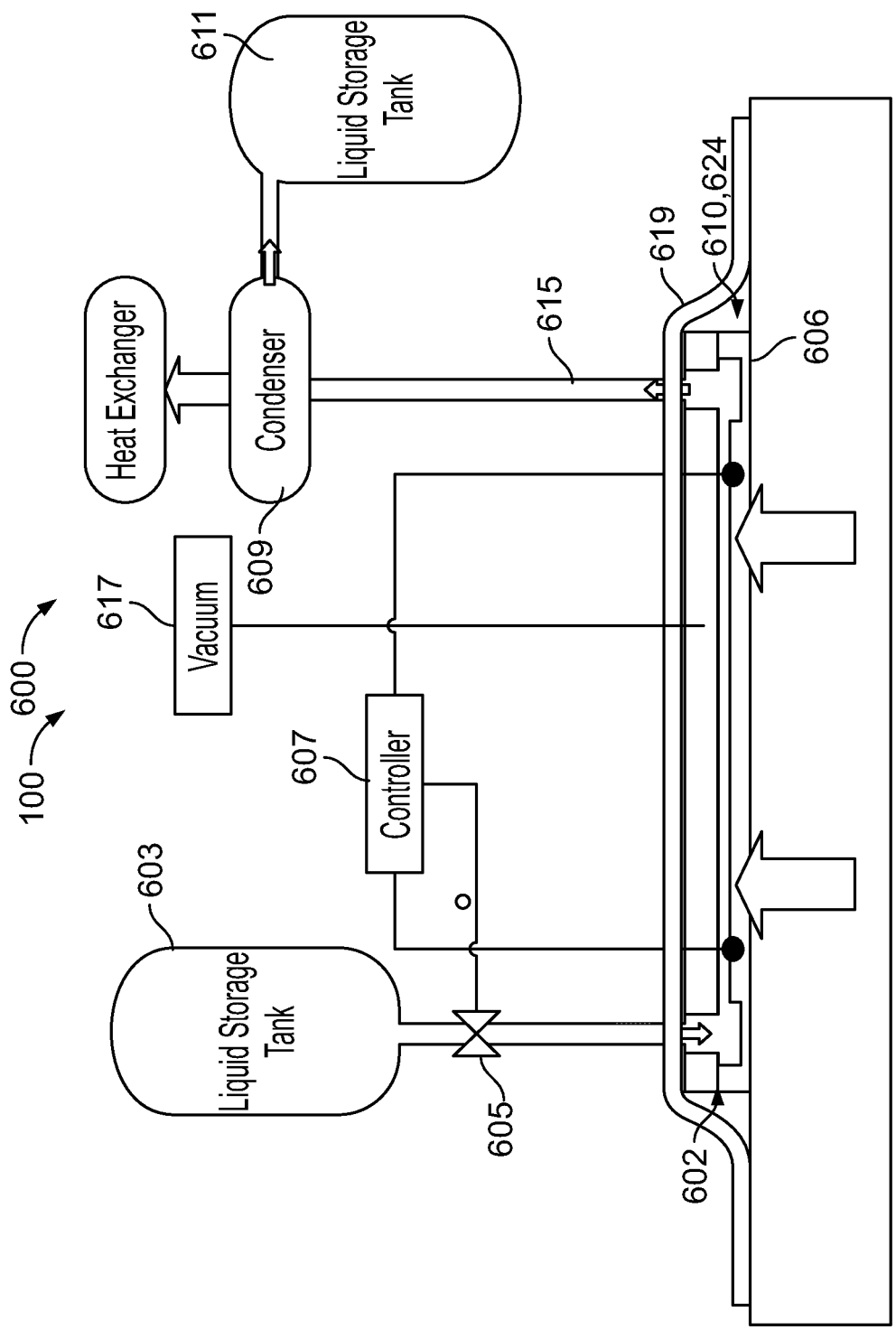
FIG. 19 is a schematic illustration of the non-invasive medical device of FIG. 18 with a flexible cover and a vacuum.

FIG. 18 another non-limiting example of the noninvasive medical device 600 implemented in a thermal treatment application. As illustrated in FIG. 18, the noninvasive medical device 600 may define an open system with respect to the working fluid (i.e., the working fluid is provided to the device and recovered from the device) and the device does not include a condensing stage within the base 602 (i.e., the condensing stage happens remotely from the base 602, which is in contact with the tissue region). The noninvasive medical device 600 may be configured to receive working fluid from a tank 603. A inlet line 613 extends between the tank 603 and an inlet to the evaporative structure 610, 624 to provide fluid communication therebetween. A flow control device 110, 605 may be arranged on the inlet line 613 between the tank 603 and the inlet to the evaporative structure 610, 624 In some non-limiting examples, the flow control device 110, 605 may be configured to control a direction of fluid flow, a pressure of fluid flow, and/or a flow rate. From the inlet to the evaporative structure 610, 624, the working fluid can flow along the evaporative structure 624 and remove heat from the tissue region, which results in evaporation of the working fluid. Thus, the noninvasive medical device 600 provides substantial heat removal capacity (i.e., heat flux capacity) when compared to conventional medical cooling technologies.

The evaporated working fluid may flow through an outlet to the evaporative structure 610, 624 and into an outlet line 615. From the outlet line 615, the evaporated working fluid may be condensed in a condenser 609 and subsequently stored in a tank 611.

In the illustrated non-limiting example, a controller 607 is in communication with one or more temperature sensors arranged to measure temperature adjacent to or on a surface of the desired tissue region. The controller 607 may instruct the flow control device 110, 605 to adjust the operating parameters of the noninvasive medical device 600 based at least in part on the measurement of the temperature sensors. Several parameters may be used to control the thermal output parameters of the noninvasive cooling 600, as described herein.

In some non-limiting examples, the noninvasive medical deice 600 may be utilized with a flexible blanket 645 that is convers and seals around the noninvasive device 600. A space between the flexible blanket 645 and the noninvasive medical device 600 may be in communication with a vacuum 647 that is configured to reduce a pressure within this space. Due to the form factor of the noninvasive medical device 600 (e.g., thin), the connection to the vacuum 647 may maintain thermal contact between the tissue surface and the treatment surface 606, prevent thermal disturbance from the surroundings (i.e., insulation), suppress blood flow in the tissue region, and accelerate cooling or heating of the target tissue.

Figure 20:
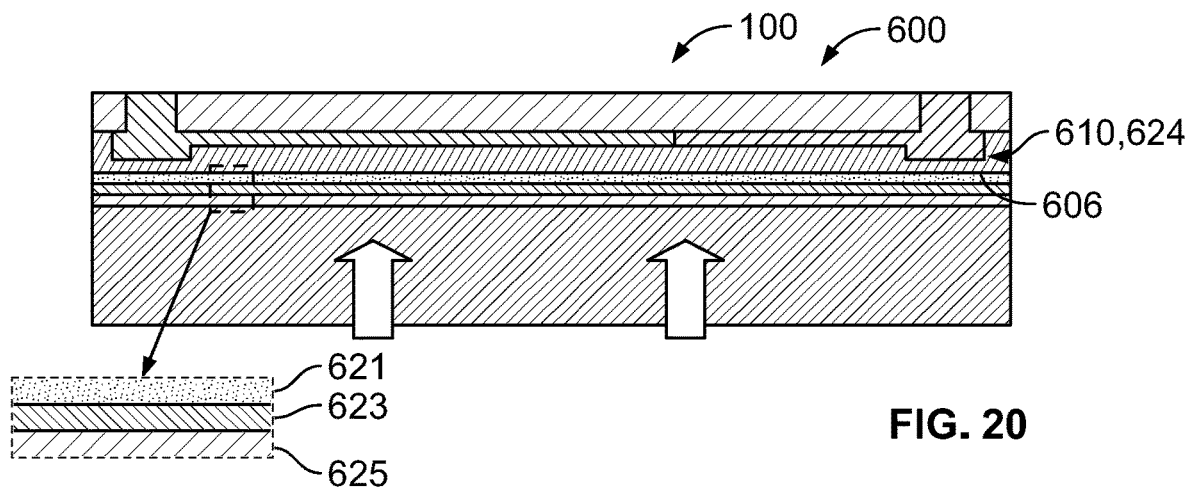
FIG. 20 is a schematic illustration of the non-invasive medical device of FIG. 18 with an adhesive layer, an anti-freeze layer, and a removable sheet applied between the device and a tissue surface.

In some non-limiting examples, as illustrated in FIG. 20, the noninvasive medical device 600 may be provided with an adhesive layer 621 that is adhesively attached to the treatment surface 606. An anti-freeze 623 layer may be provided between the adhesive layer 621 and a removable sheet 625. The anti-freeze layer 623. The removable sheet 625 may be a disposable component that is applied to a desired tissue region and disposed of after a desired medical treatment is performed. In this way, the sterility of the noninvasive medical device 600 may be maintained.

Figure 21:
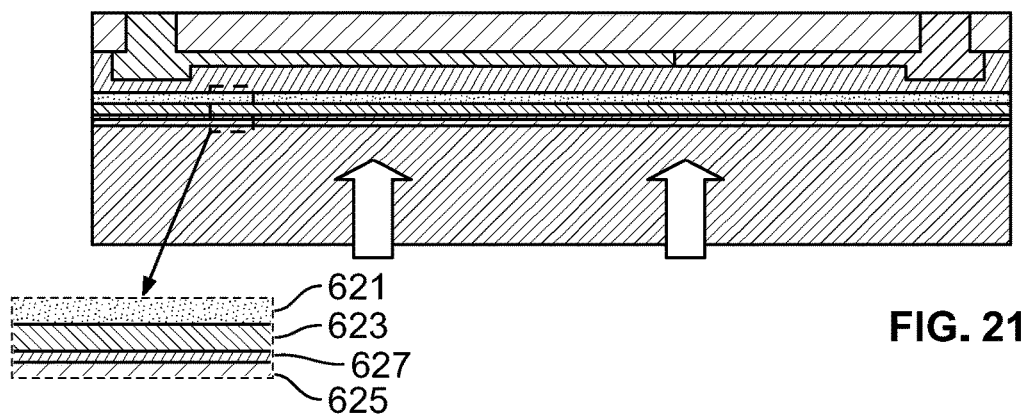
FIG. 21 is a schematic illustration of the non-invasive medical device of FIG. 18 with an adhesive layer, an anti-freeze layer, and a removable sheet applied between the device and a tissue surface where a heater is integrated into the removable sheet.
Figure 22:
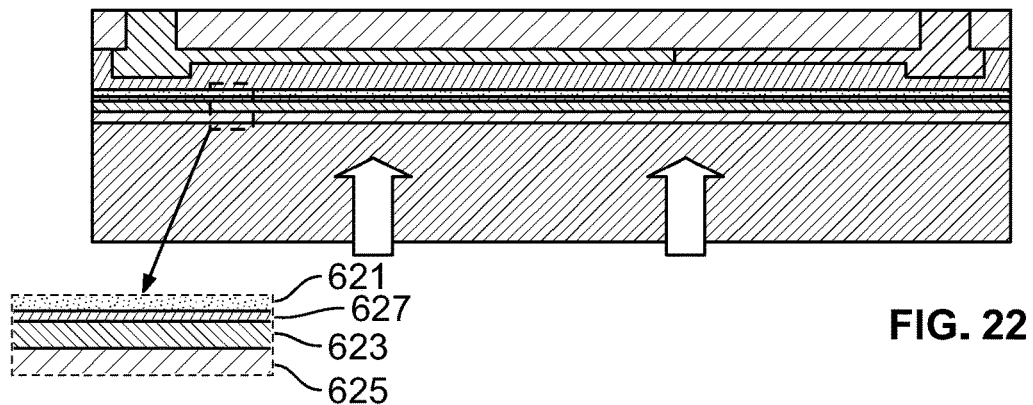
FIG. 22 is a schematic illustration of the non-invasive medical device of FIG. 18 with an adhesive layer, an anti-freeze layer, and a removable sheet applied between the device and a tissue surface where a heater is integrated between the adhesive layer and the anti-freeze layer.

In some non-limiting examples, as illustrated in FIG. 21, a thin heater 627 may be integrated into the removable sheet 625 to melt any frozen sticking between the treatment surface 606 and the tissue surface 606 and enable the detachment of the noninvasive medical device 600 from the tissue surface. In some non-limiting examples, as illustrated in FIG. 22, the thin heater 627 may be not be a disposable component and may be arranged between the adhesive layer 621 and the anti-freeze layer 623.

Figure 23:
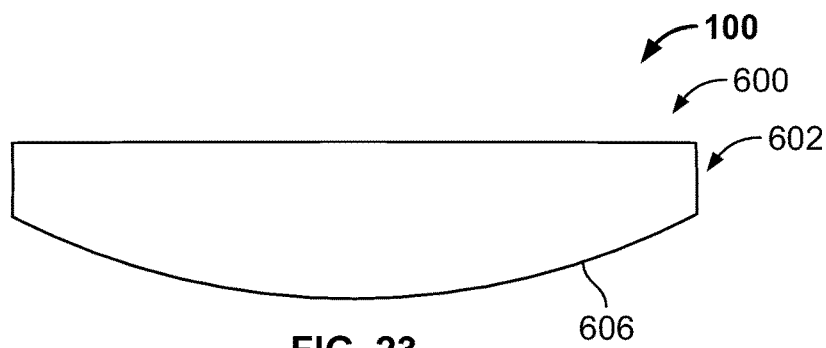
FIG. 23 is a schematic illustration of a concave treatment surface of a noninvasive medical device according to one aspect of the present disclosure.
Figure 24:
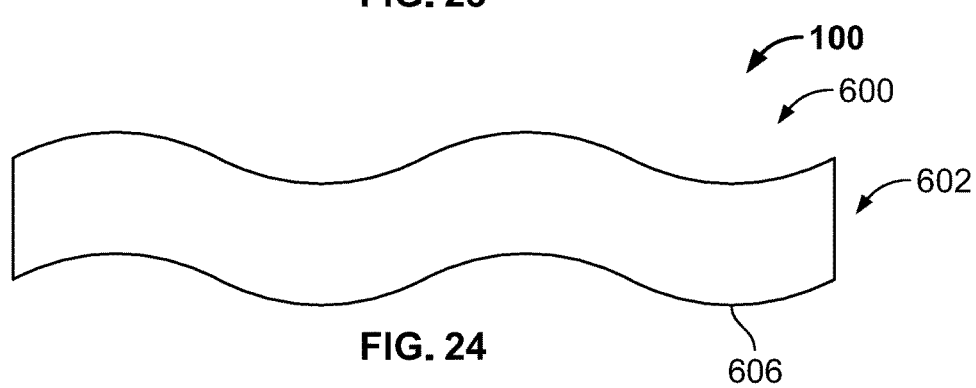
FIG. 24 is a schematic illustration of a treatment surface of a noninvasive medical device having a plurality of peaks and valleys according to one aspect of the present disclosure.
Figure 25:
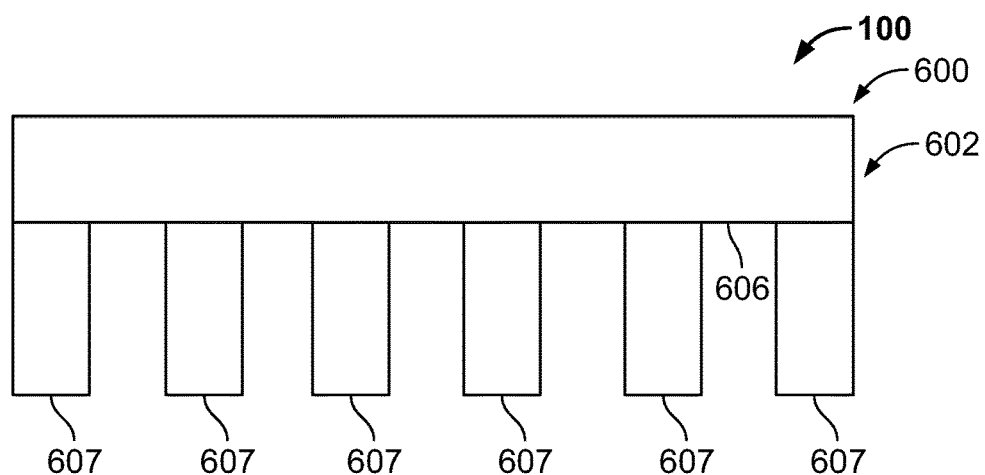
FIG. 25 is a schematic illustration of a treatment surface of a noninvasive medical device having a plurality of protrusions according to one aspect of the present disclosure.

In all of the configurations of the noninvasive medical device 600, the treatment surface 606 may be configured to conform to a specific tissue region on a patient. In some non-limiting examples, the treatment surface 606 may be coated with a coating. The coating applied to the treatment surface 606 may fabricated from a material configured to correspond with the thermophysical properties of the base 602 and/or the working fluid within the porous substrates 610. In the non-limiting example of FIG. 13, the treatment surface 606 defines a generally arcuate or curved surface with a generally rectangular profile. In the non-limiting example of FIG. 17, the treatment surface 606 defines a generally flat surface with a generally rectangular profile. In other non-limiting examples, the treatment surface 606 may define a generally convex shape, as shown in FIG. 23. In some non-limiting examples, the treatment surface 606 may define a generally smooth, or uninterrupted profile. In some non-limiting examples, the treatment surface 606 may define a rough, or interrupted, profile. For example, the treatment surface 606 may include a structural pattern arranged thereon to increase a surface area thereof. FIG. 24 illustrates one non-limiting example of a structural pattern of the treatment surface 606 that includes a plurality of alternating peaks and valleys. FIG. 25 illustrates one non-limiting example of the treatment surface 606 including a plurality of protrusions, or pins, 642 extending therefrom.

Figure 26:
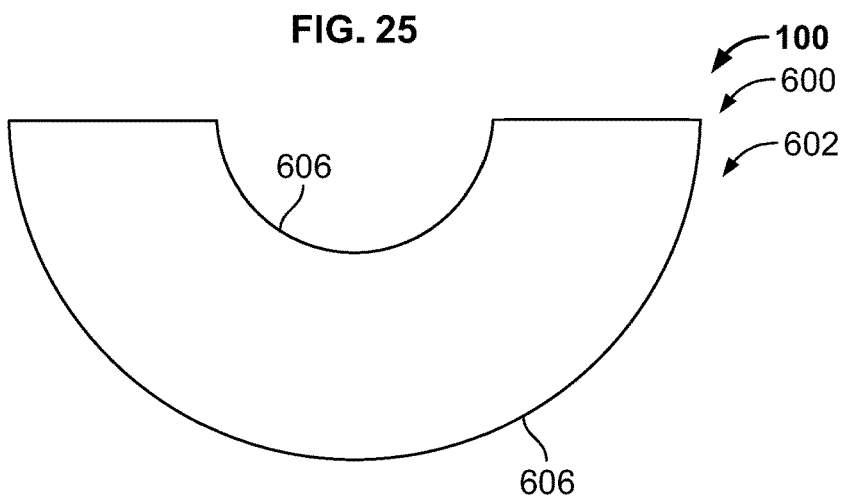
FIG. 26 is a schematic illustration of a horseshoe-shaped treatment surface of a noninvasive medical device according to one aspect of the present disclosure.
Figure 27:
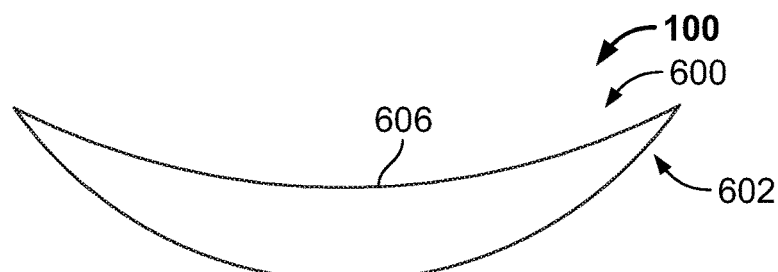
FIG. 27 is a schematic illustration of a crescent moon-shaped treatment surface of a noninvasive medical device according to one aspect of the present disclosure.
Figure 28:
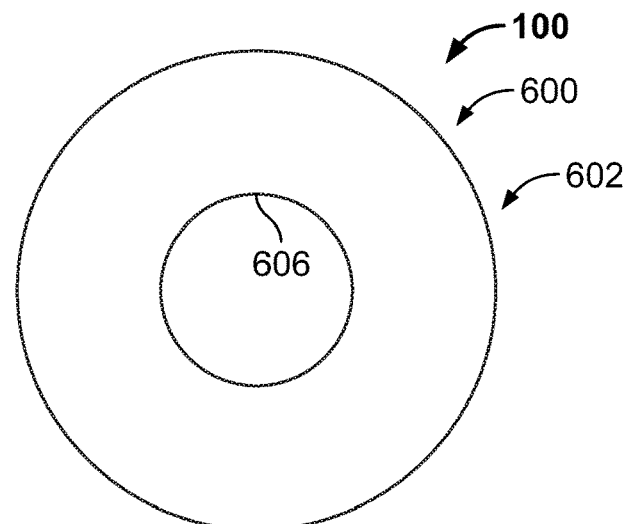
FIG. 28 is a schematic illustration of an annular-shaped treatment surface of a noninvasive medical device according to one aspect of the present disclosure.

In some non-limiting examples, the base 602 or treatment surface 606 may define a generally horseshoe shape, as shown in FIG. 26. In some non-limiting, examples, the base 602 or treatment surface 606 may define a generally banana, or crescent moon, shape, as shown in FIG. 27. In some non-limiting examples, the base 602 or treatment surface 606 may define a generally annular shape, as shown in FIG. 28. In these non-limiting examples, a suction device may be configured to draw a tissue region into a central aperture defined by the base 602.

Figure 29:
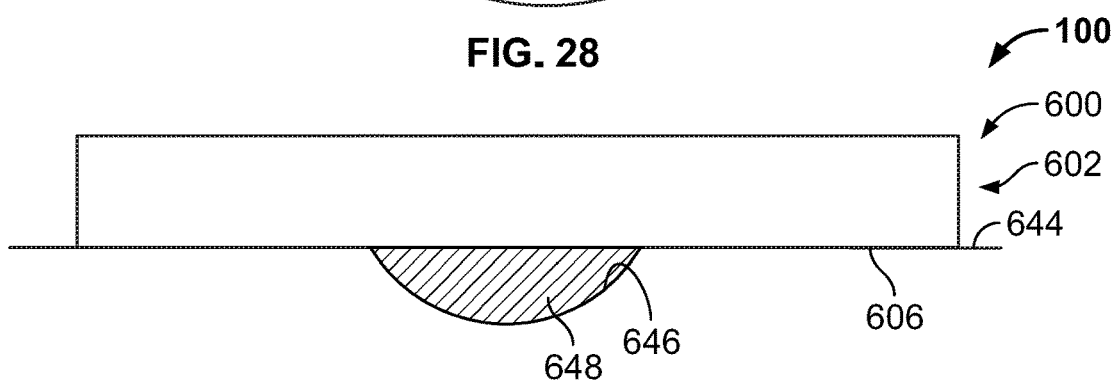
FIG. 29 is a schematic illustration of a noninvasive medical device treating a tissue region having a recess according to one aspect of the present disclosure.

In some non-limiting examples, the noninvasive medical device 600 may be operable to provide cooling to an uneven, or non-uniform, tissue surface. For example, as shown in FIG. 29, a tissue surface 644 may include one or more recesses 646 arranged thereon. In these non-limiting examples, a material (e.g., a gel or foam) 648 may be applied to the tissue surface within the recess 646 to fill the recesses 646. The material may be configured to selectively protect, or insulate, the tissue recesses 646. In some non-limiting examples, the material 648 may define a thermal conductivity that is less than or equal to a thermal conductivity defined by the tissue surface 644 (e.g., skin). By applying the material, for example, to the skin to fill, and insulate, the recesses 646, the treatment surface 606 of the noninvasive medical device 600 may only provide cooling to the areas between, or around, the recesses 646, which contact the treatment surface 606.

Figure 30:
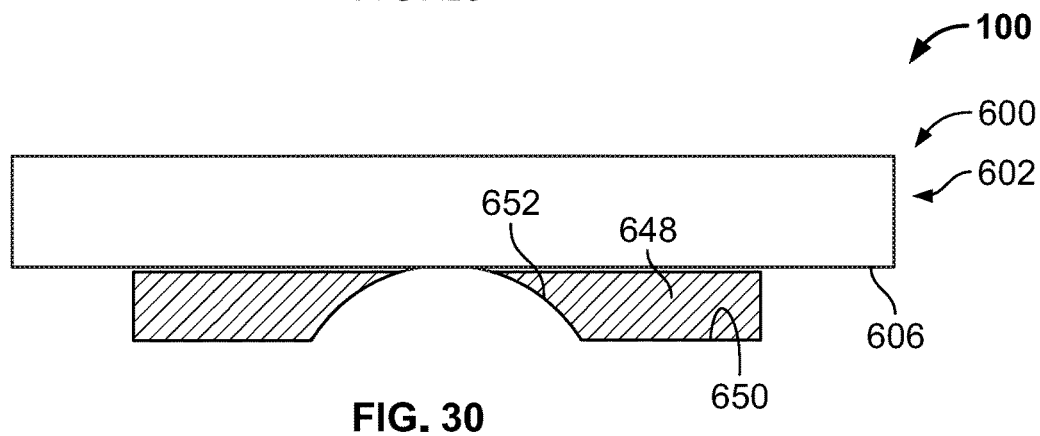
FIG. 30 is a schematic illustration of a noninvasive medical device treating a tissue region having a protrusion according to one aspect of the present disclosure.

In some non-limiting examples, as shown in FIG. 30, a tissue surface 650 may include one or more protrusions 652 arranged thereon. The material (e.g., a gel or foam) 648 may be applied in a pool around the protrusion 652 to selectively protect, or insulate, the tissue surface 650 adjacent to the protrusion 652. By applying the material 648 in a pool around the protrusion 652, the treatment surface 606 of the noninvasive medical device 600 may only provide cooling to the protrusion 652.

In accordance with a non-limiting configuration, the use or method of use of the noninvasive medical device 600 does not include a step of treatment of a human or animal body by surgery or therapy. It is noted that the skills of a person using a device as described herein, may not have the skills of a physician, and that the intended treatment may not be motivated due to illness of the treated person, rather for aesthetic reasons.

Various parameters of the noninvasive medical device 600 may be altered to control the heat removal capacity and operating temperature range based on the application. For example, the material of the base 602, the material of the porous substrates 610, the size of the pores, porosity in the porous substrates 610, the geometry of the fluid path 618, the thermophysical properties of the working fluid, the geometric properties of the cooling cavities 608, etc. Table 2 below provides various non-limiting examples of the properties and operational characteristics of the noninvasive medical device 600.

TABLE 2

Properties and Operating Characteristics of the Noninvasive Medical Device 600

| | |
|---|---|
| Operating Range | −200° C. to 200° C. |
| Operating Pressure | 0.01 bar to 10 bar |
| Working Fluids | Hydrocarbons, Hydrofluorocarbons, Alcohols, Water, Aqueous Solution, Nobel Gases, Binary Mixtures, Nanoparticle laden Fluids |
| Substrate Material | Metals, Polymers, Composite Materials Examples: Copper, Aluminum, Graphite |
| Porous Substrate Material | Aluminum, Copper, Carbon, Steel |
| Porous Substrate Pore Size | 100 nm-2000 μm |
| Coatings | Wetting or non-wetting coating, Gold, Teflon, Anodized Nano-Layers, Nano-structured coatings |
| Fluid Flow Control | Thermo-capillary, Piezo-electric, Expansion Valve, Capillary Tube |
| Temperature Control | Thermocouple, RTD, Embedded Contact Micro-wires |

As described above, the medical device 100 may be in the form of an invasive medical device. FIG. 31 illustrates one non-limiting example of an invasive medical device 700 configured to cool or heat a tissue region via a two-phase heat transfer process in accordance with the systems and methods described herein. In the illustrated non-limiting example, the invasive medical device 700 may be in the form a needle or an arrangement of needles (either fixed or expandable), which may include an introducer (not shown) to control a penetration depth of the invasive medical device 700. In other non-limiting examples, the invasive medical device 700 may be in the form of a catheter based device.

The invasive medical device 700 includes a proximal end 702, a distal end 704, an inner surface 706, and an outer surface 708. The proximal end 702 may be coupled to the introducer (not shown). The distal end 704 includes a needle tip 710 to facilitate penetration into a desired tissue region of a patient. The inner surface 706 includes one or more channels 712 formed therein. In some non-limiting examples, the inner surface 706 may be coated with a material (e.g., a single layer of graphite, or graphene) that possesses a desired surface characteristics such as wetting properties, high surface tension, etc.

The invasive medical device 700 may define an insulated length $L_I$ that may include, for example, an insulated coating to inhibit heat transfer to and from surrounding tissue. The insulated length $L_I$ may be defined at any axial length along the outer surface 708, as desired. In some non-limiting examples, the insulated length $L_I$ may extend axially from the proximal end 702 to a location between the proximal end 702 and the distal end 704 to insulate tissue adjacent to a surface of the desired tissue region.

The invasive medical device 700 may define a thermally active length $L_T$ that is configured to be exposed to the desired tissue region at a desired depth within the tissue region to facilitate cooling of the desired tissue region at the desired depth. The thermally active length $L_T$ may define any length along the outer surface 708, as desired. In some non-limiting examples, the thermally active length may extend axially from the distal end 704 to a location between the distal end 704 and the proximal end 702 to cool tissue below a surface of the desired tissue region.

With specific reference to FIGS. 32-35, the channels 712 are recessed radially into the inner surface 706 and extend axially along the inner surface 706 between the proximal end 702 and the distal end 704. The inner surface 706 defines a generally hollow cavity 714 configured to receive a working fluid therein. During operation, for example, the hollow cavity 714 of the invasive medical device 700 may be filled with a working fluid. The invasive medical device 700 may then be inserted into a desired tissue region to a desired depth within the tissue region. In some non-limiting examples, the axial arrangements of the insulated length $L_I$ and the thermally active length $L_T$ may determine a treatment depth to which the cooling extends within the desired tissue region.

Once the outer surface 708 is brought into contact with and/or inserted into the desired tissue region, the working fluid within the cavity 714 starts to evaporate thereby initiating the cooling of the desired tissue region to a target temperature. As the working fluid evaporates, vapor V flows out of the cavity 714 while working fluid flow L is maintained within the channels 712 to facilitate the continuous cooling of the desired tissue region. The design of the channels 712 within the inner surface 706 is configured to maintain working fluid flow within at least a portion of the channels 712 toward the distal end 704, and prevent dry-out, against the friction to fluid flow within the channels 712. The driving force to induce working fluid to flow into the channels 712 is maintained by the gradient in liquid pressure along the channels 712 as they extend axially along the inner surface 706. The pressure gradient is induced by the change in capillary pressure that results from the change in the structure of the channels 712 as they extend axially along the inner surface 706 toward the distal end 704. Specifically, as shown in FIGS. 33-35, the average radius for liquid meniscus within the channels 712 decreases step-wise as the channels 712 extend axially along the inner surface 706 toward the distal end 704. In the illustrated non-limiting example, the decrease in the meniscus radius within the channels 712 may be facilitated by an increase in the circumferential distribution of the channels 712 as the channels 712 extend axially along the inner surface 706. That is, the number of channels 712 arranged circumferentially around the inner surface 706 may increase step-wise as the channels 712 extend axially toward the distal end 704. Thus, the design of the invasive cooling device 700 ensures that working fluid flow is maintained within at least a portion of the channels 712 along the inner surface 706 to provide evaporative cooling to the desired tissue region throughout the cooling process.

In some non-limiting examples, the channels 712 may define a continuous flow path as they increase in circumferential disbursement axially along the invasive medical device 700. That is, the channels 712 adjacent to the proximal end 702 (FIG. 33) may branch into the channels 712 in between the proximal and distal ends 702 and 704 (FIG. 34), which may then branch into the channels 712 adjacent to the distal end 704 (FIG. 35). In some non-limiting examples, the channels 712 may be at least partially discontinuous as they increase in circumferential disbursement axially along the invasive medical device 700.

In some non-limiting examples, the invasive medical device 700 may, instead of the channels 712, include a plurality of microspheres arranged within an inner cavity defined by the inner surface. The microspheres with varying diameters may be arranged at different locations axially along the inner cavity. For example, microspheres with the smallest diameter may be provide axially along a portion of the inner cavity adjacent to the needle tip 710, microspheres with the largest diameter may be provided axially along a portion of the inner cavity adjacent to the proximal end 702, and microspheres with a medium diameter may be provided between the smallest diameter and largest diameter microspheres. In this way, the varying diameters may draw the working fluid into the inner cavity by capillary forces and enable the evaporation of the working fluid therein.

In some non-limiting examples, the invasive medical device 700 may be combined with a heating to provide varying thermal characteristics axially therealong. For example, the a top portion of the invasive medical device 700 may be provided with one of the various evaporative structures described herein and a bottom portion of the invasive medical device may be provided with a heat source (e.g., RF heating) to provide a combined heating a cooling effect. For example, the cooling effect may mitigate pain associated with the heating effect.

In some non-limiting examples, the invasive medical device 700 may be arranged into an array to, for example, to be implemented in a fractional medical treatment.

In accordance with a non-limiting configuration, the use or method of use of the invasive medical device 700 does not include a step of treatment of a human or animal body by surgery or therapy. It is noted that the skills of a person using a device as described herein, may not have the skills of a physician, and that the intended treatment may not be motivated due to illness of the treated person, rather for aesthetic reasons.

Various parameters of the invasive medical device 700 may be varied to control the heat removal capacity and operating temperature range based on the application. For example, the pattern of the channels 712 on the inner surface 706, the thermophysical properties of the working fluid, the material of the noninvasive medical device 700, and the coatings on the inner surface 706 and the outer surface 708. It should be appreciated that the control of the cooling capacity of the invasive medical device 700 may be more constrained than the noninvasive medical devices described herein. That is, the significantly increased cooling capacities provided by the two-phase heat transfer process leveraged by the systems and methods described herein may require specific attention to the cooling capacity of the invasive medical device 700 to prevent tissue damage. Table 3 below provides various non-limiting examples of the properties and operational characteristics of the invasive medical device 700.

TABLE 3

Properties and Operating Characteristics of the Invasive Medical Device 700

| | |
|---|---|
| Operating Range | −220° C. to 200° C. |
| Operating Pressure | 0.1 bar to 10 bar |
| Working Fluids | Hydrocarbons, Hydrofluorocarbons, Hydrofluoroolefins, Water, Aqueous Solution, Binary Mixtures, Cryogenic Fluids: $N_2$, $O_2$ |
| Needle Material | Metals, Non-metallic elements, Composite Materials Examples: Copper, Aluminum, Graphite |
| Needle-Wall-Internal Structure | Microgrooved, Fractional Pattern Microchannels, Nano-Spheres |
| Porous Substrate Pore Size | 100 nm-20 µm |
| Needle Internal Wall Coatings | Wetting or non-wetting coating, Gold, Anodized Nano-Layers |
| Fluid Flow Control | Electroosmotic Driven Flow, EMF, Piezo-electric, Capillary Tube |
| Fluid Injection | Direct Heat Exchange, Micro-nozzles for enhanced mixing |
| Temperature Control | Thermocouple, RTD, Embedded Contact Microwires |

Figure 36:
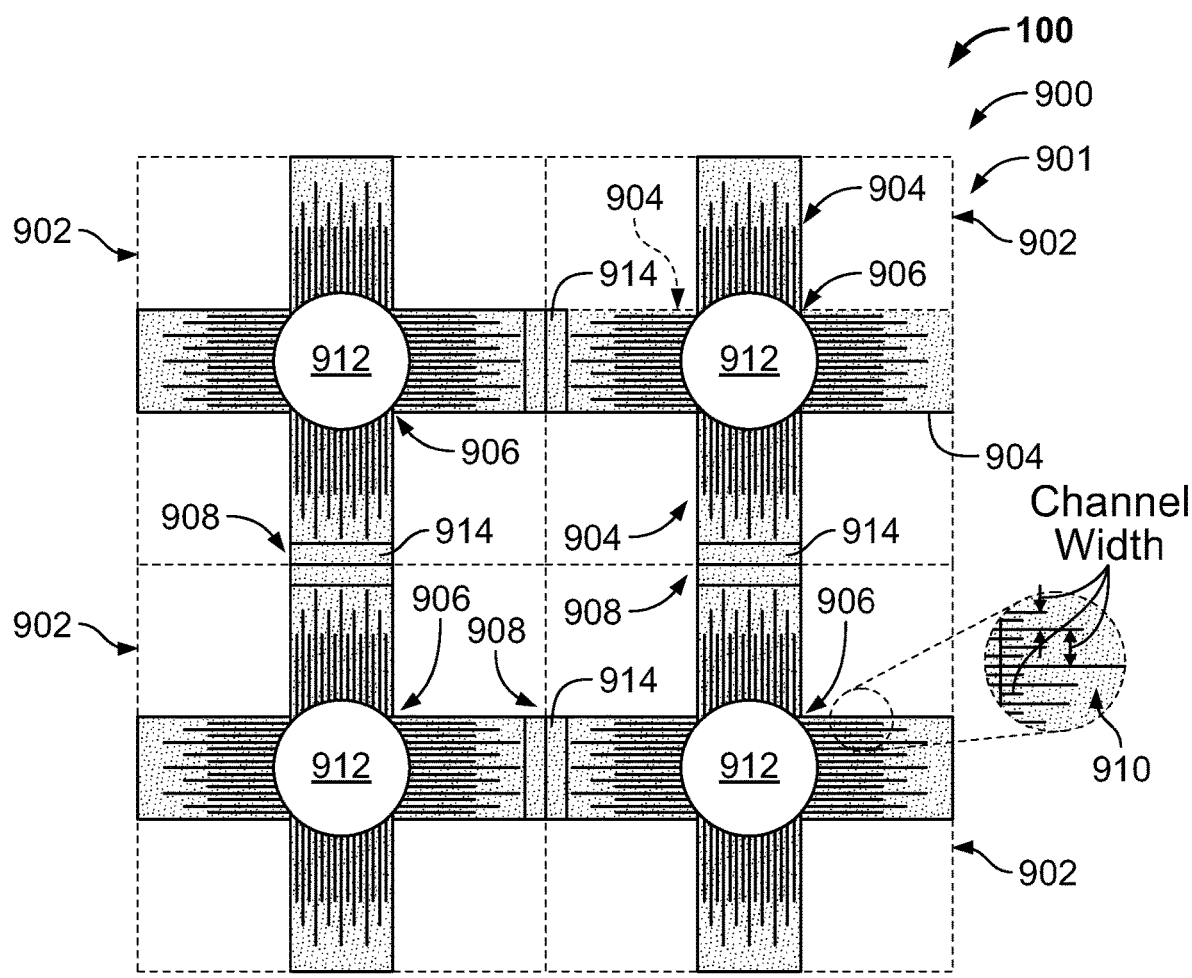
FIG. 36 is a schematic illustration of a noninvasive medical device array for use in fractional medical applications according to one aspect of the present disclosure.
Figure 37:
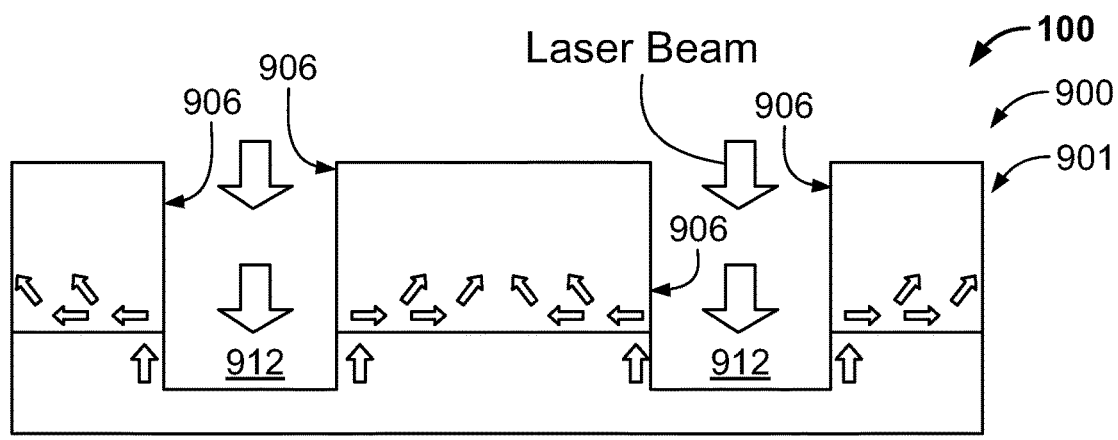
FIG. 37 is a side view of the noninvasive medical device array of FIG. 36.

As described above, the medical device 100 may be in the form of a noninvasive medical device. FIGS. 36 and 37 illustrate another non-limiting example of a noninvasive medical device array 900 configured to cool a tissue region via a two-phase heat transfer process in accordance with the systems and methods described herein. In the illustrated non-limiting example, the noninvasive medical device array 900 may be implemented to provide cooling adjacent to locations subjected to a fractional damage or injury pattern. In some non-limiting examples, the fractional damage or injury pattern may be created through the use of electromagnetic energy (e.g., a laser), radiofrequency needle, coring need, or other device that causes tissue damage either through heating, mechanical disruption, ultrasound or other methods of causing tissue damage. The noninvasive medical device array 900 may be comprised of a base 901 having a plurality of openings 912 arranged therein to accommodate a fractional treatment pattern. In the illustrated non-limiting example, the base 901 includes a plurality of array tiles 902. Each of the array tiles 902 includes a plurality of array units 904 that are configured to provide cooling to a tissue region adjacent to the fractionally heated tissue.

The array units 904 include a proximal end 906, a distal end 908, and a plurality of channels 910 arranged thereon. The proximal end 906 is configured to be arranged adjacent to the fractionally heated tissue. When assembled, the proximal ends 906 are configured to combine to create an opening 912 through which the fractional treatment may be performed. That is, the openings 912 formed by the assembled proximal ends 906 of the array units 904 provides access to the tissue region in a desired fractional pattern. The number of openings 912 and orientation of the openings 912 formed by the noninvasive medical device array 900 is not meant to be limiting in any way, and the array tiles 902 may be modularly arranged to create any fractional pattern, as desired.

The distal ends 908 may be in fluid communication with a fluid source 914. In the illustrated non-limiting example, the fluid source 914 may be an accumulation, or pool, of working fluid. The working fluid may be naturally drawn into the channels 910 and flow therethrough based on the capillary pressure induced by the design of the channels 910. The channels 910 may extend varying lengths along the array unit 904 from the proximal end 906 to a location between the proximal end 906 and the distal end 908. In this way, number of channels 910 for the working fluid to flow through increases as the fluid is drawn from the distal end 908 to the proximal end 906 on each of the array units 904. Since the array units 904 define a fixed width, as the number of channels 910 for the working fluid to flow through increases, a channel width experienced by the fluid flowing through the channels 910 along the array units 904 may decrease. This decrease in channel width may induce the capillary pressure necessary to draw the working fluid from the fluid sources 914 to the proximal ends 906, thereby filling the channels 910 of each array unit 904 with working fluid. Once filled with working fluid, each of the channels 910 within array units 904 may form menisci to facilitate the evaporation of the working fluid. The evaporation of the working fluid from the channels 910 may remove heat conductively from the array units 904.

In operation, the noninvasive medical device array 900 may be placed in contact with a tissue region that will be subjected to a fractional medical treatment that will result in heating of the tissue in a fractional pattern. The noninvasive medical device array 900 is modularly constructed to enable the array tiles 902 to be arranged in any fraction pattern to conform to the desired medical treatment. Once constructed in the desired fraction pattern, the fluid source 914 may be placed in fluid communication with the distal ends 908 of the array units 904 to fill the channels 910 with working fluid. The working fluid within each of the channels 910 can form menisci along the channels 910 to promote the evaporation of the working fluid within the channels 910. Heat may be absorbed from the tissue region and transferred through the array units 904 to the working fluid within the channels 910 where the heat input may facilitate the evaporation of the working fluid at the menisci formed therein. The heat absorbed from the tissue region may cool the tissue region in the areas where the array units 904 contact the tissue region. The openings 912 formed by the array tiles 902 enable the fractional medical or cosmetic treatment (e.g., incident laser light) to be performed on the tissue region, while the tissue adjacent to, or around, the openings 912 are cooled by the noninvasive medical device array 900. As is known in the art, it is imperative to ensure that tissue between regions of fractional treatment remain undamaged to promote healing. Furthermore, the cooling provided by the noninvasive medical device array 900 may provide an anesthetic effect. Thus, the noninvasive medical device array 900 may add to the efficacy, safety, comfort, and/or tolerability of fractional medical treatments.

Figure 38:
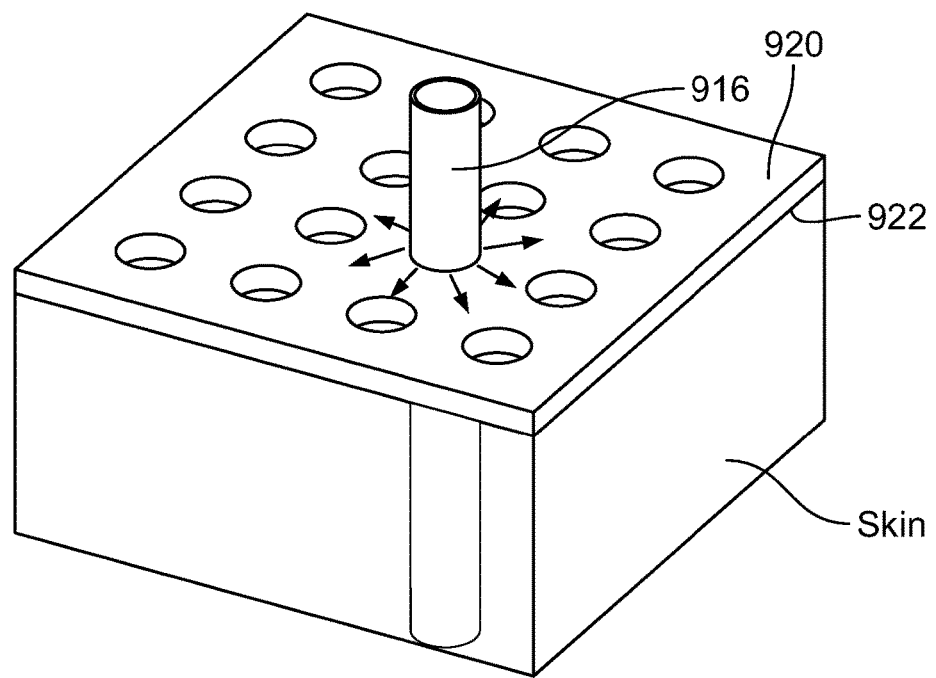
FIG. 38 is a top, front, right isometric view of another noninvasive medical device array for use in fractional medical applications according to one aspect of the present disclosure.
Figure 39:
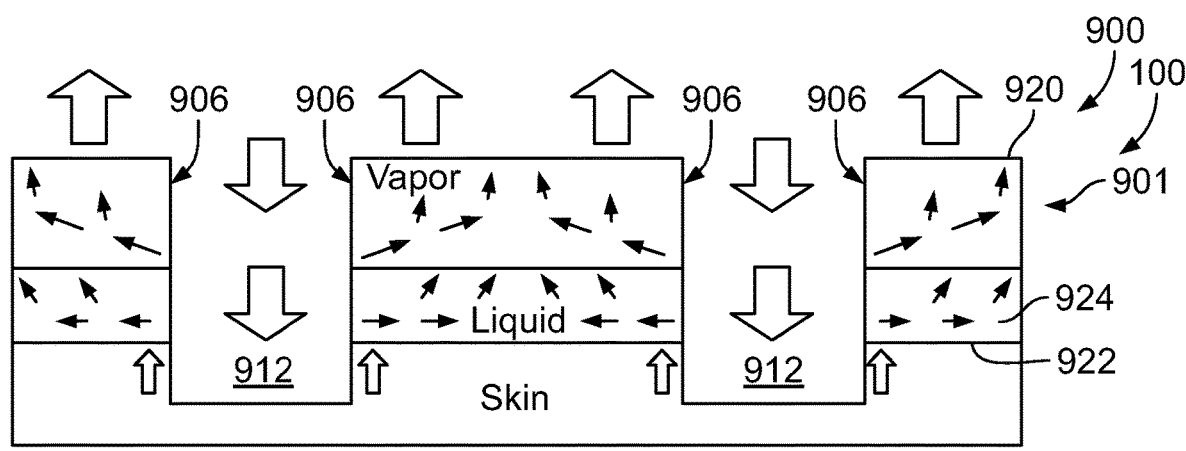
FIG. 39 is a side view of the noninvasive medical device array of FIG. 38.

FIGS. 38 and 39 illustrate another non-limiting example of the noninvasive medical device array 900 that may be implemented to provide cooling adjacent to locations subjected to a fractional damage or injury pattern using a two-phase heat transfer process in accordance with the systems and methods described herein. As illustrated in FIGS. 38 and 39, the noninvasive medical device array 900 includes the plurality of openings 912 arranged in a desired fractional pattern. The plurality of openings 912 may be dimensioned to enable, for example, a laser beam 916 to propagate therethrough and subject a tissue region 918 to a fractional treatment (e.g., ablation).

In general, the individual areas on the surface of the tissue region 918 subjected to the laser beam 916 may be very small. In addition, the laser beam 916 may deliver large amounts of energy in short bursts of time. Thus, the neighboring areas of the tissue region 918 not subjected to the laser beam 916 require large amounts of heat to be dissipated in a short amount of time to prevent the formation of hot spots, which may undesirably damage the neighboring tissue. Due to the two-phase heat transfer process leveraged by the noninvasive medical device array 900, any growing temperature gradients forming in the tissue neighboring the plurality of openings 912 may be decayed rapidly by localized high flux evaporation of a working fluid within the noninvasive medical device array 900.

In the illustrated non-limiting example, the noninvasive device array 900 may include a top plate 920, a bottom plate 922, and an evaporative structure 924 arranged between the top plate 920 and the bottom plate 922. The top plate 920 and the bottom plate 922 may be fabricated from a metal material (e.g., aluminum) and may provide a seal around the plurality of openings 912. In some non-limiting examples, the evaporative structure 924 may be open to the atmosphere along the sides thereof to facilitate the introduction of the working fluid therein. In some non-limiting examples, the evaporative structure 924 may comprise a plurality of microchannels or a porous substrate (e.g., a metal foam). In any case, the evaporative structure 924 is configured to be filled with a working fluid (e.g., by placing the working fluid in fluid communication with the evaporative structure 924 and allowing capillary forces to draw the working fluid into the evaporative structure 924). Once filled with the working fluid, the evaporative structure 924 may be in its thermodynamic equilibrium with its own pure vapor.

During a fractional ablation procedure, for example, a high flux is introduced by the laser beam 916 at the onset of ablation. As the laser beam 916 drills deeper into the tissue region 918, the high temperature area on the surface of the tissue region 918 begins to spread radially through the tissue region 918 at each of the fractional sites (i.e., adjacent to each of the plurality of openings 912). This heat spread continues to propagate through the tissue region 918 at each of the fractional sites long after the laser beam 916 has been removed. Without sufficient cooling applied to the areas neighboring the fractional sites, the thermal damage area may grow quickly into the neighboring areas, as an undesirable side effect.

The noninvasive medical device array 900 illustrated in FIGS. 38 and 39 provides a heat transfer path with an extremely small resistance compared to the alternative path (i.e., through the tissue). Therefore, heat is conducted to from the tissue region 918 to the bottom plate 922 and into the evaporative structure 924. The heat in the desired tissue region 918 in contact with the bottom plate 922 is rapidly removed and spread by the immediate evaporation of the working fluid within the evaporative structure. The evaporative structure 924 may maintain the working fluid in liquid form over the entire surface of the bottom plate 922 to ensure uniform evaporative cooling capacity as the laser beam 916 encounters the surface of the tissue region 918. For example, evaporated working fluid may condense once it contacts the top plate 920 and the condensed working fluid may fall back into the evaporative structure 924. In the illustrated non-limiting example, the noninvasive medical device array 900 may operate passively and may not include any moving parts, which provides an advantage over conventional medical cooling technologies.

Various parameters of the noninvasive medical device array 900 may be altered to control the heat removal capacity and operating temperature range based on the application. For example, the material of the array units 904, the number and arrangement of the array units 904, the width of the channels 910, the thermophysical properties of the working fluid, etc. It should be appreciated that the properties and operating characteristics of the noninvasive medical device 600 in Table 2 may apply to the noninvasive medical device array 900.

In accordance with a non-limiting configuration, the use or method of use of the noninvasive medical device array 900 does not include a step of treatment of a human or animal body by surgery or therapy. It is noted that the skills of a person using a device as described herein, may not have the skills of a physician, and that the intended treatment may not be motivated due to illness of the treated person, rather for aesthetic reasons.

In some non-limiting examples, the design and properties of the noninvasive medical device array 900 provide several advantages in addition to the significantly increased cooling capacity described herein. For example, the noninvasive medical device array 900 may be fabricated from an opaque mesh structure that protects tissue oriented under the mesh structure from being subjected to the electromagnet energy. While the mesh is opaque to the electromagnetic energy, the openings within the mesh do not create any losses in the transmission of the electromagnetic energy to the surface of the tissue region, which is not true when sprays or sapphire cooling systems are used. In some non-limiting examples, the noninvasive medical device array 900 provides a framework for delivering a distributed but localized pressure to the surface of the tissue region. This substantially increases the pressure applied to a given location subjected to the mesh. To this end, the framework may provide constriction of blood flow due to the pressure applied, and constriction of nerve signals from tissue oriented distally from the brain with the framework located more proximally.

In addition to the non-limiting examples of the noninvasive medical device array 900 described herein, the noninvasive medical device array 900 may be formed of tubes that facilitate evaporative cooling with the tubes extending to form a mesh across the surface of the tissue region. In this case, the diameter and distribution of the tubes may be selected to create a mesh having parameters in ratios that are selected to optimize parameters, such as cooling, pressure, protected tissue surface area, amount of time dedicated to pre-cooling of the tissue before laser application, and the like.

In some non-limiting applications, the noninvasive medical device array 900 may be used with other therapeutic systems, such as needles or surgical devices (e.g., biopsy systems and the like). Cooling, tissue protection, and pressure application to constrain blood flow, or nerve signal conduction may be used in conjunction with needle application through the openings in the mesh or surgical devices extended through the openings in the mesh, such as biopsy devices extended through the device or the like.

Regardless of the particular clinical application being performed, the noninvasive medical device array 900 may be utilized with negative pressure or suction/vacuum systems, where the tissue arranged in the opening of the array may be subjected to a negative pressure as part of a larger therapeutic procedure.

Figure 40:
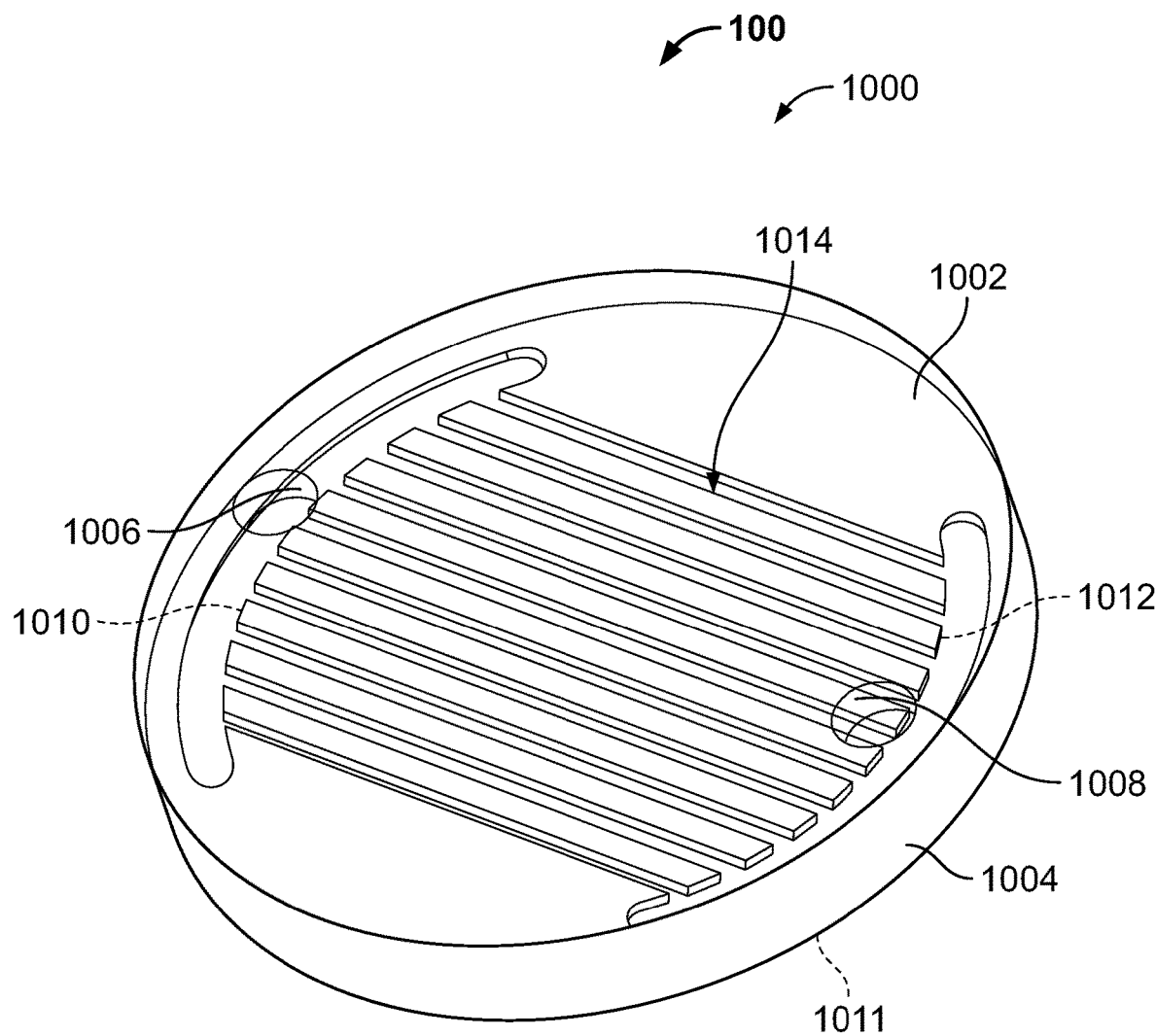
FIG. 40 is a top, front, right isometric view of a transparent noninvasive medical device according to one aspect of the present disclosure.
Figure 41:
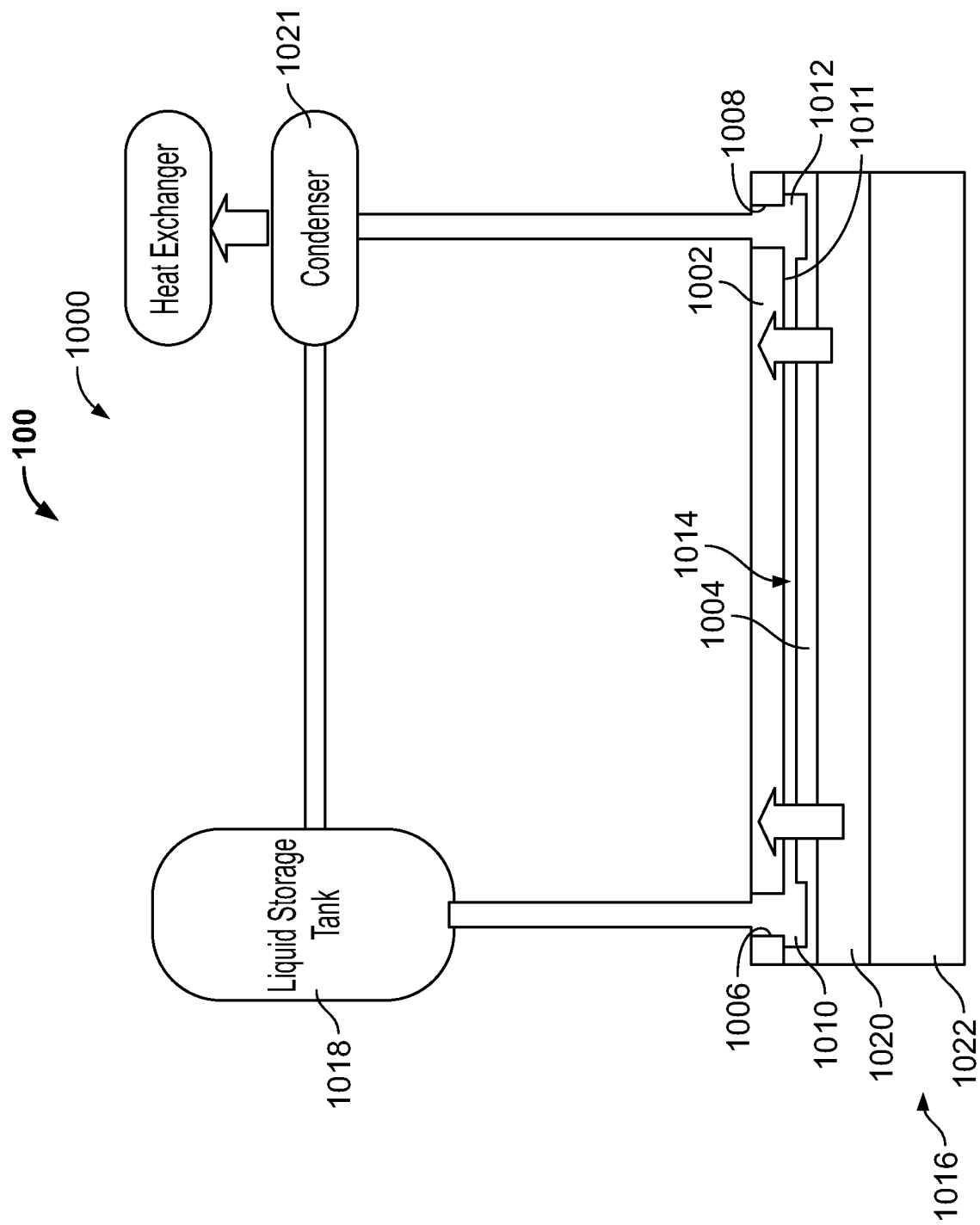
FIG. 41 is a schematic illustration of the transparent noninvasive medical device of FIG. 40 assembled and treating a tissue region according to one aspect of the present disclosure.

FIGS. 40 and 41 illustrate a non-limiting example of a noninvasive medical device 1000 that may be implemented to provide cooling adjacent to locations subjected to a fractional damage or injury pattern using a two-phase heat transfer process in accordance with the systems and methods described herein. The noninvasive medical device 1000 may also be implemented in other medical cooling applications other than fractional treatments (e.g., photo-dynamic treatments and tumor ablation).

As illustrated in FIG. 40, the noninvasive medical device 1000 includes a top plate 1002 and a bottom plate 1004. The top plate 1002 and the bottom plate 1004 may be fabricated from a transparent, or optically transmissive, material. The material that the top plate 1002 and bottom plate 1004 are fabricated from may be chosen to provide desired optical characteristics. For example, the noninvasive medical device 1000 may be used to cool non-target tissue in applications where electromagnetic energy is delivered to a tissue region. Thus, the material for the top plate 1002 and the bottom plate 1004 may be chosen to be transparent in the wavelength range that corresponds with a given electromagnetic treatment.

The top plate 1002 may include an inlet port 1006 and an outlet port 1008 that both extend through the top plate 1002. When assembled, the inlet port 1006 is configured to align with an inlet reservoir 1010 formed in the bottom plate 1004 and the outlet port 1008 is configured to align with an outlet reservoir 1012 formed in the bottom plate 1004. The bottom plate 1004 includes a plurality of microchannels 1014 that extend between the inlet reservoir 1010 and the outlet reservoir 1012. In some non-limiting examples, a porous substrate may be arranged between the top plate 1002 and the bottom plate 1004. Each of the inlet reservoir 1010, the outlet reservoir 1012, and the plurality of microchannels 1014 are recessed into the bottom plate 1004.

In some non-limiting examples, a ratio of the projected area used by the plurality of microchannels 1014 to the total contact surface area (i.e., the bottom surface 1011 of the bottom plate 1004) may be less than 10%. In some non-limiting examples, a ratio of the projected area used by the plurality of microchannels 1014 to the total contact surface area (i.e., the bottom surface 1011 of the bottom plate 1004) may be less than 5%. In any case, the projected area occupied by the plurality of microchannels 1014 is very small relative to the contact surface area. Thus, the substantial majority of the bottom plate 1004 may be uninterrupted by the plurality of microchannels 1014, which leaves significant space for the electromagnetic energy to pass through the noninvasive medical device 1000 without interruption.

In the illustrated non-limiting example, each of the plurality of microchannels 1014 defines a generally constant width, rectangular cross-section. In other non-limiting examples, the plurality of microchannels 1014 may define an alternative shape and/or pattern on the bottom plate 1004. For example, the spacing between the microchannels 1014 and shape of the path traversed by the microchannels 1014 between the inlet reservoir 1010 and the outlet reservoir 1012 may be designed to prevent interference with any incoming electromagnetic energy (e.g., a fractional laser patter, a single laser beam, etc.). In some non-limiting examples, the spacing between the microchannels 1014, the pattern of the microchannels, 1014, and/or the geometry of the cross-section defined by the microchannels 1014 may be tuned to provide a fast cooling response and steady cooling, while avoiding interference with incoming electromagnetic energy. In some non-limiting examples, the inner surface of the microchannels 1014 may be covered with a coating, or patterned to enhance fluid flow and lower friction losses.

In the illustrated non-limiting example, the noninvasive medical device 1000 defines a generally round shape. In other non-limiting examples, the noninvasive medical device 1000 may define another shape (e.g., curved, polygonal, etc.). For example, the contact surface 1011 of the bottom plate 1004 and/or the noninvasive medical device 1000 may take any of the various geometries described herein with reference to the base 602 and the treatment surface 606 of the noninvasive medical device 600.

With reference to FIGS. 40 and 41, during operation of the noninvasive medical device 1000, for example, the contact surface 1011 of the bottom plate 1004 may be brought into contact with the surface of a desired tissue region 1016 to be subjected to an electromagnetic-based treatment. The working fluid may be drawn from an external reservoir 1018 and enter the inlet reservoir 1010 of the bottom plate 1004 through the inlet port 1006 of the top plate 1002. The working fluid may be distributed over the plurality of microchannels 1014 passively by surface tension and intermolecular forces (e.g., capillary forces).

Electromagnetic energy may be transmitted through the noninvasive medical device 1000, without interference, in a desired treatment pattern. The working fluid flowing through the plurality of microchannels 1014 may absorb incoming thermal energy from the tissue region 1016 and evaporate. The evaporation of the working fluid as is flows along the plurality of microchannels 1014 toward the outlet reservoir 1012 induces a direct and uniformly distributed cooling effect over the entire contact area of the contact surface 1011. The working fluid may exit through the outlet port 1008 in the gas phase (e.g., vapor), and the vapor leaving the outlet port 1008 may be collected, condensed in a condenser 1021, and returned to the reservoir 1018.

As illustrated in FIG. 41, the cooling effect provided by the noninvasive medical device 1000 may protect a non-target tissue region 1020 from heat generated by the incoming electromagnetic energy, and ensure that a target tissue region 1022 is subjected to the desired medical treatment provided by the electromagnetic energy. Flow of the working fluid to the noninvasive medical device 1000 may be controlled via one or more feedback signals acquired from the tissue region 1016 and/or the noninvasive medical device 1000. For example, the temperature at one or more locations along the bottom plate 1004, a contact force between the contact surface 1011 and the surface of the tissue region 1016, and/or a temperature at one or more locations at the interface between the contact surface 1011 and the surface of the tissue region 1016.

Various parameters of the noninvasive medical device 1000 may be altered to control the heat removal capacity and operating temperature range based on the application. For example, the material of the top plate 1002 and the bottom plate 1004, the number and arrangement of the plurality of microchannels 1014, the geometry and pattern of the channels 1014, the thermophysical properties of the working fluid, etc. It should be appreciated that the properties and operating characteristics of the noninvasive medical device 600 in Table 2 may apply to the noninvasive medical device 1000.

In accordance with a non-limiting configuration, the use or method of use of the noninvasive medical device 1000 does not include a step of treatment of a human or animal body by surgery or therapy. It is noted that the skills of a person using a device as described herein, may not have the skills of a physician, and that the intended treatment may not be motivated due to illness of the treated person, rather for aesthetic reasons.

As described herein, the present disclosure provides various non-limiting examples of noninvasive medical devices 100, 600, 900, and 1000, which may be implemented to selectively cool a tissue region in medical applications. Due to the noninvasive nature of these devices, it may be desirable to acquire the feedback signals, which may be used to control these devices, noninvasively. Some of the feedback signals that may be used to control the noninvasive medical devices 100, 600, 900, and 1000 disclosed herein are the temperature within the tissue region are various locations and depths within the tissue region. Additionally, in some medical applications, it is desired to determine the temporal and spatial distribution of temperature within a tissue region to ensure that a target tissue region is treated, while other tissue regions remain untreated. For example, it may be necessary to track a cold front penetrating into a tissue region and to control a medical cooling device based on a desired location or depth of this cold front. Clearly, obtaining temperature information within a tissue region would require an invasive technique. Thus, the present disclosure provides an approach to noninvasively determine a spatial and temporal temperature distribution at various depths within a tissue region, for example, based on a temperature distribution measured at the surface of the tissue region.

Figure 42:
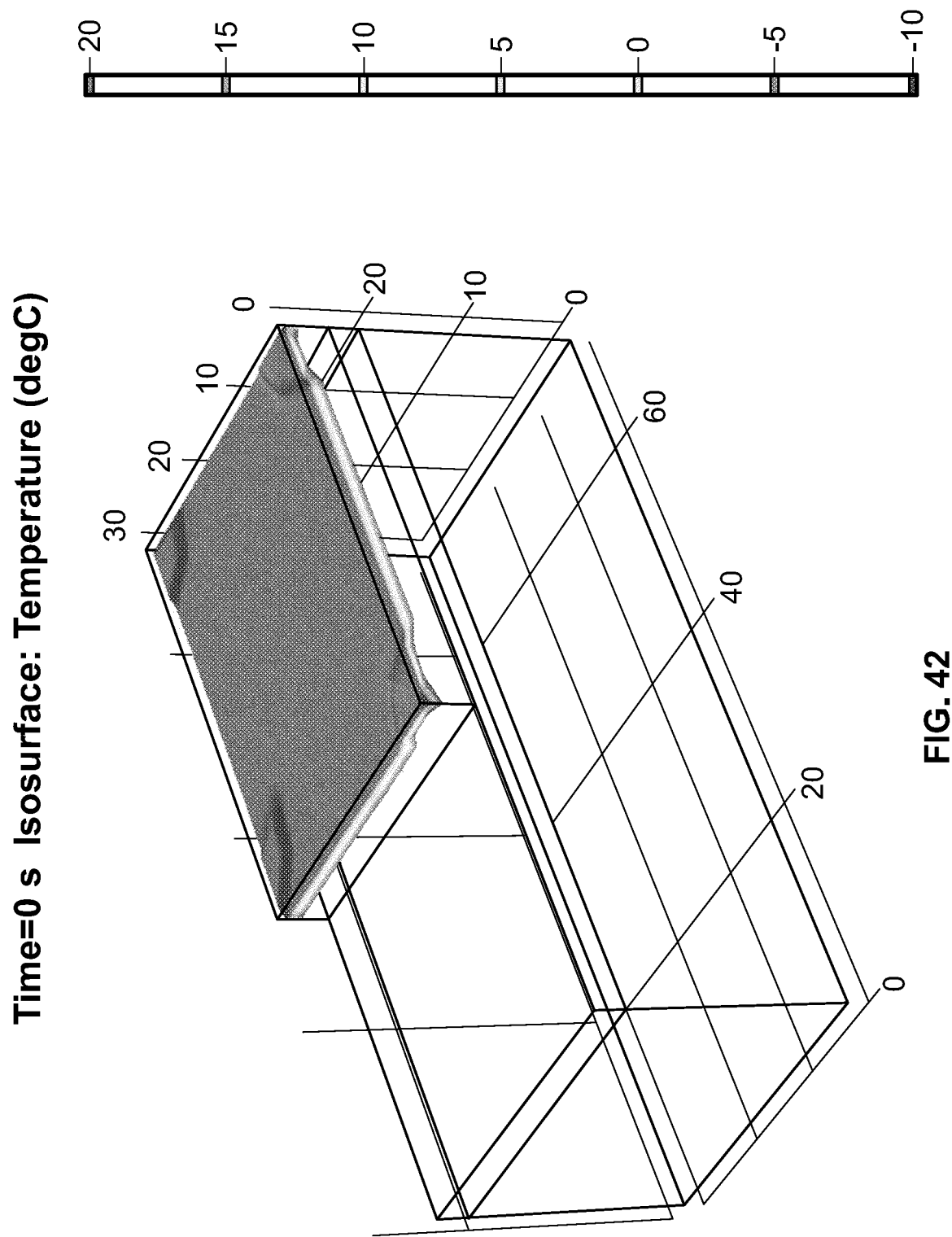
FIG. 42 is a graph illustrating an initial temperature of a cooling device arranged on a tissue region.
Figure 43:
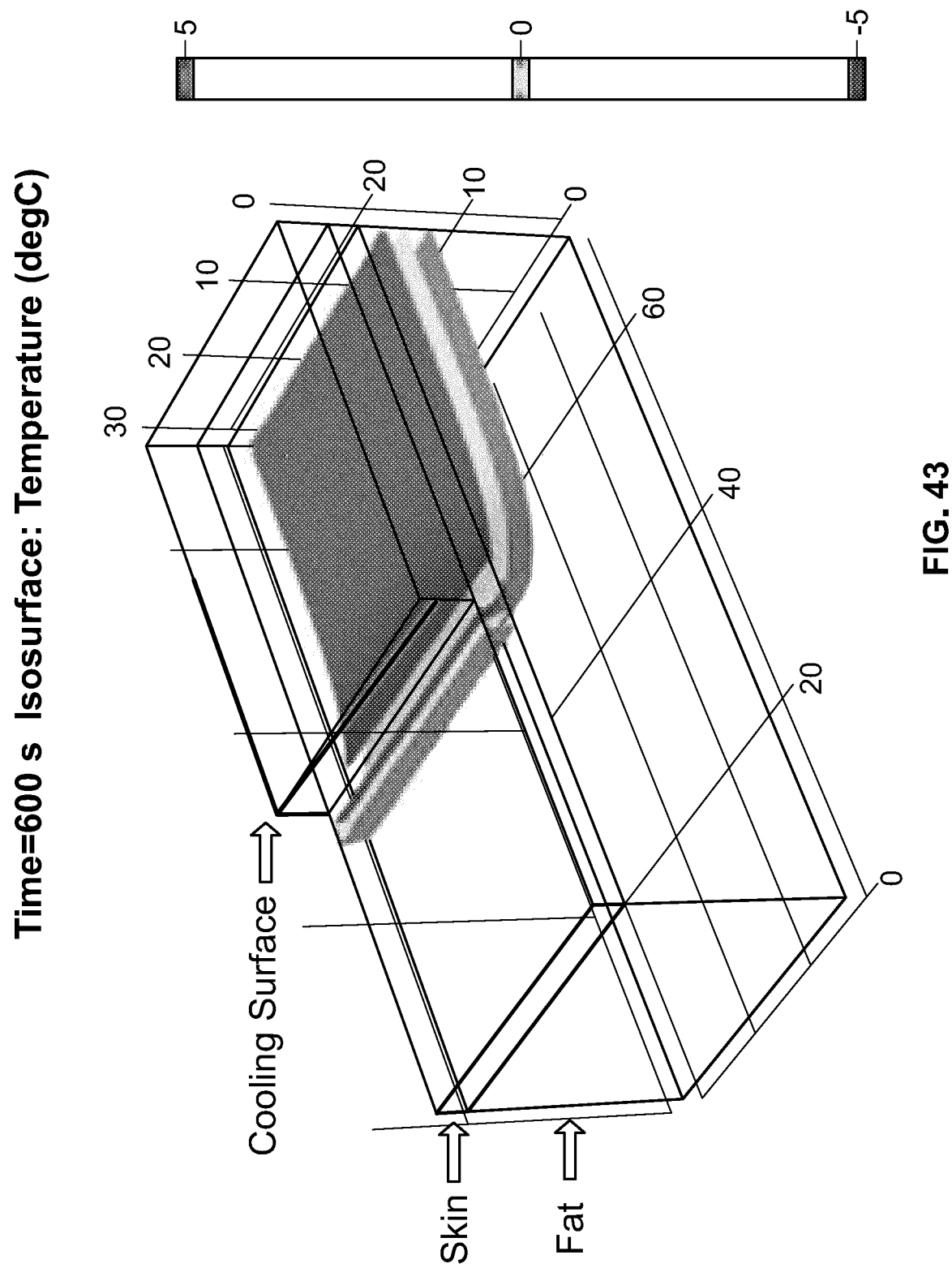
FIG. 43 is a graph illustrating isothermal layers within the tissue region while cooling is being applied by the cooling device.

FIGS. 42 and 43 are a graphs depicting one non-limiting example of a progression of isothermal surfaces that illustrate penetration of a cold front in a medium (e.g., tissue). By measuring the temperature at any point and direction of the isothermal surfaces, the temperature distribution in other points and directions may be extracted. The present disclosure provides an approach to determine the temperature distribution within this tissue region based on information gathered from the surface of the tissue region. In some non-limiting examples, a plurality of temperature measurements gathered at the surface of a tissue region may be related to the actual existing temperature profiles within the tissue region (e.g., in the fat layer) at different depths at a given time.

Figure 44:
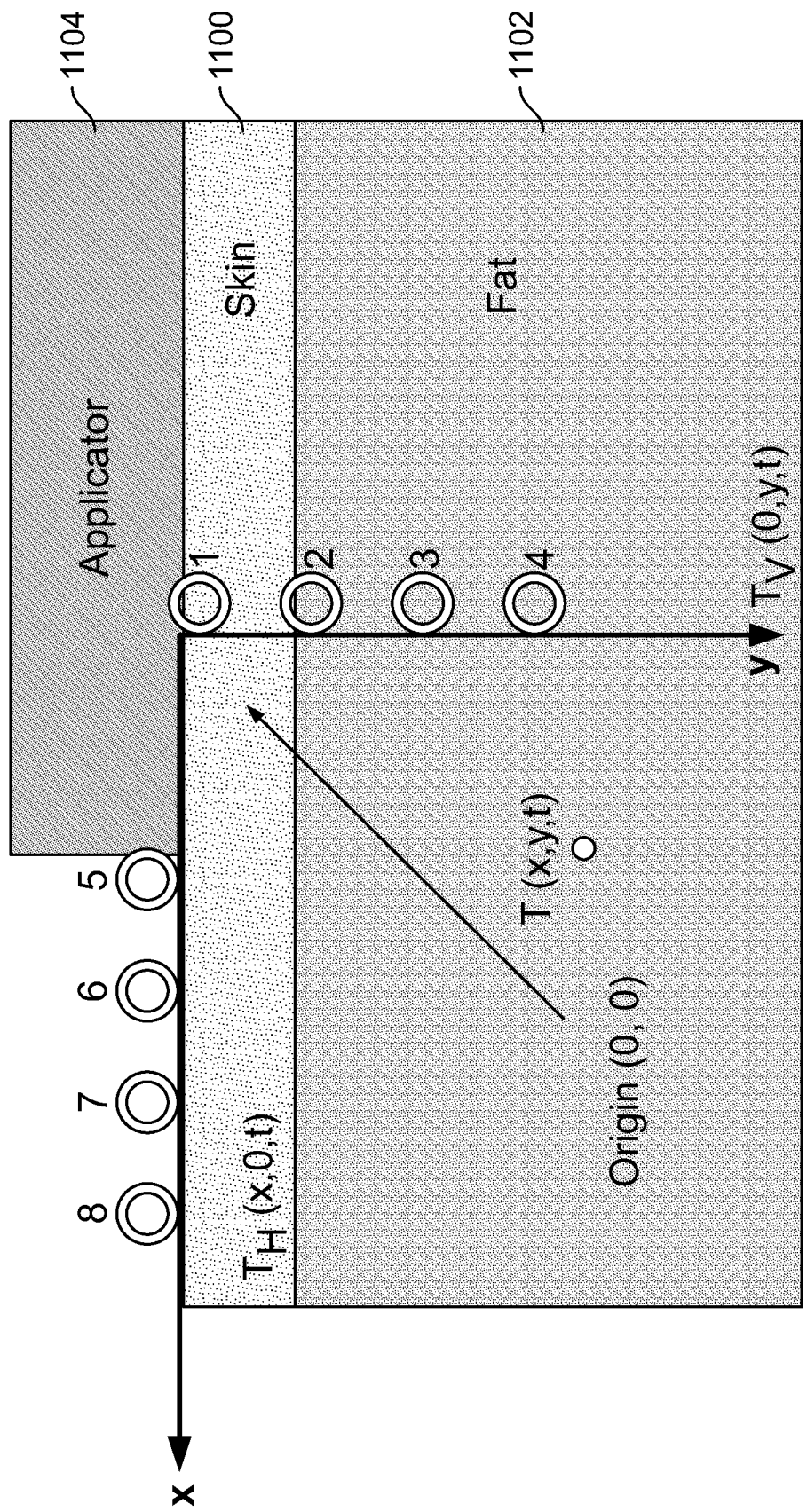
FIG. 44 is a schematic illustration of a non-invasive temperature monitoring and control system according to one aspect of the present disclosure.
Figure 45:
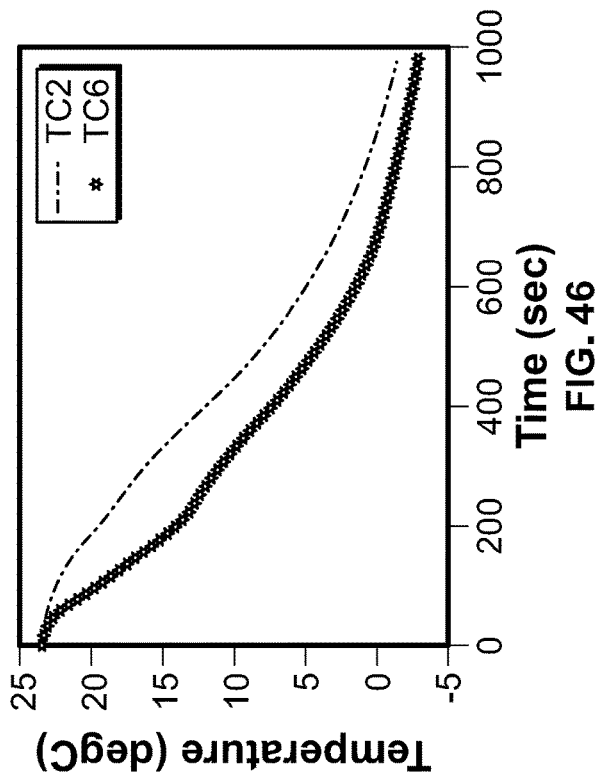
FIG. 45 is a graph illustrating temperature as a function of time at locations 1 and 5 in FIG. 44.
Figure 46:
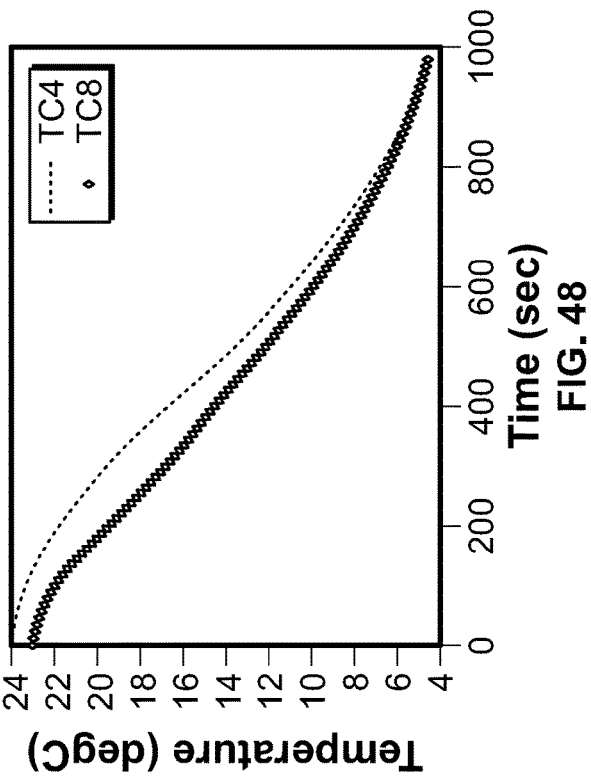
FIG. 46 is a graph illustrating temperature as a function of time at locations 2 and 6 in FIG. 44.
Figure 47:
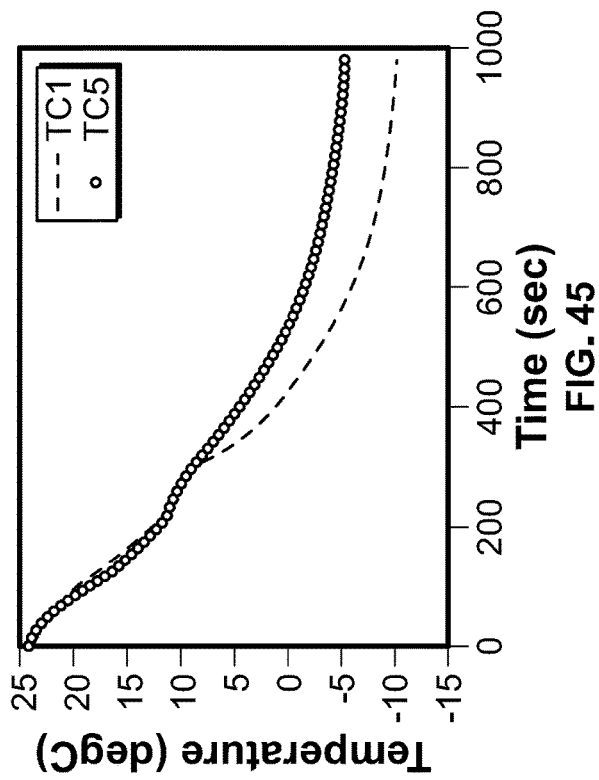
FIG. 47 is a graph illustrating temperature as a function of time at locations 3 and 7 in FIG. 44.
Figure 48:
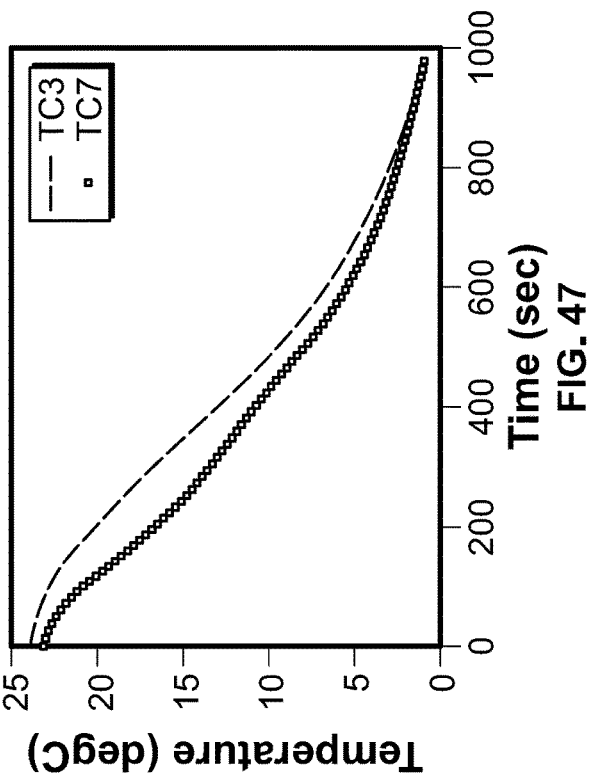
FIG. 48 is a graph illustrating temperature as a function of time at locations 4 and 8 in FIG. 44.

FIG. 44 illustrates one non-limiting example of a test setup utilized to develop the noninvasive temperature determination approach according to the systems and methods of the present disclosure. In the illustrated non-limiting example, the test was performed on a cubic sample of pig tissue with a skin layer 1100 and a fat later 1102. The pig skin was at an initial temperature of 24° C. and a flat cooling applicator 1104 with an initial temperature of −15° C., which covered half of the skin. Four thermocouples (numbered 1-4 in FIG. 44) were placed are varying depths Y1, Y2, Y3, an Y4 within the tissue sample under the cooling applicator 1104. In addition, four thermocouples (numbered 5-8 in FIG. 44) were placed along the surface of the skin at different locations X1, X2, X3, and X4 next to the cooling applicator 1104. By interpolating between these four data points (i.e., X,Y pairs) at a given time, a function that describes the temperature at any given point on the skin for that given time may be calculated. This information may provide the temperature profile distribution for the surface of the skin in that specific time. Thus, the temperature at any given point inside the fat or on the surface of the skin may be a function of its coordinates and time (i.e., $T(t)=f(x, y, t)$, where T is temperature, x is the distance along the skin surface from an origin, and y is the depth into the tissue from the origin, and t is time).

Figure 49:
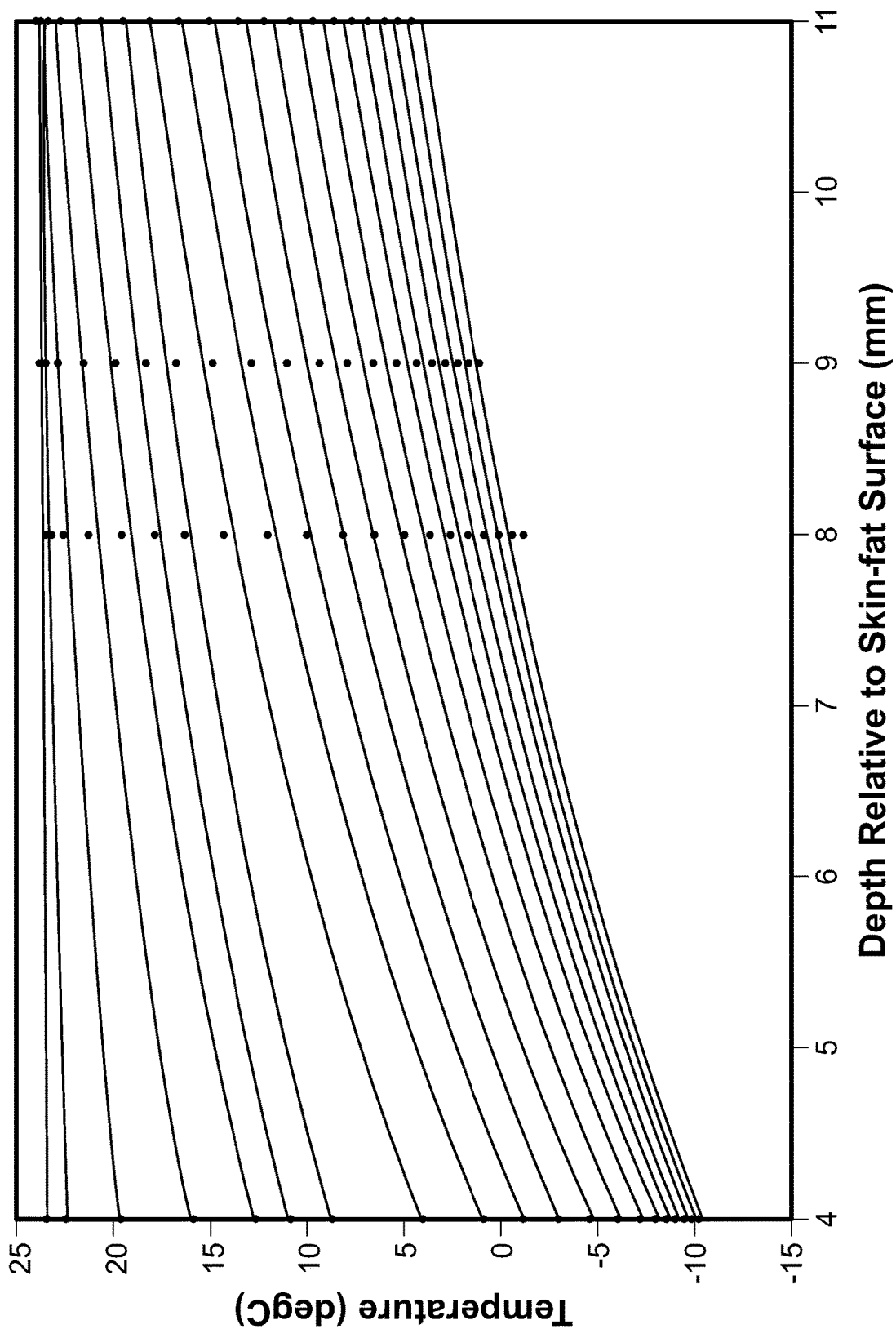
FIG. 49 is a graph illustrating an interpolation of the temperature of locations 5-8 in FIG. 44.
Figure 50:
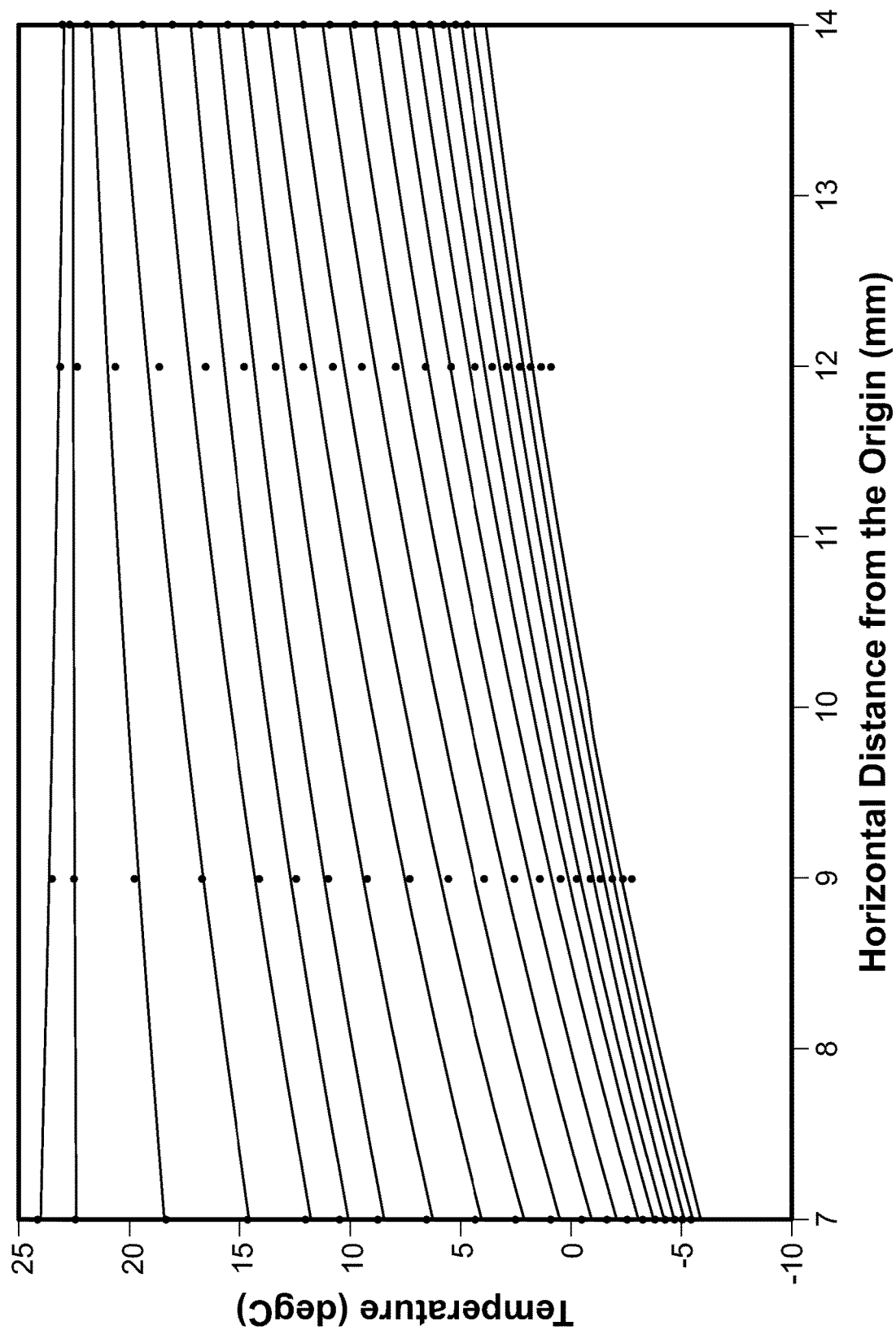
FIG. 50 is a graph illustrating an interpolation of the temperature of locations 1-4 in FIG. 44.

FIGS. 45-48 are graphs illustrating the temperature as a function of time for the eight thermocouples depicted in FIG. 44 for one thousand seconds after the cooling applicator was brought into contact with the skin. The interpolation of the temperature of the four horizontal thermocouples for each fifty second interval from the start till the end of the one thousand second experiment verses the horizontal distance from the origin are illustrated in the graph of FIG. 49. By equating each of the extracted equations to a desired temperature, the location of the points with that temperature can be extracted. For example, a thermocouple on the surface of the skin can be represented by $T(t)=f(x, 0, t)$. By solving this equation for 0° C., the equation becomes: $f(x, 0, t)=0$. Then for t=1:50:1000, the corresponding values for x(t) can be extracted from the extracted equations.

The interpolation of the temperature of the four vertical (depth) thermocouples for each fifty second interval from the start till the end of the one thousand second experiment versus the depth relative to the skin surface are illustrated in the graph of FIG. 49. This data gives a second function $T(t)=f(0, y, t)$. By solving this equation for 0° C., the equation becomes $f(0, y, t)=0$. Then for t=1:50:1000, the corresponding values for y(t) can be extracted.

With the gathered information, now x and y pairs are known at the same time for T=0° C. For example, at the time that the temperature at a location five millimeters from the origin is going to be 0° C., the corresponding depth into the tissue region that the temperature is also 0° C. can be determined. Thus, the pairs for identical temperatures at difference depths into the tissue region can be determined. For example, for any isotherms at 0° C., an equation $y=f(x)$ can be developed to determine the temperature at various depths into the tissue region when the option to invasively measure the temperature within the tissue is unavailable or undesirable to implement. By placing the X coordinate at its corresponding temperature equation, a corresponding depth for that temperature can be determined within the tissue region. Eventually, a function can be developed that equates the depth within the tissue region to a length on the surface of the skin for the exact same temperature.

Figure 51:
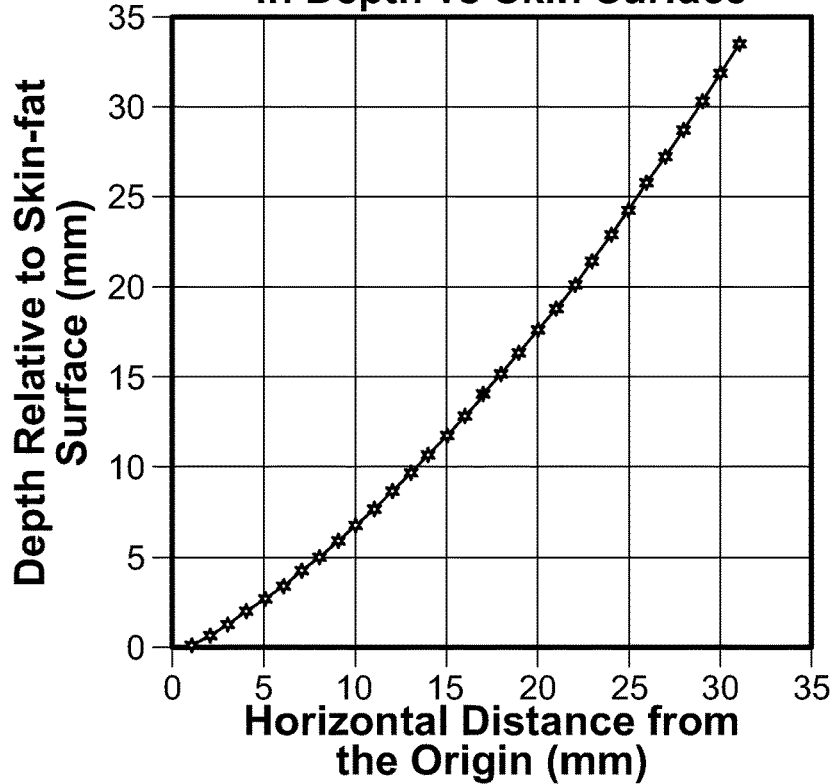
FIG. 51 is a graph illustrating x, y pairs for a 0° C. isotherm based on the interpolation date in FIGS. 49 and 50.
Figure 52:
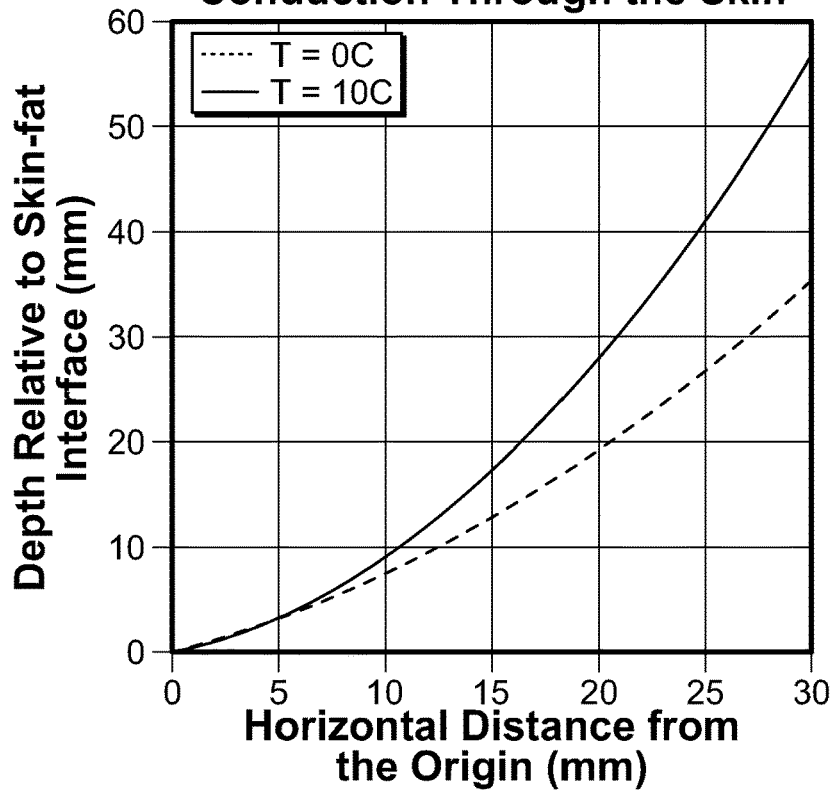
FIG. 52 is a graph illustrating x, y, pairs of a 10° C. isotherm and the can also be determined and are plotted with the 0° C. isotherm 0° C. isotherm based on the interpolation date in FIGS. 49 and 50.

FIG. 51 is a graph illustrating the x, y pairs for the 0° C. isotherm in the experiment described above. Using the above-described approach, the x, y, pairs of the 10° C. isotherm can also be determined and are plotted with the 0° C. isotherm in FIG. 52. As illustrated, the x, y pairs for any temperature isotherm can be determined based on a corresponding temperature at the surface of the tissue region. Thus, the present disclosure provides an approach to noninvasively determine a spatial and temporal temperature profile within a tissue region based on a temperature at a surface of the tissue region. In real world applications, the option of providing the thermocouples at various depths within the tissue region may not be practical, however, the equations described above have already been developed, which may act as virtually having the thermocouples within the tissue region. Thus, the need to invasively measure a temperature at depth within a region may be eliminated and the approach described herein may act to relate the temperature at the surface of a tissue region to the temperature at depth.

In some non-limiting applications, one or more temperatures may be measured on a tissue surface adjacent to a medical device configured to provide a thermal effect to a tissue region. For example, one or more temperatures may be measured at a predetermined intervals to the side or adjacent to a medical device configured to provide a thermal effect to a tissue region. In this way, the temperature profile at the tissue surface may be determined and, using the approach described herein, correlate this profile at the surface to a profile within, or at depth into, the tissue region. It should be appreciated that the approach for noninvasively measuring a temperature profile within a tissue region may be equally applicable to medical cooling technologies and medical heating technologies.

The various medical devices 100, 600, 700, 900, and 1000 described herein that may be implemented to cool a tissue region described herein may be controlled by varying one or more control parameters. For example, fluid flow into the devices 100, 600, 700, 900, and 1000 can be adjusted to control the temperature and cooling rates applied to the tissue region. The fluid flow rates may be controlled either passively or actively. For passive control, fluid flow is controlled by the pressure in the device 100, 600, 700, 900, and 1000 and, if present, the condenser (e.g., the condenser 112, 1022). The pressure in the device 100, 600, 700, 900, and 1000 and, if present, the condenser may be determined by the incoming heat flux, heat loss, and the geometry and orientation of the device 100, 600, 700, 900, and 1000 and, if present, condenser as well as the liquid and vapor transport lines between them. Some advantages of passive fluid flow control are the simplicity of the system, straight forward integration, and higher reliability.

For active control, a control valve, flow control device, or a capillary tube may control the fluid flow to the device 100, 600, 700, 900, and 1000 and/or the vapor pressure in the condenser, if present. The control system response may be tuned based on the feedback parameters obtained by a monitoring system. Some advantages of the active fluid flow control are the flexibility in responding to sharp temperature fluctuations and user defined cooling/heating procedures.

As described herein, another control parameter to adjust the operating characteristics of the devices 100, 600, 700, 900, and 1000 may be the thermo-physical properties of the working fluid used. The thermophysical properties may determine the performance, operating ranges for temperature, pressure, and cooling rates, and the geometrical parameters of the device 100, 600, 700, 900, and 1000 and, if present, the condenser. Several substances can be employed as working fluid for each particular application. Each fluid determines its own operating condition and design parameters based on its equilibrium pressures, latent heat of evaporation, density, etc. Therefore, selection of the cooling fluid(s) is essential in the design, operation, and specifically optimization and control of a phase-change heating/cooling system.

In addition to flow control and working fluid selection, the temperature of the treatment/contact surface for the devices 100, 600, 700, 900, and 1000 described herein may be controlled directly using electrical heating, and/or convective heating/cooling. Each of these methods can be integrated into the phase-change system as an auxiliary system for ultra-fast response or reversing the temperature change direction quickly, if needed.

In some non-limiting examples, the temperature and cooling/heating rates of a the devices 100, 600, 700, 900, and 1000 described herein may also be controlled using two or more substances employed as working fluid. For example, in a two-fluid system, Fluid A may be introduced to lower the temperature quickly from initial tissue temperature to an intermediate temperature. The thermos-physical properties of the fluid determine/assure a fixed minimum temperature for the step 1 of the cooling. The system can then switch to using Fluid B to cool the target tissue to the final temperature. This process may be reversed to then bring the tissue back to the intermediate temperature, if desired. The multi-fluid process may be expanded to implement more than two working fluids to define as many temperature "steps" as desired.

In some non-limiting examples, the quality of the thermal/mechanical contact between the tissue and the devices 100, 600, 700, 900, and 1000 described herein may be important in controlling the heat exchange rates across the cooling/heating interface. The local normal force, the presence and thickness of interfacial materials such gels, pastes, etc. and an applied vacuum level are among crucial factors affecting the thermal resistance and thermal contact quality. Each of these parameters can be used to adjust and control the heat flow and cooling rates across the tissue/hot/cold plate interfaces.

EXAMPLES

The following examples set forth, in detail, ways in which the various medical devices described herein that leverage a two-phase heat transfer process to cool a tissue region may be used or implemented, and will enable one of skill in the art to more readily understand the principles thereof. The following examples are presented by way of illustration and are not meant to be limiting in any way.

Figure 53:
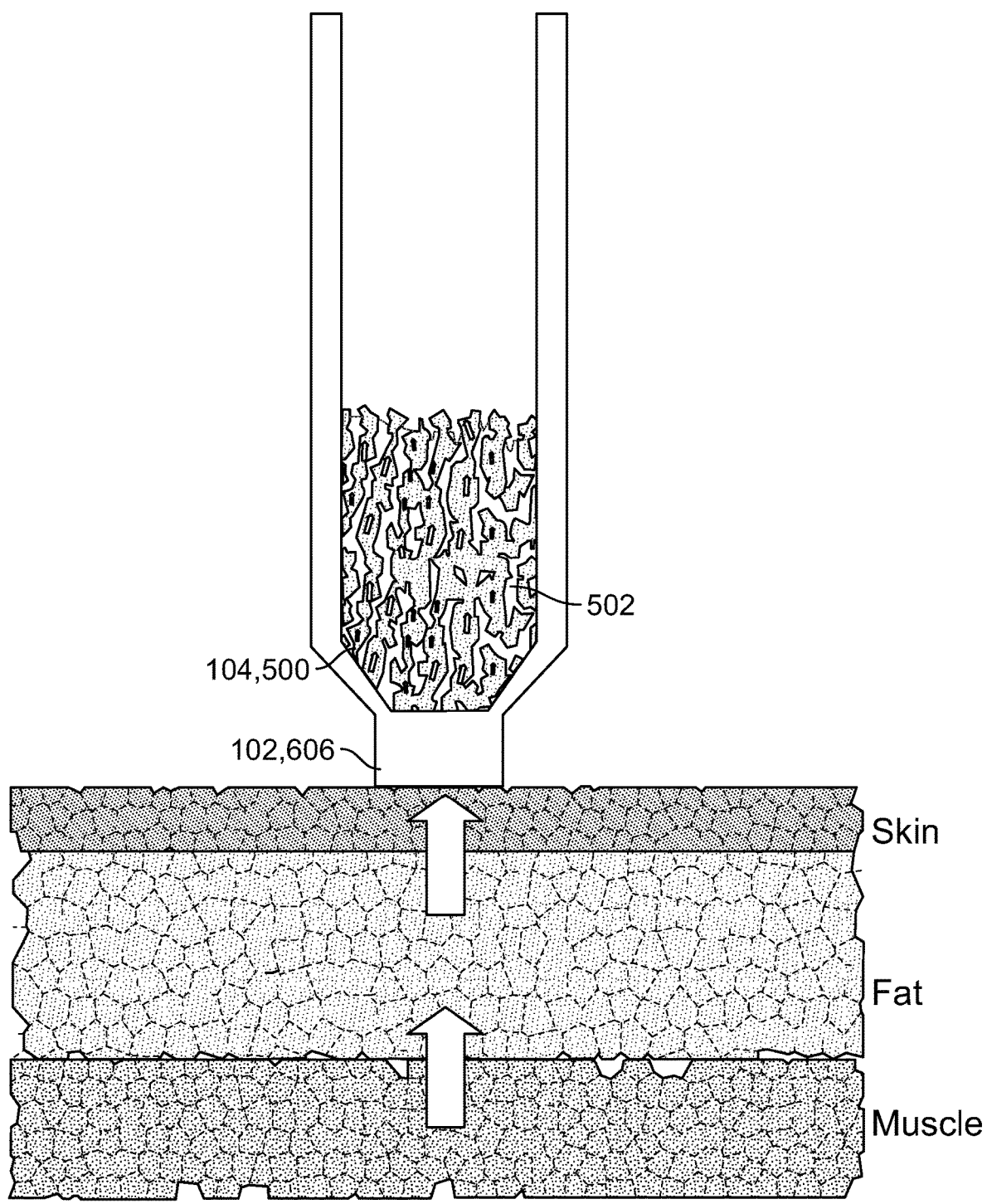
FIG. 53 is a schematic illustration of a test setup used to measure a temperature as a function of time at varying depths into a simulated tissue region that was noninvasively cooled using two-phase cooling.

FIG. 53 illustrates a test setup utilized to test the two-phase heat transfer process leveraged for cooling a tissue region according to the systems and methods described herein. A porous substrate was arranged within a metal applicator that includes a contact surface. The metal applicator was fabricated from 6061 aluminum and includes a contact surface of 15 millimeters (mm), a wall thickness of 4 mm, and an outer diameter (of the portion receiving the porous substrate) of 24 mm. The porous substrate was fabricated from aluminum and included a variable pore size that decreased as the porous substrate progressed toward the contact surface. The decreasing pore size enabled a working fluid to be naturally drawn into the porous substrate due to capillary forces in accordance with the systems and methods described herein. The working fluid for the test was iso-butane ($C_4H_{10}$), and the working pressure was 1 bar. The boiling point of iso-butane is −11.7° C. at 1 bar. The tissue sample tested included an average skin thickness of 2.5 mm and a fat thickness of 20 mm. For the test, the tissue sample was inserted into a plastic enclosure with dimensions slightly larger than the sample itself to reduce heat exchange between the tissue sample and the surroundings. The enclosure covered all but the top surface (i.e., the skin surface) of the tissue sample where it was in contact with the contact surface of the applicator. The tissue sample tested was porcine.

Initially, all of the components including the tissue sample, the enclosure, and the applicator were at thermal equilibrium with the ambient air. The contact surface was brought into engagement with the surface of the tissue sample and the liquid iso-butane was injected into the applicator. The temperature was measured as a function of time at varying depths into the tissue for both the illustrated two-phase device and thermoelectric cooling. The temperature was measured using Omega Hypodermic Type-E thermocouples HYP-1.

Figure 54:
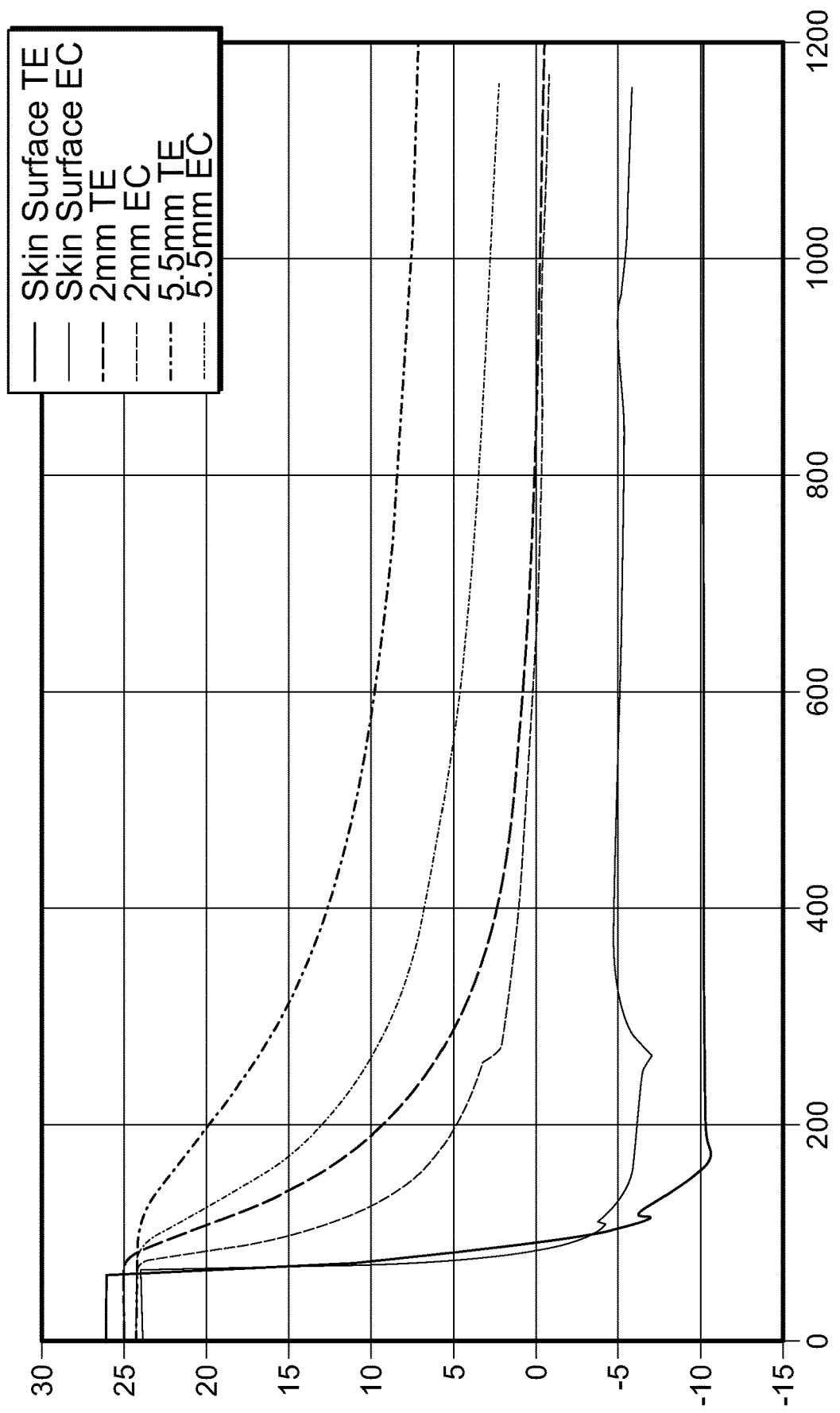
FIG. 54 is a graph illustrating the temperature as a function of time at varying depths within the simulated tissue setup of FIG. 53 for thermoelectric cooling and two-phase cooling.

As illustrated in FIG. 54, once the iso-butane was injected into the porous substrate of the applicator, the two-phase cooling penetrated more rapidly into the simulated tissue. For example, after 200 seconds (s) the thermoelectric cooling had only cooled from approximately 24° C. to approximately 20° C. at a depth of 5.5 mm into the tissue sample, while the two-phase cooling cooled the tissue sample to approximately 13° C. in the same time. In addition, the two-phase cooling device maintained the surface of the tissue sample at a higher temperature when compared to the thermoelectric cooling, while simultaneously maintaining a colder temperature at a depth of 5.5 mm into the tissue sample. Thus, the two-phase cooling, when compared to thermoelectric cooling, provides more rapid cooling that can penetrate to greater depths within the tissue and maintain the surface of the tissue at warmer temperatures.

Figure 55:
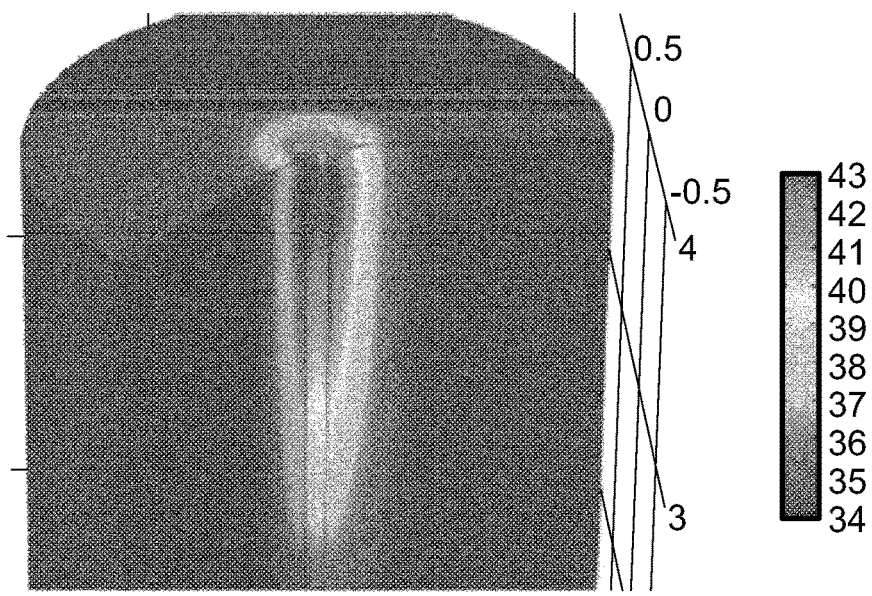
FIG. 55 is a graph illustrating a three-dimensional temperature profile after 0.059 seconds within a tissue region being subjected to a laser treatment and being cooled by a non-invasive medical device according to the present disclosure.
Figure 56:
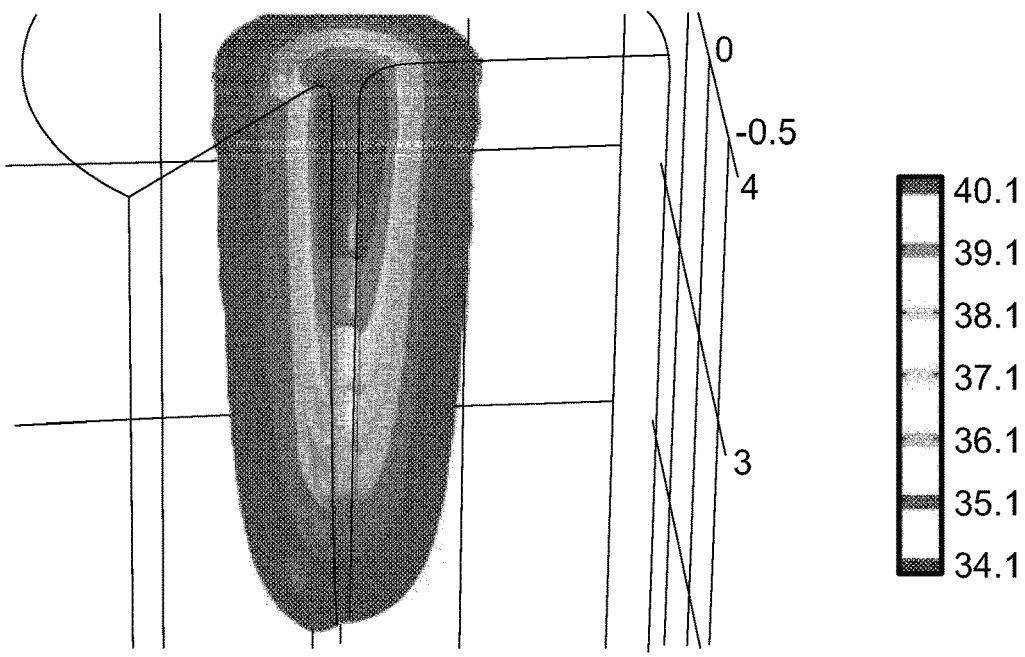
FIG. 56 is a graph illustrating a three-dimensional temperature profile after 0.073 seconds within a tissue region being subjected to a laser treatment and being cooled by a non-invasive medical device according to the present disclosure.
Figure 57:
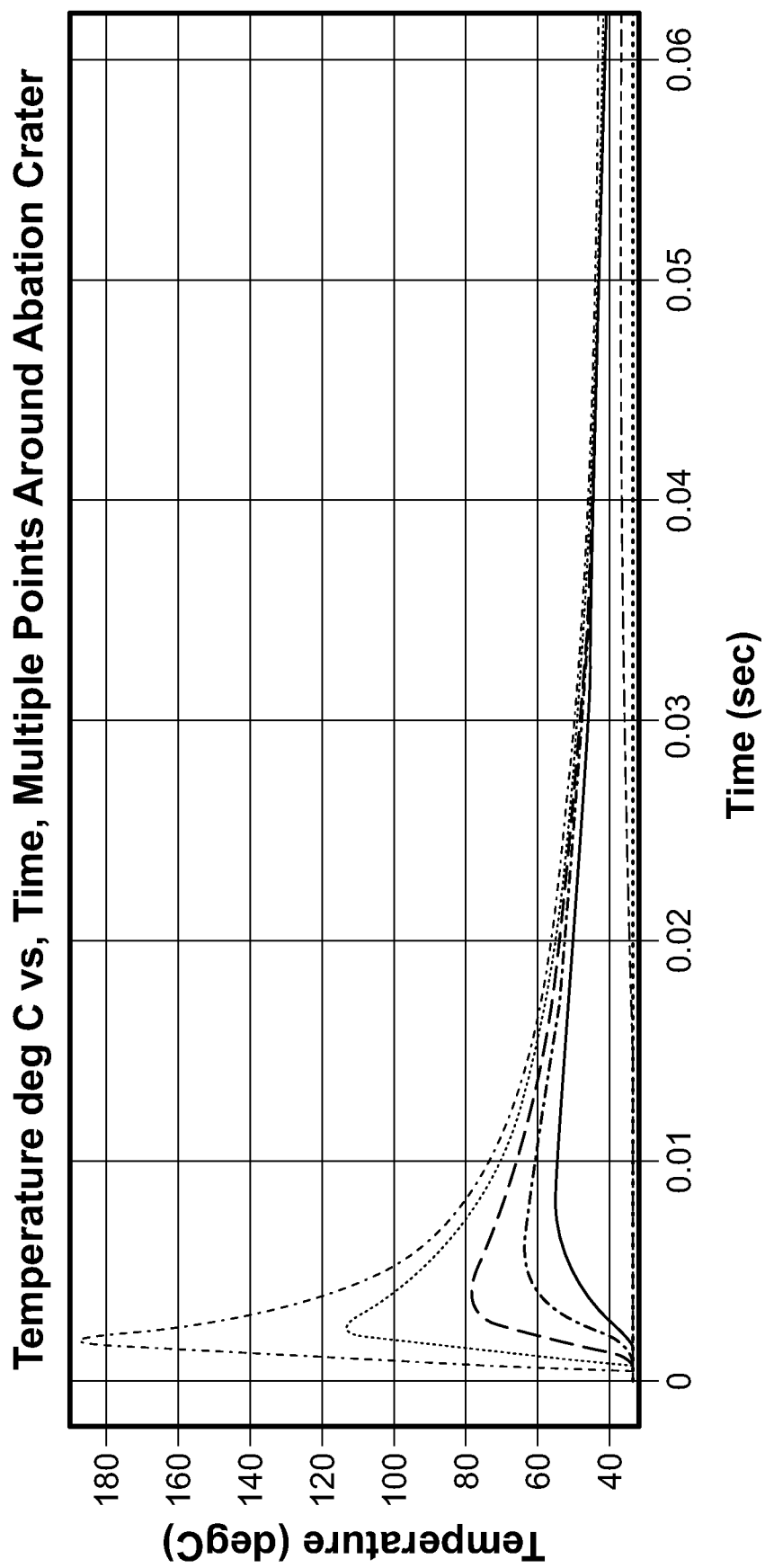
FIG. 57 is a graph illustrating temperature as a function of time for varying distances radially from the laser beam for the cooling treatment illustrated in FIGS. 55 and 56.

FIGS. 55-57 illustrates a model of a tissue region after being subjected to a laser pulse during an ablation procedure. The noninvasive medical device array 900 is placed in contact with the tissue surrounding the laser beam. As illustrated in FIGS. 55 and 56, the heat input from the laser is rapidly dissipated by the noninvasive medical device array 900. FIG. 57 illustrates the temperature as a function of time at various locations radially outward from the laser beam. After the delivery of the laser energy (i.e., the peaks illustrated in the graph), the noninvasive medical device array 900 almost instantaneously (e.g., less than 0.2 seconds) decreases the temperature in the regions radially outward from the laser beam to a non-damaging temperature.

Figure 58:
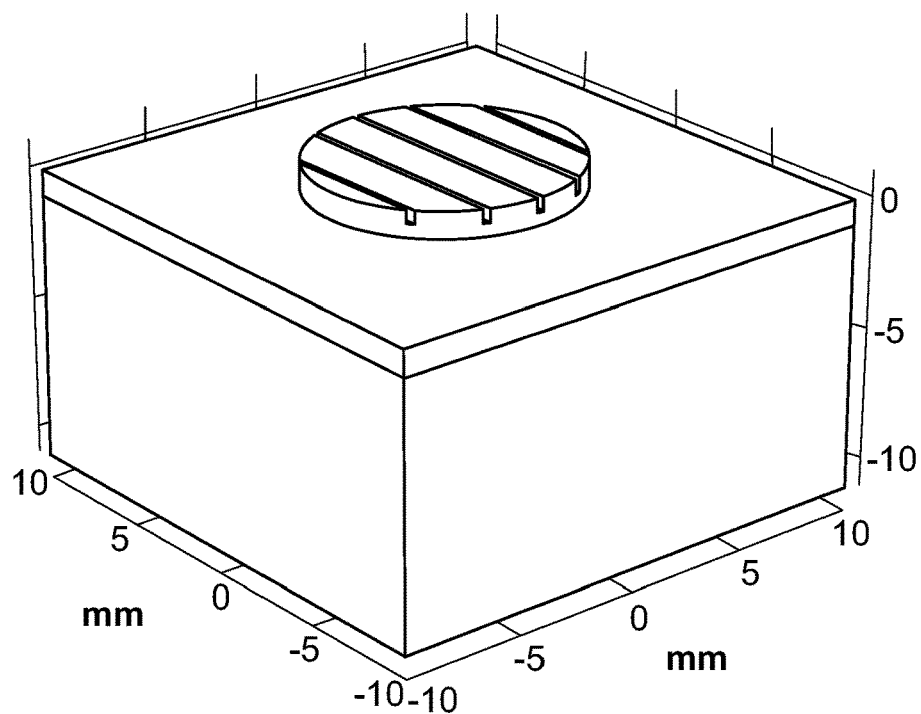
FIG. 58 illustrates a setup used to model the cooling performance of a transparent noninvasive medical device during a laser-based medical treatment.
Figure 59:
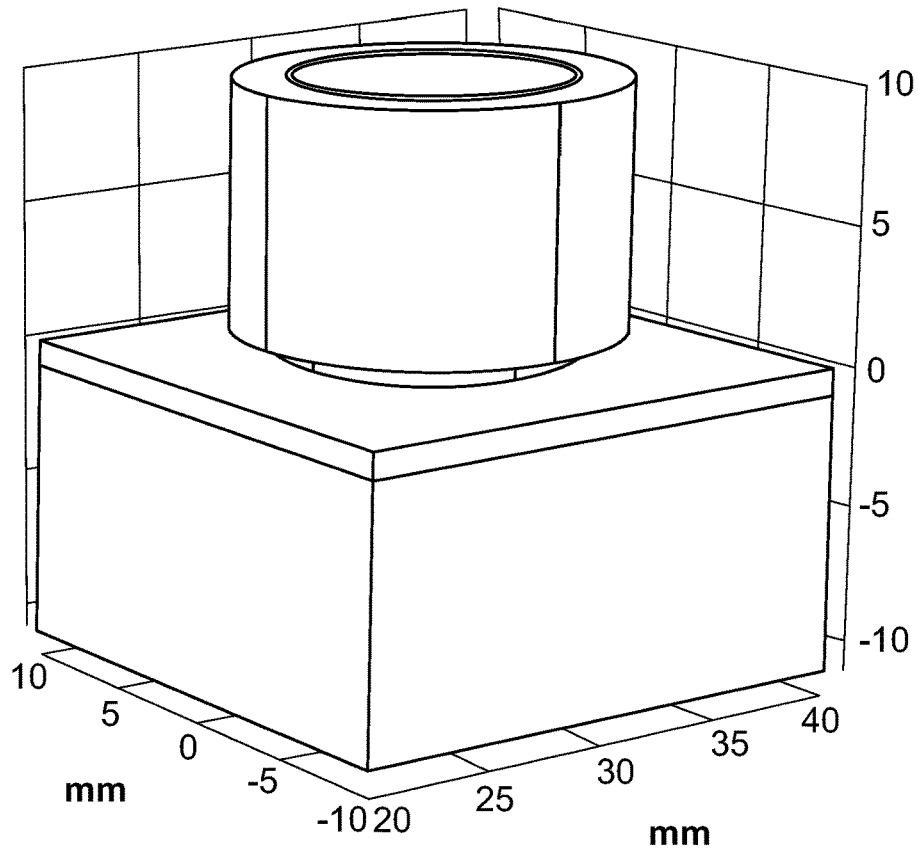
FIG. 59 illustrates a setup used to model the cooling performance of a conventional cooling device during a laser-based medical treatment
Figure 60:
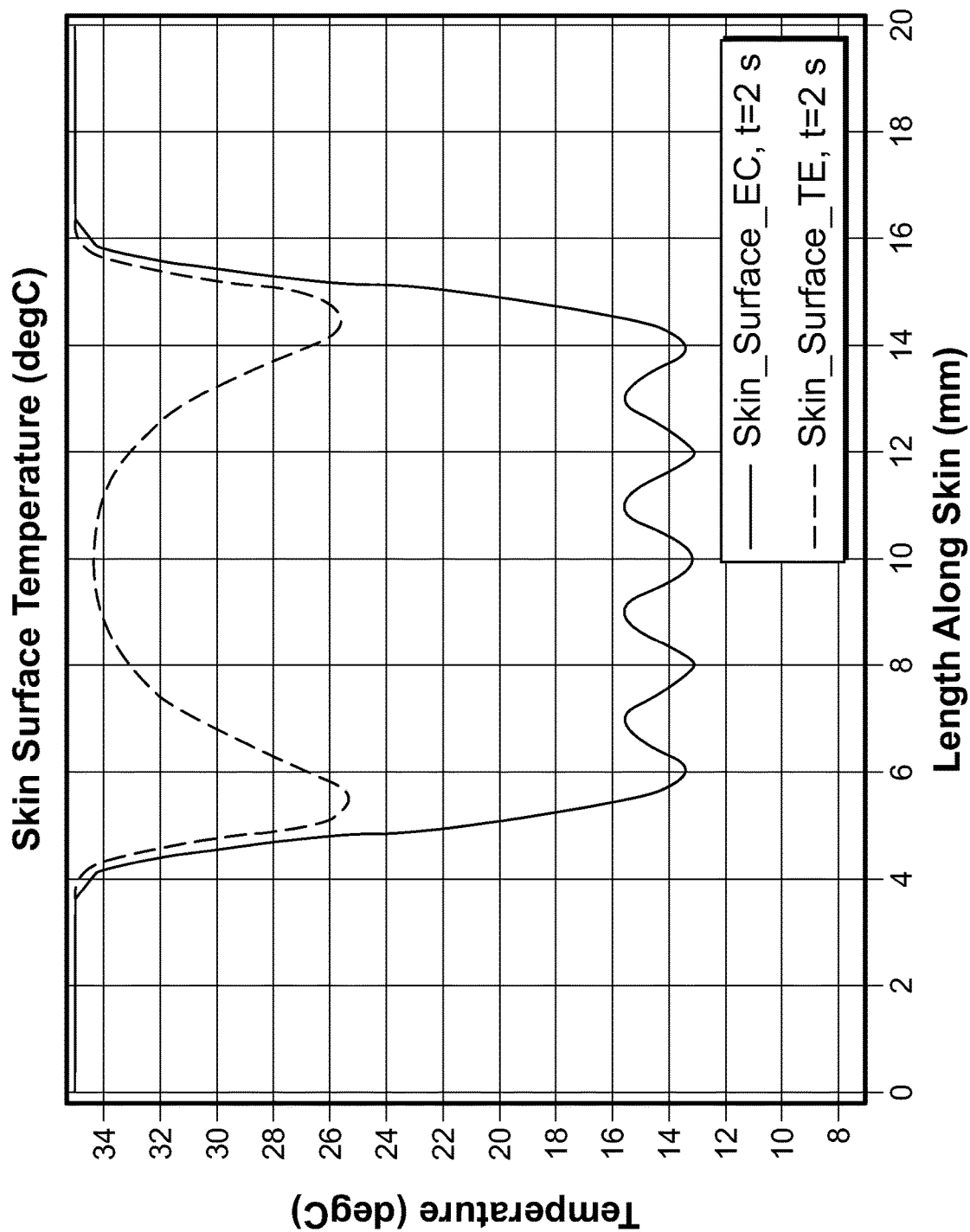
FIG. 60 is a graph illustrating a temperature at the skin surface two seconds after the cooling was initiated during a laser-based medical treatment for the noninvasive medical device of FIG. 58 and the conventional cooling device of FIG. 59.

FIG. 58 illustrates a setup used to model the cooling performance of the noninvasive medical device 1000 against the cooling performance of a conventional cooling device, which was modeled using the setup of FIG. 59. FIG. 60 is a graph illustrating the temperature a temperature at the skin surface two seconds after the cooling was initiated. As illustrated in FIG. 60, the conventional cooling system provided an extremely uneven temperature profiles and failed to uniformly cool the tissue. Conversely, the two-phase heat transfer leveraged by the noninvasive medical device 1000 provides significantly increased cooling capacity and was able to uniformly reduce the temperature of the skin to a temperature well below the conventional cooling device.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A noninvasive medical device configured to provide cooling to a tissue region, the noninvasive medical device comprising:
 a top plate;
 a bottom plate including a contact surface;
 an evaporative structure arranged between the top plate and the bottom plate configured to receive a working fluid, wherein the evaporative structure is configured to promote evaporation of the working fluid to cool the contact surface; and
 an opening extending through the top plate, the bottom plate, and the evaporative structure, wherein the opening enables fractional heat treatment to be performed on the tissue region via the opening.

2. The noninvasive medical device of claim 1, wherein further comprising a plurality of openings arranged in a fractional pattern of the fractional medical treatment.

3. The noninvasive medical device of claim 1, wherein the top plate, the bottom plate, and the evaporative structure is included in a base that includes a plurality of array tiles each including a plurality of array units, wherein the plurality of array units each include a proximal end, a distal end, and a portion of a plurality of channels arranged thereon.

4. The noninvasive medical device of claim 1, wherein the evaporative structure is in the form of a porous substrate.

5. The noninvasive medical device of claim 1, wherein the evaporative structure is in the form of a metal foam.

6. The noninvasive medical device of claim 1, wherein the evaporative structure is in the form of a plurality of channels extending from the opening.

7. The noninvasive medical device of claim 1, wherein the contact surface defines at least one of a concave shape, a convex shape, or a plurality of peaks and valleys.

8. The noninvasive medical device of claim 1, wherein the contact surface includes a plurality of protrusions extending therefrom.

9. The noninvasive medical device of claim 1, wherein the bottom plate defines at least one of a horseshoe shape, a banana shape, or an annular shape.

10. The noninvasive medical device of claim 1, wherein the opening is sealed between the top first plate and the bottom plate.

11. The noninvasive medical device of claim 1, wherein the working fluid is supplied to the evaporative structure from a fluid source.

12. The noninvasive medical device of claim 1, wherein the working fluid is at least one of a hydrocarbon, a hydrofluorocarbon, an alcohol, or water.

13. A medical device configured to provide cooling to a tissue region, the medical device comprising:
 an evaporative structure including:
  a plurality of channels each configured to receive a working fluid; and
  a plurality of apertures extending through the evaporative structure, the plurality of apertures to enable fractional heat treatment to be performed on the tissue region via the plurality of apertures; and
 a contact surface in engagement with the evaporative structure, wherein the plurality of apertures extend through the contact surface, and
 wherein heat from the contact surface is transferred to the evaporative structure to evaporate the working fluid in the plurality of channels and provide cooling to the contact surface adjacent to the plurality of apertures.

14. The medical device of claim 13, wherein the working fluid is supplied to the plurality of channels from a fluid source.

15. The medical device of claim 13, wherein the working fluid is at least one of a hydrocarbon, a hydrofluorocarbon, an alcohol, or water.

16. The medical device of claim 13, wherein the contact surface defines at least one of a concave shape, a convex shape, or a plurality of peaks and valleys.

17. The medical device of claim 13, wherein the contact surface includes a plurality of protrusions extending therefrom.

18. The medical device of claim 13, wherein a bottom plate of the medical device defines at least one of a horseshoe shape, a banana shape, or an annular shape.

19. The medical device of claim 13, wherein the evaporative structure is sealed between a top plate and a bottom plate, and wherein the contact surface is formed on the bottom plate.

20. The medical device of claim 19, wherein the plurality of apertures extend through the top plate and the bottom plate.

* * * * *